US 7,145,060 B2

(12) United States Patent
Muller et al.

(10) Patent No.: US 7,145,060 B2
(45) Date of Patent: Dec. 5, 2006

(54) NUCLEIC ACID ENCODING A CHITINASE AND METHODS OF USING IT TO MAKE FUNGAL RESISTANT PLANTS

(75) Inventors: Mathias L. Muller, Santa Cruz, CA (US); Thom True, Santa Clara, CA (US); Carl R. Simmons, Des Moines, IA (US); Nasser Yalpani, Johnston, IA (US)

(73) Assignees: Pioneer Hi-Bred International, Inc., DesMoines, IA (US); Verdia, Inc., Redwood City, CA (US)

( * ) Notice: Subject to any disclaimer, the term of this patent is extended or adjusted under 35 U.S.C. 154(b) by 248 days.

(21) Appl. No.: 10/389,432

(22) Filed: Mar. 14, 2003

(65) Prior Publication Data

US 2004/0250309 A1    Dec. 9, 2004

Related U.S. Application Data

(63) Continuation of application No. 10/290,086, filed on Nov. 6, 2002, now abandoned.

(60) Provisional application No. 60/337,029, filed on Nov. 7, 2001, provisional application No. 60/420,666, filed on Oct. 22, 2002.

(51) Int. Cl.
*A01H 5/00* (2006.01)
*C12N 15/82* (2006.01)
*C12N 15/56* (2006.01)

(52) U.S. Cl. .................. 800/301; 536/23.2; 435/320.1; 800/279; 800/320.1; 800/287

(58) Field of Classification Search ................ 800/278, 800/279, 288, 301; 536/23.6; 435/320.1, 435/468; 424/130.1; 530/350
See application file for complete search history.

(56) References Cited

OTHER PUBLICATIONS

Hill et al., Functional Analysis of Conserved Histidines in ADP-Glucose Pyrophosphorylase From *Escherichia coli*, Biochemical and Biophysical Research Communications, 244:573-577, 1998.*

Lazar et al., Transforming Growth Factor: Mutation of Aspartic Acid 47 and Leucine 48 Results in Different Biological Activities, Molecular and Cellular Biology, 8:1247-1252, 1988.*

Guo et al., Protein Tolerance to Random Amino Acid Change, PNAS., 101:9205-9210, 2004.*

Huynh et al., Antifungal Proteins From Plants, The Journal of Biological Chemistry, 267:6635-6640, 1992.*

Schnepf et al., Bacillus thuringiensis and its pesticidal crystal proteins, Microbial Mol Biol Rev.;62(3):775-806, 1998.*

Neuhaus et al., High-level expression of A Tobacco Chitinase Gene In *Nicotiana sylvestris*. Susceptibility Of Transgenic Plants To *Cercospora nicotianae* Infection., Plant Mole. Biol., 16: 141-51, 1991.*

Asao, H., et al., "Enhanced Resistance Against a Fungal Pathogen *Sphaerotheca humuli* in Transgenic Strawberry Expressing a Rice Chitinase Gene" Plant Biotech. 14(3):145-149 (1997).

Boller, T., "Hydrolytic Enzymes in Plant Disease Resistance" *In Plant Microbe Interactions, Molecular and Genetic Perspectives* vol. 2 (Ed. Nester, E.W. & Kosuge, T.) pp. 385-413 (1987).

(Continued)

*Primary Examiner*—Anne Kubelik
(74) *Attorney, Agent, or Firm*—Morgan & Finnegan LLP

(57) ABSTRACT

The present invention provides a nucleic acid encoding a chitinase and methods for it to enhance resistance of plants to fungal infections.

53 Claims, 14 Drawing Sheets

```
CLUSTAL W (1.82) multiple sequence alignment

56  SMQNCGCQPNVCCSKFGYCGTTDEYCGDGCQSGPCHSGGGGGGGGG------ANVASV
66  SMQNCGCQPNVCCSKFGYCGTTDEYCGDGCQSGPCRPGGGGGGGGGGGSGGANVASV
52  SMQNCGCQPNVCCSKFGYCGTTDEYCGDGCQSGPCRSGGGGSSGGGG------ANVASV
54  SMQNCGCQPNVCCSKFGYCGTTDEYCGAGCQSGPCHSGGGGSSGGGG------ANVASV
    ****************************** *******:.****.*****      ******

56  VTGSFFNGIKNQAGSGCEGKNFYTRSAFLSAVKAYPGFAHGGSQVQGKREIAAPFAHVTH
66  VTDSFFNGIKNQAGSGCEGKNFYTRSAFLSAVKAYPGFAHGGSQVQGKREIAAPFAHVTH
52  VTGSFFNGIKSQAGSGCEGKNFYTRSAFLSAVKAYPGFAHGGSQVQGKREIAAPFAHVTH
54  VTGSFFNGIKNQAGSGCEGKNFYTRSAFLSAVKAYPGFAHGGSQVQGKREIAAPFAHVTH
    **.*******.******************************************

56  ETGHFCYISEINKSNAYCDPTKRQWPCAAGQKYYGRGPLQISWNYNYGPAGRDIGFNGLA
66  ETGHFCYISEINKSNAYCDPTKRQWPCAAGQKYYGRGPLQISWNYNYGPAGRAIGFDGLA
52  ETGHFCYISEINKSNAYCDPTKRQWPCAAGQKYYGRGPLQISWNYNYGPAGRAIGFDGLG
54  ETGHFCYISEINKSNAYCDPTKRQWPCAAGQKYYGRGPLQLSWNYNYGPAGRDIGFNGLA
    *****************************************:********. ***:**.

56  DPNRVAQDAVVAPKAALWFWMNNVHRVMPGQFGATIRAINGALECGGNNPAQMNARIGYY
66  DPNRVAQDAVVAPKAALWFWMNNVHRVMPGQFGATIRAINGALECGGNNPAQMNARVGYY
52  DPGRVARDAVVAPKAALWFWMNNVHRVMPGQFGATIRAINGALECGGNNPAQMNARVGYY
54  DPNRVAQDAVIAPKSALWFWMNNVHRVMPGQFGATIRAINGALECGGNNPAQMNARVGYY
    **.***.***:***:***************************************:***

56  KQYCRQLGVDPGPNLTC
66  KQYCRQLGVDPGPNLTC
52  RQYCRQLGVDPGPNLTC
54  RQYCRQLGVDPGPNLTC
    :****************
```

OTHER PUBLICATIONS

Broglie, K., et al., "Transgenic Plants with Enhanced Resistance to the Fungal Pathogen *Rhizoctonia solani*" Science 254:1194-1197 (1991).

Collinge, D., et al., "Plant Chitinases" Plant J. 3:31-40 (1993).

Cosio, I., et al., "Bioconversion of Shellfish Chitin Waste: Waste Pretreatment, Enzyme Production, Process Design, and Economic Analysis" J. Food Sci. 47:901-905 (1982).

Ding, X., et al., "Insect Resistance of Transgenic Tobacco Expressing an Insect Chitinase Gene" Transgenic Res. 7(2):77-84 (1998).

Gianinazzi, S., "Genetic and Molecular Aspects of Resistance Induced by Infections or Chemicals" *In Plant Microbe Interactions, Molecular and Genetic Perspectives*, vol. 1 (Ed. Nester, E.W. & Kosuge, T.) pp. 321-342 (1987).

Grison, R., et al., "Field Tolerance to Fungal Pathogens of *Brassica napus* Constitutively Expressing a Chimeric Chitinase Gene" Nature Biotech. 14:643-646 (1996).

Hamel, F., et al., "Structural and Evolutionary Relationships Among Chitinases of Flowering Plants" J. Mol. Evol. 44(6):614-24 (1997).

Legrand, M., et al., "Biological Function of Pathogenesis-related Proteins: Four Tobacco Pathogenesis-related Proteins Are Chitinases" Proc. Natl. Acad. Sci. USA 84:6750-6754 (1987).

Lorito, M., et al., "Genes from Mycoparasitic Fungi As a Source for Improving Plant Resistance to Fungal Pathogens" Proc. Natl. Acad. Sci. USA 95:7860-7865 (1998).

Mauch, F., et al., "Antifungal Hydrolases in Pea Tissue: Inhibition of Fungal Growth by Combinations of Chitinase and β-1,3-Glucanase" Plant Physiol. 88:936-942 (1988).

Neuhaus, J., et al., "High Level Expression of a Tobacco Chitinase Gene in *Nicotiana sylvestris*. Susceptibility of Transgenic Plants to *Cercospora nicotianae*" Plant Mol. Biol. 16:141-151 (1991).

Tabei, Y., et al., "Transgenic Cucumber Plants Harboring a Rice Chitinase Gene Exhibit Enhanced Resistance to Gray Mold (*Botrytis cinerea*)" Plant Cell Rep. 17:159-164 (1998).

Vierheilig, H., et al., "Colonization of Transgenic *Nicotiana sylvestris* Plants, Expressing Different Forms of *Nicotiana tabacum* Chitinase, by the Root Pathogen *Rhizoctonia solani* and by the *Mycorrhizal Symbiont Glomus mosseae*" Molecular Plant-microbe Interactions 6:261-264 (1993).

\* cited by examiner

FIGURE 1

CLUSTAL W (1.82) multiple sequence alignment

```
56    SMQNCGCQPNVCCSKFGYCGTTDEYCGDGCQSGPCHSGGGGGGGGG-------ANVASV
66    SMQNCGCQPNVCCSKFGYCGTTDEYCGDGCQSGPCRPGGGGGGGGGGGGSGGANVASV
52    SMQNCGCQPNVCCSKFGYCGTTDEYCGDGCQSGPCRSGGGGSSGGGG-------ANVASV
54    SMQNCGCQPNVCCSKFGYCGAGCQSGPCHSGGGGSSGGGG-------ANVASV
      ********************* ******:.****..****       ******

56    VTGSFFNGIKNQAGSGCEGKNFYTRSAFLSAVKAYPGFAHGGSQVQGKREIAAFFAHVTH
66    VTDSFFNGIKNQAGSGCEGKNFYTRSAFLSAVKAYPGFAHGGSQVQGKREIAAFFAHVTH
52    VTGSFFNGIKSQAGSGCEGKNFYTRSAFLSAVKAYPGFAHGGSQVQGKREIAAFFAHVTH
54    VTGSFFNGIKNQAGSGCEGKNFYTRSAFLSAVKAYPGFAHGGSQVQGKREIAAFFAHVTH
      **.******.**************************************************

56    ETGHFCYISEINKSNAYCDPTKRQWPCAAGQKYYGRGPLQISWNYNYGPAGRDIGFNGLA
66    ETGHFCYISEINKSNAYCDPTKRQWPCAAGQKYYGRGPLQISWNYNYGPAGRAIGFDGLA
52    ETGHFCYISEINKSNAYCDPTKRQWPCAAGQKYYGRGPLQISWNYNYGPAGRAIGFDGLG
54    ETGHFCYISEINKSNAYCDPTKRQWPCAAGQKYYGRGPLQLSWNYNYGPAGRDIGFNGLA
      ****************************************:*********** ***:**.

56    DPNRVAQDAVVAFKAALWFWMNNVHRVMPQGPGATIRAINGALECGGNNPAQMNARIGYY
66    DPNRVAQDAVVAFKAALWFWMNNVHRVMPQGPGATIRAINGALECGGNNPAQMNARVGYY
52    DPGRVARDAVVAFKAALWFWMNNVHRVMPQGPGATIRAINGALECGGNNPAQMNARVGYY
54    DPNRVAQDAVIAFKSALWFWMNNVHRVMPQGPGATIRAINGALECGGNNPAQMNARVGYY
      **.***:***::***.***********************************:***

56    KQYCRQLGVDPGPNLTC
66    KQYCRQLGVDPGPNLTC
52    RQYCRQLGVDPGPNLTC
54    RQYCRQLGVDPGPNLTC
      :****************
```

FIGURE 2

CLUSTAL W (1.82) multiple sequence alignment

```
53  TCGATGCAGAACTGCGGCTGCCAGCCAAACGTATGCTGCAGCAAGTTTGGCTACTGCGGC
55  TCGATGCAGAACTGCGGCTGCCAGCCAAACGTATGCTGCAGCAAGTTTGGCTACTGCGGC
65  TCGATGCAGAACTGCGGCTGCCAGCCAAACGTATGCTGCAGCAAGTTTGGCTACTGCGGC
51  TCGATGCAGAACTGCGGCTGCCAGCCAAACGTATGCTGCAGCAAGTTTGGCTACTGCGGC
    ************************************************************

53  ACGACCGACGAGTACTGCGGCGCCGGGTGCCAGTCGGGCCCGTGCCACTCGGGCGGCGGC
55  ACAACCGACGAGTACTGCGGCGACGGGTGCCAGTCGGGCCCGTGCCACTCGGGCGGCGGT
65  ACGACCGACGAGTACTGCGGCGACGGGTGCCAGTCGGGCCCGTGCCGCCCGGGTGGCGGT
51  ACGACCGACGAGTACTGCGGCGACGGGTGCCAGTCGGGCCCGTGCCGCTCGGGCGGCGGC
    ** ****************** **************************  *  *  ****

53  GGCAGCAGTGGCGGCGG--------------------TGGTGCGAACGTGGCTAGCGTC
55  GGCGGCGGTGGCGGCGG--------------------TGGTGCGAACGTGGCTAGCGTC
65  GGCGGCGGCGGCGGCGGCGGAGGCGGCGGAGGCAGTGGTGGTGCGAACGTGGCTAGCGTC
51  GGCAGCAGTGGCGGCGG--------------------TGGTGCGAACGTGGCTAGCGTC
    ***  **  ********                    **********************

53  GTCACCGGCTCCTTCTTCAACGGCATCAAGAACCAGGCCGGGAGCGGGTGCGAGGGCAAG
55  GTCACCGGCTCCTTCTTCAACGGCATCAAGAACCAGGCCGGGAGCGGGTGCGAGGGCAAG
65  GTCACCGACTCCTTCTTCAACGGCATCAAGAACCAGGCCGGGAGCGGGTGCGAGGGCAAG
51  GTCACCGGCTCCTTCTTCAACGGCATCAAGAGCCAGGCCGGGAGCGGGTGCGAGGGCAAG
    *******  ********************** ****************************

53  AACTTCTACACCCGGAGCGCGTTCCTGAGCGCCGTCAAGGCGTACCCAGGCTTCGCCCAT
55  AACTTCTACACCCGGAGCGCGTTCCTGAGCGCCGTCAAGGCGTACCCAGGCTTCGCCCAT
65  AACTTCTACACCCGGAGCGCGTTCCTGAGCGCCGTCAAGGCGTACCCAGGCTTCGCCCAT
51  AACTTCTACACCCGGAGCGCGTTCCTGAGCGCCGTCAAGGCGTACCCAGGCTTCGCCCAT
    ************************************************************

53  GGCGGGTCGCAGGTGCAGGGCAAGCGCGAGATCGCCGCCTTCTTCGCGCATGTCACGCAT
55  GGCGGGTCACAGGTGCAGGGCAAGCGCGAGATCGCCGCCTTCTTCGCGCATGTCACGCAC
65  GGCGGGTCGCAGGTGCAGGGCAAGCGCGAGATCGCCGCCTTCTTCGCGCATGTCACGCAC
51  GGCGGGTCGCAGGTGCAGGGCAAGCGCGAGATCGCCGCCTTCTTCGCGCATGTCACGCAC
    ********  **************************************************

53  GAGACCGGGCATTTCTGCTACATCAGCGAGATCAACAAGAGCAACGCCTACTGCGACCCG
55  GAGACCGGGCATTTCTGCTACATCAGCGAGATCAACAAGAGCAACGCCTACTGCGACCCG
65  GAGACCGGGCATTTCTGCTACATCAGCGAGATCAACAAGAGCAACGCCTACTGCGACCCG
51  GAGACCGGGCATTTCTGCTACATCAGCGAGATCAACAAGAGCAACGCCTACTGCGACCCG
    ************************************************************

53  ACCAAGAGGCAGTGGCCGTGCGCCGCGGGGCAGAAGTACTACGGGCGCGGCCCGCTGCAG
55  ACCAAGAGGCAGTGGCCGTGCGCCGCGGGGCAGAAGTACTACGGGCGCGGCCCGCTGCAG
65  ACCAAGAGGCAGTGGCCGTGCGCCGCGGGGCAGAAGTACTACGGGCGTGGCCCGCTGCAG
51  ACCAAGAGGCAGTGGCCGTGCGCCGCGGGGCAGAAGTACTACGGGCGCGGCCCGCTGCAG
    *********************************************** ************

53  CTGTCGTGGAACTACAACTACGGGCCCGCCGGGAGGGACATCGGCTTCAACGGGCTCGCC
55  ATCTCGTGGAACTACAACTACGGGCCCGCGGGGAGGGACATCGGCTTCAACGGGCTCGCC
65  ATCTCGTGGAACTACAACTACGGGCCCGCGGGGAGGGCCATCGGCTTCGACGGGCTCGCC
51  ATCTCGTGGAACTACAACTACGGGCCCGCGGGGAGGGCCATCGGCTTCGACGGGCTCGGG
     * ************************ ******** ***********  *******  
```

FIGURE 3

```
53  GACCCCAACAGGGTGGCGCAGGACGCCGTGATCGCGTTCAAGTCGGCGCTCTGGTTCTGG
55  GACCCCAACAGGGTGGCGCAGGACGCCGTGGTGGCGTTCAAGGCGGCGCTCTGGTTCTGG
65  GACCCCAACAGGGTGGCGCAGGACGCCGTGGTGGCGTTCAAGGCGGCGCTCTGGTTCTGG
51  GACCCCGGCAGGGTGGCGCGGGACGCCGTGGTGGCGTTCAAGGCGGCGCTCTGGTTCTGG
    *****  *********  ********* *  ********  *******************

53  ATGAACAACGTGCACCGTGTGATGCCGCAGGGCTTCGGCGCCACCATCAGGGCCATCAAC
55  ATGAACAACGTGCACCGTGTGATGCCGCAGGGCTTCGGCGCCACCATCAGGGCCATCAAC
65  ATGAACAACGTGCACCGTGTGATGCCGCAGGGCTTCGGCGCCACCATCAGGGCCATCAAC
51  ATGAACAACGTGCACCGTGTGATGCCGCAGGGCTTCGGCGCCACCATCAGGGCCATCAAC
    ************************************************************

53  GGCGCCCTCGAGTGCGGCGGGAACAACCCCGCCCAGATGAACGCGCGCGTCGGCTACTAC
55  GGCGCCCTCGAGTGCGGCGGGAACAACCCCGCCCAGATGAACGCGCGCATCGGCTACTAC
65  GGCGCCCTCGAGTGCGGCGGGAACAACCCCGCCCAGATGAACGCGCGCGTCGGCTACTAC
51  GGCGCCCTCGAGTGCGGCGGGAACAACCCCGCCCAGATGAACGCGCGCGTCGGCTACTAC
    ************************************************  **********

53  AGGCAGTACTGCCGCCAGCTCGGCGTCGACCCAGGGCCCAACCTCACTTGC
55  AAGCAGTACTGCCGCCAGCTCGGCGTCGACCCAGGGCCCAACCTCACTTGC
65  AAGCAGTACTGCCGCCAGCTCGGCGTCGACCCAGGGCCCAACCTCACTTGC
51  AGGCAGTACTGCCGCCAGCTCGGCGTCGACCCAGGGCCCAACCTCACTTGC
    * *************************************************
```

FIGURE 4
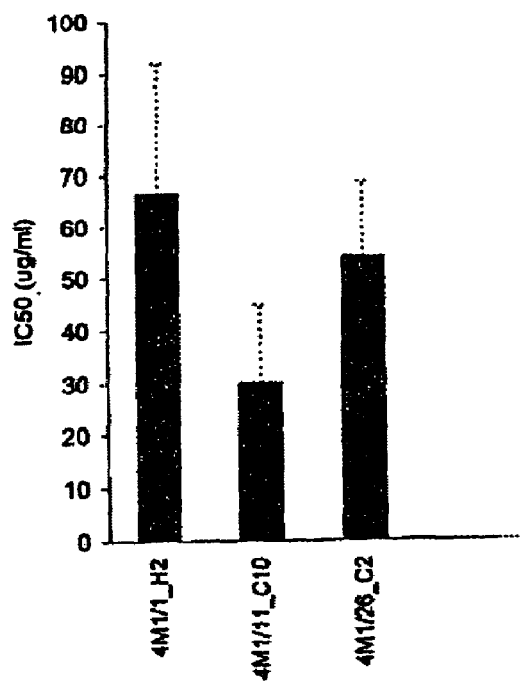
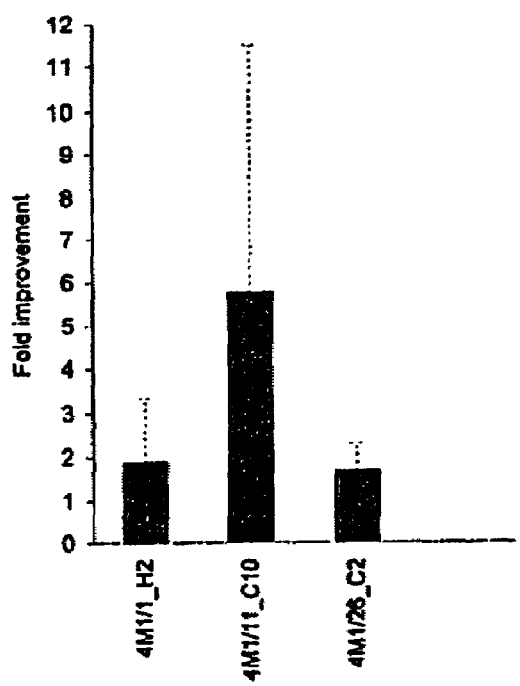

```
              *         20          *         40          *         60          *
4H1/1_H2   : SHQNCGCQPNVCCSKYGYCGTTDYYCGDGCQSCPCRSGCCGSSGGGGCCCGSCCANVANVVTDAFFNGIK : 70
4H1/11_C10 : .......ASG..........................----SS...---.....S...GS...... : 63
4H1/26_C2  : .......ASG..........GND...A................---........................ : 67

80          *        100          *        120          *        140
4H1/1_H2   : NQACSWCEGNNFYTRSAFLSAVNAYPGFAHCGSQVQGKREIAAFFARVTHETGHLCYINEVNKSNATCDP : 140
4H1/11_C10 : S....C.................................A......Y...S............ : 133
4H1/26_C2  : ......C.................................R......Y...S............ : 137

*        160          *        180          *        200          *
4H1/1_H2   : TKRQWPCAAGGHYYGRGPLQISWNYNYGPAGRAIGFDGLGDPDRLAGDPVLSFREALWFWNNVVHRVKPQ : 210
4H1/11_C10 : ...........................................G..R.A..A..A.......... : 203
4H1/26_C2  : ..........................................................A.......... : 207

220         *        240          *
4H1/1_H2   : CYGATIRAINGALECCGNNPAQNNARVGYYRQYCRQLCVDPCKNLTC : 257
4H1/11_C10 : ..............N..............Q..N....P.... : 250
4H1/26_C2  : ..............N.............................. : 254
```

[Sequence alignment figure showing multiple protein sequences aligned across positions 1-250. The alignment includes sequences labeled r1AB2, r1AD4, r1AD6, r1AC9, r1AB8, r1AH9, r1BC5, r2C5, 4N1/95_E3, 4N1/80_F8, 4N1/75_D3, 4N1/2_H9, 4N1/23_C4, 4N1/68_E4, 4N1/88_F9, 4N1/14_B3, 4N1/33_F4, 4N1/11_B11, 4N1/30_D3, and 4N1/35_G5. The top reference sequence (r1AB2) reads approximately: SHQHCGCQPNYCCSKFGYCGTTDAYCGDCCQSQPCRSGGGGSGGG------GANVASVVYCSPFWGIKSQAGSCCDCWSYYTRSAFL (82), then SAVHAYPQFAWGGSNVRHKHSIAAFFAHFTHSTGNPCYISKIHRSAAYCPFTNRQFPCAACGNYYGCACPLQISWNYHYCFACRAICFDCLG (173), then DPGNVARDAVVAFKAALSFKQNNVHNVHPQGFGATIRAINCALSCDCKNFNSVHWRVAYYKQFCQDPCVDPCPWLTC (250). The other sequences show variations indicated by letter substitutions with dots representing identical residues.]

NUCLEIC ACID ENCODING A CHITINASE AND METHODS OF USING IT TO MAKE FUNGAL RESISTANT PLANTS

CROSS-REFERENCE TO RELATED APPLICATION

This application is a continuation of U.S. Ser. No. 10/290,086 filed 6 Nov. 2002 now abandoned, which claims the benefit of priority under 35 U.S.C. § 119(e) to provisional applications 60/337,029 filed 7 Nov. 2001 and 60/420,666 filed 22 Oct. 2002. The contents of these applications are incorporated herein by reference.

BACKGROUND OF THE INVENTION

Plant chitinases belong to a family of pathogenesis-related (PR) proteins, which are over-expressed by plants in response to a pathogen attack (Giazinazzi, In Plant Microbe Interactions, Molecular and Genetic Perspectives, Vol. 1 (ed. Nester, E. W. & Kosuge T., 1987) 321–342; Boller, T., *Id.*, Vol. 2, 385–413; Legrand, M., et al. *Proc. Natl. Acad. Sci USA* 84:6750–6754 (1987); Collinge, et al., *Plant J.* 3:31–40 (1993). Chitinases catalyze the hydrolysis of the β-1,4 linked N-acetylglucosamine polymers that form chitin chains, a major component of fungal cell walls. Chitinases have been divided based on their structure into at least four classes (classes i–iv). See, e.g., Hamel, et al., *J. Mol. Evol.* 44(6):614–24 (1997).

Even though chitinases have been shown to inhibit the hyphal tip growth of many fungi in vitro (Mauch, et al. *Plant Physiol.* 88:936–942 (1988)), a plant's natural defense mechanisms are often insufficient to prevent an invasion by the pathogen (Neuhaus, et al. *Plant Mol. Biol.* 16, 141–151 (1991)). The consequences of plant disease caused by fungal pathogens can be significant losses in crop quality and yields. Plants over-expressing chitinases under the control of a strong constitutive promoter have been engineered and have shown improved resistance against fungal pathogens under laboratory conditions (Broglie, et al. *Science* 254: 1194–1197 (1991), Vierheilig, et al. *Molecular Plant-microbe Interactions* 6:261–264 (1993); Asao, et al. *Plant Biotech.* 14: 145–149 (1997); Tabei, *Plant Cell Rep.* 17: 159–164 (1998); Lorito et al., *Proc. Natl. Acad. Sci. USA* 95:7860–7865 (1998). Further, plants constitutively over-expressing a hybrid endochitinase exhibited improved tolerance to fungal diseases in field tests (Grison, et al. *Nature Biotech.* 14:643–646 (1996)).

The expression of chitinases in plants is therefore useful to enhance resistance in plants to fungi, including fungal pathogens. Chitinases expressed in plants are also reported to have anti-insect activity. See, e.g., Ding, et al., *Transgenic Res.* 7(2):77–84 (1998). Additionally, chitinases are useful in industrial processes aimed at the bioconversion of shellfish chitin waste (Cosio, et al. *J. Food Sci.* 47:901–905 (1982)).

Although expression of chitinases can be useful to reduce infection by fungal pathogens and other pests, constitutive overexpression of foreign proteins in crop plants has a potentially yield-reducing metabolic cost. Moreover, it is commonly found that particular chitinases only have anti-fungal activity against a narrow range of fungal pathogens. Thus, chitinases with high activity and broad specificity are needed.

SUMMARY OF THE INVENTION

The present invention provides isolated nucleic acids comprising a polynucleotide encoding a chitinase polypeptide, wherein the chitinase polypeptide is selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, and SEQ ID NO:66. The chitinase polypeptides of the present invention exhibit a chitinase activity of at least 20% of the chitinase activity of Chitinase A (SEQ ID NO:1) to at least 200% of the chitinase activity of Chitinase A (SEQ ID NO:1).

The invention also provides for isolated nucleic acids comprising a polynucleotide encoding a chitinase polypeptide, wherein the chitinase polypeptide is substantially identical and/or substantially similar to a polypeptide selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, and SEQ ID NO:66. For example, the invention provides for isolated nucleic acids comprising a polynucleotide encoding a chitinase polypeptide, wherein the chitinase polypeptide is selected from the group consisting of a polypeptide at least 90% identical to SEQ ID NO:4, at least 89% identical to SEQ ID NO:6, at least 91% identical to SEQ ID NO:8, at least 88% identical to SEQ ID NO:10, at least 91% identical to SEQ ID NO:12, at least 89% identical to SEQ ID NO:14, at least 87% identical to SEQ ID NO:16, at least 96% identical to SEQ ID NO:22, at least 90% identical to SEQ ID NO:24, at least 89% identical to SEQ ID NO:26, at least 92% identical to SEQ ID NO:28, at least 92% identical to SEQ ID NO:30, at least 95% identical to SEQ ID NO:32, at least 92% identical to SEQ ID NO:34, at least 95% identical to SEQ ID NO:36, at least 93% identical to SEQ ID NO:38, at least 90% identical to SEQ ID NO:40, at least 90% identical to SEQ ID NO:42, at least 96% identical to SEQ ID NO:44, at least 94% identical to SEQ ID NO:46, at least 95% identical to SEQ ID NO:48, at least 96% identical to SEQ ID NO:50, at least 99% identical to SEQ ID NO:52, at least 95% identical to SEQ ID NO:54, at least 95% identical to SEQ ID NO:56, at least 93% identical to SEQ ID NO:58, at least 93% identical to SEQ ID NO:60, at least 93% identical to SEQ ID NO:62, at least 93% identical to SEQ ID NO:64, and at least 93% identical to SEQ ID NO:66. These chitinase polypeptides have a chitinase activity of at least 20% of the chitinase activity of Chitinase A (SEQ ID NO:1) to at least 200% of the chitinase activity of Chitinase A (SEQ ID NO:1).

The present invention provides isolated nucleic acids comprising a chitinase polynucleotide encoding a polypeptide having chitinase activity, wherein the polynucleotide is selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, and SEQ ID NO:65.

In some embodiments, the nucleic acid further comprises a promoter operably linked to the polynucleotide. The promoter may be a tissue-specific promoter, a constitutive promoter or an inducible promoter. The present invention also provides vectors comprising a nucleic acid of the invention operably linked to a promoter, which may be tissue-specific, constitutive or inducible.

The present invention also provides isolated nucleic acids comprising a chitinase polynucleotide encoding a polypeptide with chitinase activity, wherein the polynucleotide specifically hybridizes following at least one wash in 0.2×SSC at 55° C. for 20 minutes to a probe polynucleotide selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 and SEQ ID NO:65, with the proviso that the chitinase polynucleotide does not encode SEQ ID NO:2, SEQ ID NO:17 SEQ ID NO:18, SEQ ID NO:19 or SEQ ID NO:20. The polypeptides exhibit a chitinase activity of at least 20% of the chitinase activity of Chitinase A (SEQ ID NO:1) to at least 200% of the chitinase activity of Chitinase A (SEQ ID NO:1). In some embodiments, the isolated nucleic acid does not encode SEQ ID NO:4, SEQ ID NO:6, SEQ ID NO:8, SEQ ID NO:10, SEQ ID NO:12, SEQ ID NO:14, or SEQ ID NO:16.

The present invention also provides isolated nucleic acids of at least 20 nucleotides in length, wherein the nucleic acid encodes an amino acid subsequence selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64 and SEQ ID NO:66, with the proviso that the nucleic acid does not encode an amino acid subsequence of SEQ ID NO:2, SEQ ID NO:17, SEQ ID NO:18, SEQ ID NO:19 or SEQ ID NO:20. In some embodiments, the isolated nucleic acid does not encode an amino acid subsequence of SEQ ID NO:4, SEQ ID NO:6, SEQ ID NO:8, SEQ ID NO:10, SEQ ID NO:12, SEQ ID NO:14 or SEQ ID NO:16.

The present invention provides isolated chitinase polypeptides selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64 and SEQ ID NO:66.

The present invention also provides an isolated chitinase polypeptide selected from the group consisting of a polypeptide at least 90% identical to SEQ ID NO:4, a polypeptide at least 89% identical to SEQ ID NO:6, a polypeptide at least 91% identical to SEQ ID NO:8, a polypeptide at least 88% identical to SEQ ID NO:10, a polypeptide at least 91% identical to SEQ ID NO:12, a polypeptide at least 89% identical to SEQ ID NO:14, a polypeptide at least 87% identical to SEQ ID NO:16, a polypeptide at least 96% identical to SEQ ID NO:22, a polypeptide at least 90% identical to SEQ ID NO:24, a polypeptide at least 89% identical to SEQ ID NO:26, a polypeptide at least 92% identical to SEQ ID NO:28, a polypeptide at least 92% identical to SEQ ID NO:30, a polypeptide at least 95% identical to SEQ ID NO:32, a polypeptide at least 92% identical to SEQ ID NO:34, a polypeptide at least 95% identical to SEQ ID NO:36, a polypeptide at least 93% identical to SEQ ID NO:38, a polypeptide at least 90% identical to SEQ ID NO:40, a polypeptide at least 90% identical to SEQ ID NO:42, a polypeptide at least 96% identical to SEQ ID NO:44, a polypeptide at least 94% identical to SEQ ID NO:46, a polypeptide at least 95% identical to SEQ ID NO:48, a polypeptide at least 96% identical to SEQ ID NO:50, a polypeptide at least 99% identical to SEQ ID NO:52, a polypeptide at least 95% identical to SEQ ID NO:54, a polypeptide at least 95% identical to SEQ ID NO:56, a polypeptide at least 93% identical to SEQ ID NO:58, a polypeptide at least 93% identical to SEQ ID NO:60, a polypeptide at least 93% identical to SEQ ID NO:62, a polypeptide at least 93% identical to SEQ ID NO:64, and a polypeptide at least 93% identical to SEQ ID NO:66. These polypeptides exhibit a chitinase activity of at least 20% of the chitinase activity of Chitinase A (SEQ ID NO:1) to at least 200% of the chitinase activity of Chitinase A (SEQ ID NO:1).

The present invention also provides antibodies capable of specifically binding an isolated polypeptide selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64 and SEQ ID NO:66.

The present invention also provides plants comprising a recombinant expression cassette comprising a promoter operably linked to a polynucleotide encoding a chitinase polypeptide having chitinase activity, wherein the polypeptide is selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64 and SEQ ID NO:66. The chitinase polypeptides exhibit a chitinase activity of at least 20% of the chitinase activity of Chitinase A (SEQ ID NO:1) to at least 200% of the chitinase activity of Chitinase A (SEQ ID NO:1). In some embodiments, the promoter is a tissue-specific promoter, while in other embodiments the promoter is a constitutive promoter, while yet in other embodiments the promoter is an inducible promoter. In some embodiments, the plant is maize.

The present invention also provides plants comprising a recombinant expression cassette comprising a promoter operably linked to a polynucleotide encoding a chitinase polypeptide with chitinase activity, wherein the polypeptide is selected from the group consisting of a polypeptide at least 90% identical to SEQ ID NO:4, a polypeptide at least 89% identical to SEQ ID NO:6, a polypeptide at least 91% identical to SEQ ID NO:8, a polypeptide at least 88% identical to SEQ ID NO:10, a polypeptide at least 91% identical to SEQ ID NO:12, a polypeptide at least 89% identical to SEQ ID NO:14, a polypeptide at least 87% identical to SEQ ID NO:16, a polypeptide at least 96% identical to SEQ ID NO:22, a polypeptide at least 90% identical to SEQ ID NO:24, a polypeptide at least 89% identical to SEQ ID NO:26, a polypeptide at least 92% identical to SEQ ID NO:28, a polypeptide at least 92% identical to SEQ ID NO:30, a polypeptide at least 95% identical to SEQ ID NO:32, a polypeptide at least 92% identical to SEQ ID NO:34, a polypeptide at least 95% identical to SEQ ID NO:36, a polypeptide at least 93% identical to SEQ ID NO:38, a polypeptide at least 90% identical to SEQ ID NO:40, a polypeptide at least 90% identical to SEQ ID NO:42, a polypeptide at least 96% identical to SEQ ID NO:44, a polypeptide at least 94% identical to SEQ ID NO:46, a polypeptide at least 95% identical to SEQ ID NO:48, a polypeptide at least 96% identical to SEQ ID NO:50, a polypeptide at least 99% identical to SEQ ID NO:52, a polypeptide at least 95% identical to SEQ ID NO:54, a polypeptide at least 95% identical to SEQ ID NO:56, a polypeptide at least 93% identical to SEQ ID NO:58, a polypeptide at least 93% identical to SEQ ID NO:60, a polypeptide at least 93% identical to SEQ ID NO:62, a polypeptide at least 93% identical to SEQ ID NO:64, and a polypeptide at least 93% identical to SEQ ID NO:66. These chitinase polypeptides exhibit a chitinase activity of at least 20% of the chitinase activity of Chitinase A (SEQ ID NO:1) to at least 200% of the chitinase activity of Chitinase A (SEQ ID NO:1). In some embodiments, the promoter is a tissue-specific promoter, while in other embodiments the promoter is a constitutive promoter, while yet in other embodiments the promoter is an inducible promoter. In some embodiments, the plant is maize.

The present invention also provides methods of enhancing plant resistance to a fungus. The method comprises a) introducing into a plant a recombinant expression cassette comprising a promoter operably linked to a polynucleotide encoding a chitinase polypeptide having chitinase activity, wherein the polypeptide is selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64 and SEQ ID NO:66; and b) selecting a plant with enhanced resistance to a fungus.

The present invention also provides methods of enhancing plant resistance to a fungus comprising a) introducing into a plant a recombinant expression cassette comprising a promoter operably linked to a polynucleotide encoding a chitinase polypeptide having chitinase activity, wherein the polypeptide is selected from the group consisting of a polypeptide at least 90% identical to SEQ ID NO:4, a polypeptide at least 89% identical to SEQ ID NO:6, a polypeptide at least 91% identical to SEQ ID NO:8, a polypeptide at least 88% identical to SEQ ID NO:10, a polypeptide at least 91% identical to SEQ ID NO:12, a polypeptide at least 89% identical to SEQ ID NO:14, a polypeptide at least 87% identical to SEQ ID NO:16, a polypeptide at least 96% identical to SEQ ID NO:22, a polypeptide at least 90% identical to SEQ ID NO:24, a polypeptide at least 89% identical to SEQ ID NO:26, a polypeptide at least 92% identical to SEQ ID NO:28, a polypeptide at least 92% identical to SEQ ID NO:30, a polypeptide at least 95% identical to SEQ ID NO:32, a polypeptide at least 92% identical to SEQ ID NO:34, a polypeptide at least 95% identical to SEQ ID NO:36, a polypeptide at least 93% identical to SEQ ID NO:38, a polypeptide at least 90% identical to SEQ ID NO:40, a polypeptide at least 90% identical to SEQ ID NO:42, a polypeptide at least 96% identical to SEQ ID NO:44, a polypeptide at least 94% identical to SEQ ID NO:46, a polypeptide at least 95% identical to SEQ ID NO:48, a polypeptide at least 96% identical to SEQ ID NO:50, a polypeptide at least 99% identical to SEQ ID NO:52, a polypeptide at least 95% identical to SEQ ID NO:54, a polypeptide at least 95% identical to SEQ ID NO:56, a polypeptide at least 93% identical to SEQ ID NO:58, a polypeptide at least 93% identical to SEQ ID NO:60, a polypeptide at least 93% identical to SEQ ID NO:62, a polypeptide at least 93% identical to SEQ ID NO:64, and a polypeptide at least 93% identical to SEQ ID NO:66; and b) selecting a plant with enhanced resistance to a fungus.

In some embodiments, the promoter is a tissue-specific promoter, while in other embodiments the promoter is a constitutive promoter, and in yet other embodiments the promoter is an inducible promoter. In some embodiments, the plant is maize. In some embodiments, the fungus is from the genus *Fusarium*.

Definitions

"Anti-fungal activity" refers to the ability of a polypeptide to inhibit fungal growth or pathogenesis on or in plants or the ability to inhibit growth or lyse fungal cells in vitro in cell media as described herein. For example, in some embodiments, the anti-fungal activity is sufficient to inhibit fungal growth by at least 10%, sometimes 50%, and sometimes at least 90% compared to growth on media or plants without the polypeptide. Similarly, in some embodiments of the invention plants expressing polypeptides with anti-fungal activity have at least 10% fewer disease symptoms, sometimes 50% and sometimes at least 90% compared to equivalent plants not expressing the polypeptide. Symptoms will vary based on the fungal pathogen, but can include damping off of seedlings, lesion development or other symptoms known to those of skill in the art.

The phrase "nucleic acid sequence" refers to a single or double-stranded polymer of deoxyribonucleotide or ribonucleotide bases read from the 5' to the 3' end. It includes chromosomal DNA, self-replicating plasmids and DNA or RNA that performs a primarily structural role.

The term "encoding" refers to a polynucleotide sequence encoding one or more amino acids. The term does not require a start or stop codon. An amino acid sequence can be encoded in any one of six different reading frames provided by a polynucleotide sequence.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable of replication in a host organism. Examples of vectors include plasmids and typically have an origin of replication. Vectors can comprise, e.g., transcription and translation terminators, transcription and translation initiation sequences, and promoters useful for regulation of the expression of the particular nucleic acid.

The term "plant" includes whole plants, shoots, vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous plants.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A polynucleotide "exogenous to" an individual plant is a polynucleotide which is introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as a $T_1$ (e.g. in *Arabidopsis* by vacuum infiltration) or $R_0$ (for plants regenerated from transformed cells in vitro) generation transgenic plant. Transgenic plants that arise from sexual cross or by selfing are descendants of such a plant.

A "chitinase nucleic acid" or "chitinase polynucleotide sequence" of the invention is a polynucleotide sequence or subsequence (e.g., odd numbered sequences from SEQ ID NO:3 to SEQ ID NO:15 and SEQ ID NO:21 to SEQ ID NO:65) which, encodes a chitinase polypeptide (e.g., even numbered sequences from SEQ ID NO:4 to SEQ ID NO:16 and SEQ ID NO:22 to SEQ ID NO:66, respectively) with chitinase activity. "Chitinase" refers to a polypeptide capable of enzymatically hydrolyzing β-1,4 linked N-acetylglucosamine polymers (chitin). See, e.g., Watanabe, et al. *Microbiology* 145(12):3353–63 (1999). Thus chitinase polypeptides inherently have "chitinase activity."

"Chitinase nucleic acids" or "chitinase polynucleotide sequences" also include polynucleotides of at least about 10, or about 15, or about 20, or about 30, or about 50, or about 100 nucleotides in length that encode subsequences of the above-described chitinase polypeptides (e.g., even numbered sequences from SEQ ID NO: 4 to SEQ ID NO:16 and SEQ ID NO:22 to SEQ ID NO:66) that are not comprised in SEQ ID NO:2, SEQ ID NO:17, SEQ ID NO:18, SEQ ID NO:19 or SEQ ID NO:20. Chitinase polynucleotides are typically less than about 10,000 nucleotides, sometimes less than 5,000 nucleotides and sometimes less than 1,000 or 500 or 100 nucleotides in length.

Some chitinases of the invention exhibit improved chitinase activity as compared to the chitinase displayed in SEQ ID NO:1 or SEQ ID NO:2, in the assays described herein. A typical chitinase enzymatic assay consists of measuring the hydrolysis of carboxymethyl-chitin-remazol brilliant violet, as described herein. See, e.g., Wirth and Wolf, *J. Microbiol. Methods* 12:197–205 (1990). Some chitinases of the invention exhibit an improvement of chitinase activity at least about 150% of the chitinase activity of SEQ ID NO:1, more typically at least 200% of the activity of SEQ ID NO:1, sometimes at least about 500% of the activity of SEQ ID NO:1, sometimes at least 1,000% of activity of SEQ ID NO:1, and sometimes at least 10,000% of the activity of SEQ ID NO:1.

Other chitinase polypeptides of the invention have the same chitinase activity as or lower chitinase activity than SEQ ID NO:1. Typically, these chitinases of the invention exhibit substantially the same activity as SEQ ID NO:1. The polypeptides of the invention, however, can exhibit less than 70%, sometimes less than 50% and even less than 20% or less than 10% of the activity of SEQ ID NO:1.

In the case of both expression of transgenes and inhibition of endogenous genes (e.g., by antisense, or co-suppression) one of skill will recognize that the inserted polynucleotide sequence need not be identical, but may be only "substantially identical" to a sequence of the gene from which it was derived. As explained below, these substantially identical variants are specifically covered by the term "chitinase nucleic acid."

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "chitinase nucleic acid," "chitinase polynucleotide" and their equivalents. In addition, the terms specifically include those full length sequences substantially identical and/or substantially similar (determined as described below) to a chitinase polynucleotide sequence and that encode proteins that retain the function of the chitinase polypeptide (e.g., resulting from conservative substitutions of amino acids in the chitinase polypeptide).

As used herein, an "antibody" refers to a protein consisting of one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv) antibodies in which a variable heavy and a variable light chain are joined together (directly or through a peptide linker) to form a continuous polypeptide.

The phrase "specifically (or selectively) binds" to a polypeptide or "specifically (or selectively) immunoreactive with," when referring to an antibody, refers to a binding reaction that is determinative of the presence of the polypeptide in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a particular chitinase polypeptide of the invention can be selected to obtain only those polyclonal antibodies that are specifically immunoreactive with the polypeptide, and not with other proteins (e.g., SEQ ID NO:2, SEQ ID NO:17, SEQ ID NO:18, SEQ ID NO:19, or SEQ ID NO:20). This selection may be achieved by subtracting out antibodies that cross-react with other proteins. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background. Antibodies that react only with a particular chitinase polypeptide of the invention, e.g., SEQ ID NO:4, SEQ ID NO:6, SEQ ID NO:8, SEQ ID NO:10, SEQ ID NO:12, SEQ ID NO:14, SEQ ID NO:16, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64 or SEQ ID NO:66 can also be made as described above, by subtracting out antibodies that bind to other chitinase proteins. For example, in a competitive binding assay between a polypeptide of the invention and a second polypeptide (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:18, SEQ ID NO:19, or SEQ ID NO:20), it will require at least ten times the amount of the polypeptide of the invention for the second polypeptide to inhibit 50% of the binding to the polypeptide of the invention.

Two nucleic acid sequences or polypeptides are said to be "identical" if the sequence of nucleotides or amino acid residues, respectively, in the two sequences is the same when aligned for maximum correspondence as described below. The terms "identical" or "percent identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA). The term "absolute percent identity" refers to a percentage of sequence identity determined by scoring identical amino acids as 1 and any substitution as zero, regardless of the similarity of mismatched amino acids. In a typical sequence alignment, e.g., a BLAST alignment, the "absolute percent identity" of two sequences is presented as a percentage of amino acid "identities." As used herein, where a sequence is defined as being "at least X % identical" to a reference sequence, e.g., "a polypeptide at least 90% identical to SEQ ID NO:4," it is to be understood that "X % identical" refers to absolute percent identity, unless otherwise indicated. In cases where an optimal alignment of two sequences requires the insertion of a gap in one or both of the sequences, an amino acid residue in one sequence that aligns with a gap in the other sequence is counted as a mismatch for purposes of determining percent identity. Gaps can be internal or external, i.e., a truncation.

The term "substantial identity" of polynucleotide sequences means that a polynucleotide comprises a sequence that has at least 25% sequence identity. Alternatively, percent identity can be any integer from at least 25% to 100% (e.g., at least 25%, 26%, 27%, 28%, ..., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%). Some embodiments include at least: 25%, 30%, 35%, 40%, 45%, 50%, 55%, 60%, 65%, 70%, 75%, 80%, 85%, 90%, 95%, or 99% identity compared to a reference sequence using the programs described herein; preferably BLAST using standard parameters, as described below. The present invention provides for polynucleotides that are at least substantially identical to SEQ ID NOS:3, 5, 7, 9, 11, 13, 15, 21, 23, 25, 27, 29, 31, 33, 35, 37, 39, 41, 43, 45, 47, 49, 51, 53, 55, 57, 59, 61, 63 or 65. One of skill will recognize that these values can be appropriately adjusted to determine corresponding identity of proteins encoded by two nucleotide sequences by taking into account codon degeneracy, amino acid similarity, reading frame positioning and the like.

"Substantial identity" of amino acid sequences for these purposes normally means sequence identity of at least 40%. The percent identity of polypeptides can be any integer from at least 40% to 100% (e.g., at least 40%, 41%, 42%, 43%, ..., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%). Some embodiments include at least 60%, 65%, 70%, 75%, 80%, 85%, 90%, 95%, or 99% identity. The present invention provides for polypeptides that are at least substantially identical to SEQ ID NOS:4, 6, 8, 10, 12, 14, 16, 22, 24, 26, 28, 30, 32, 34, 36, 38, 40, 42, 44, 46, 48, 50, 52, 54, 56, 58, 60, 62, 64 or 66.

Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Examples of conservative amino acid substitution groups are: valine-leucine-isoleucine, phenylalanine-tyrosine, lysine-arginine, alanine-valine, aspartic acid-glutamic acid, and asparagine-glutamine.

The invention provides chitinase amino acid sequences that are "substantially similar" to any of SEQ ID NOS:4, 6, 8, 10, 12, 14, 16, 22, 24, 26, 28, 30, 32, 34, 36, 38, 40, 42, 44, 46, 48, 50, 52, 54, 56, 58, 60, 62, 64 or 66, as well as polynucleotides encoding these amino acid sequences. "Substantial similarity" of chitinase amino acid sequences can be determined by determining a similarity score for the two sequences. As used herein, the "similarity score" refers to the score generated for the two sequences using the BLOSUM62 amino acid substitution matrix, a gap existence penalty of 11, and a gap extension penalty of 1, when the two sequences are optimally aligned. Two sequences are "optimally aligned" when they are aligned so as to produce the maximum possible score for that pair of sequences, which might require the introduction of gaps in one or both of the sequences to achieve that maximum score. Two chitinase amino acid sequences are substantially similar if their similarity score exceeds a certain threshold value. The threshold value can be any integer ranging from at least 1190 to the highest possible score for a particular reference chitinase sequence (e.g., about 1500 for SEQ ID NO:18). For example, the threshold similarity score can be 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, or higher. If in a particular embodiment of the invention the threshold score is set at, for example, 1300, and the reference chitinase sequence is SEQ ID NO:4, then any chitinase amino acid sequence that can be optimally aligned with SEQ ID NO:4 to generate a similarity score of greater than 1300 is "substantially similar" to SEQ ID NO:4.

Amino acid substitution matrices and their use in quantifying the similarity between two sequences are well-known in the art and described, e.g., in Dayhoff et al. (1978), "A model of evolutionary change in proteins", "Atlas of Protein Sequence and Structure," Vol. 5, Suppl. 3 (ed. M. O. Dayhoff), pp. 345–352. Natl. Biomed. Res. Found., Washington, D.C. and in Henikoff et al. (1992) Proc. Natl. Acad. Sci. USA 89:10915–10919. A high similarity generally correlates with homology of the sequences. The BLOSUM62 matrix is often used as a default scoring substitution matrix in sequence alignment protocols such as Gapped BLAST 2.0. The gap existence penalty is imposed for opening gap in one of the aligned sequences, and the gap extension penalty is imposed for each amino acid position in the gap. Thus, a two amino acid residue gap will result in a penalty of 13, 11 for existence of the gap and 2 for extending the gap two amino acids. The alignment is defined by the amino acid positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al., (1997) Nucleic Acids Res. 25:3389–3402, and made available to the public at the National Center for Biotechnology Information website. To generate accurate similarity scores using NCBI BLAST, it is important to turn off any filtering, e.g., low complexity filtering, and to disable the use of composition based statistics. One should also confirm that the correct substitution matrix and gap penalties are used. Optimal alignments, including multiple alignments, can be prepared using, e.g., PSI-BLAST, available through the NCBI internet site and described by Altschul et al., (1997) Nucleic Acids Res. 25:3389–3402. One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. When a "comparison window" is used to determine the percent identity between two sequences, a lower limit on the length of the comparison window can be imposed, e.g., a minimum length of 20, 30, 40, 50, 60, 70, 80, 90, 100, 110, 120, 130, 140, 150, 160, 170, 180, 190, 200, 210, 220, 230, 240 or 250 amino acids. Alternatively, percent identity can be defined such that the window of comparison over which the percent identity criterion is satisfied must include a sufficient amount of the reference sequence to possess some chitinase activity. Thus, if two sequences satisfy a minimum percent identity criterion (e.g., at least 90% sequence identity) only over a window of comparison that is less than the entire length of the amino acid sequence used as a reference (e.g., SEQ ID NO: 4), then the subsequence of the reference sequence corresponding to the window of comparison must itself have chitinase activity in order to conclude that the two sequences meet the percent identity criterion. For example, if two sequences only share X percent identity over a short window of comparison (e.g., 20 contiguous amino acids), and that 20 contiguous amino acids is not sufficient unto itself to possess chitinase activity (which would normally be the case), then the two sequences do not satisfy the criterion of possessing at least X percent identity. Alternatively, if the window of comparison spans a longer subsequence of contiguous amino acids that possesses chitinase activity even without the rest of the sequence, the criterion will be found to have been met.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).
  (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). The $T_m$ (thermal melting point) is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Generally, highly stringent conditions are selected to be about 5–10° C. lower than the $T_m$ for the specific sequence at a defined ionic strength pH. Low stringency conditions are generally selected to be about 15–30° C. below the $T_m$. Hybridization conditions are typically those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. For the purposes of this disclosure, stringent conditions for such RNA-DNA hybridizations are those which include at least one wash in 0.2×SSC at 63° C. for 20 minutes, or equivalent conditions. Genomic DNA or cDNA comprising genes of the invention can be identified using the polynucleotides explicitly disclosed herein (e.g., odd numbered SEQ ID NO:s from 3–15 and 21–65), or fragments thereof of at least about 100 nucleotides, under stringent hybridization conditions. Stringent hybridization conditions, for purposes of this disclosure, include at least one wash (usually 2) in 0.2×SSC at a temperature of at least about 50° C., usually about 55° C., and sometimes 60° C. or 65° C., for 20 minutes, or equivalent conditions.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

In the present invention, genomic DNA or cDNA comprising chitinase nucleic acids of the invention can also be identified in standard Southern blots under stringent conditions using the nucleic acid sequences disclosed herein. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

BRIEF DESCRIPTION OF THE DRAWINGS

FIG. 1 illustrates the inhibition of *Fusarium moniliforme* hyphal growth in the presence of purified chitinases (Chitinase A (SEQ ID NO: 1) and r2C2 (SEQ ID NO: 12)).

FIG. 2 illustrates a comparative nucleotide alignment between the gene sequence encoding Chitinase A (SEQ ID NO:1) and a selection of the polynucleotides of the invention (r1B6 (SEQ ID NO: 3), r1B10 (SEQ ID NO: 5), r1D4 (SEQ ID NO: 7), r2A2 (SEQ ID NO: 9), r2C2 (SEQ ID NO: 11), r2E1 (SEQ ID NO: 13), and r2H2 (SEQ ID NO: 15).

FIG. 3 illustrates a comparative amino acid alignment between Chitinase A (SEQ ID NO:1) and a selection of the gene products of the invention (r1B6 (SEQ ID NO: 4), r1B10 (SEQ ID NO: 6), r1D4 (SEQ ID NO: 8), r2A2 (SEQ ID NO: 10), r2C2 (SEQ ID NO: 12), r2E1 (SEQ ID NO: 14), and r2H2 (SEQ ID NO: 16).

FIG. 4 illustrates the antifungal activity of some identified chitinases. Purified chitinases were added to germinating spores of *Fusarium moniliforme* and their efficiency at inhibiting fungal growth was recorded by taking absorbance measurements at 600 nm. (A) The average concentration of chitinase required to inhibit fungal growth by 50% is reported. (B) Improvement of clones 4M1/1_H2 (SEQ ID NO: 24), 4M1/11_C10 (SEQ ID NO: 22), and 4M1/26_C2 (SEQ ID NO: 26) as compared to "hit" r2C2 (SEQ ID NO: 12) is reported.

FIG. 6 illustrates a comparative nucleotide alignment between a selection of the polynucleotides of the invention (4M1/1_H2 (SEQ ID NO: 23), 4M1/11_C10 (SEQ ID NO: 21), and 4M1/26_C2 (SEQ ID NO: 25).

FIG. 7 illustrates a comparative amino acid alignment between a selection of the gene products of the invention (4M1/1_H2 (SEQ ID NO: 24), 4M1/11_C10 (SEQ ID NO: 22), and 4M1/26_C2 (SEQ ID NO: 26).

FIG. 11 a comparative nucleotide alignment between the gene sequence encoding Chitinase A (SEQ ID NO:1) and a selection of the polynucleotides of the invention (r1AB2 (SEQ ID NO: 27), r1AD4 (SEQ ID NO: 29), r1AD6 (SEQ ID NO: 31), r1AG9 (SEQ ID NO: 33), r1AH8 (SEQ ID NO: 35), r1AH9 (SEQ ID NO: 37), r1BG5 (SEQ ID NO: 39), r2C5 (SEQ ID NO: 41), 4N1/95_H3 (SEQ ID NO: 43), 4N1/80_F8 (SEQ ID NO: 45), 4N1/75_D3 (SEQ ID NO: 47), 4N1/2_H9 (SEQ ID NO: 49), 4N1/23_G4 (SEQ ID NO: 51), 4N1/68_E4 (SEQ ID NO: 53), 4N1/88_F9 (SEQ ID NO: 55), 4N1/14_B3 (SEQ ID NO: 57), 4N1/33_F4 (SEQ ID NO: 59), 4N1/11_B11 (SEQ ID NO: 61), 4N1/30_D3 (SEQ ID NO; 63), and 4N1/35_G5(SEQ ID NO: 65)).

FIG. 12 illustrates a comparative amino acid alignment between Chitinase A (SEQ ID NO:1) and a selection of the gene products of the invention. (r1AB2 (SEQ ID NO: 28), r1AD4 (SEQ ID NO: 30), r1AD6 (SEQ ID NO: 32), r1AG9 (SEQ ID NO: 34), r1AH8 (SEQ ID NO: 36), r1AH9 (SEQ ID NO: 38), r1BG5 (SEQ ID NO: 40), r2C5 (SEQ ID NO: 42), 4N1/95_H3 (SEQ ID NO: 44), 4N1/80_F8 (SEQ ID NO: 46), 4N1/75_D3 (SEQ ID NO: 48), 4N1/2_H9 (SEQ ID NO: 50), 4N1/23_G4 (SEQ ID NO: 52), 4N1/68_E4 (SEQ ID NO: 54), 4N1/88_F9 (SEQ ID NO: 56), 4N1/14_B3 (SEQ ID NO: 58), 4N1/33_F4 (SEQ ID NO: 60), 4N1/11_B11 (SEQ ID NO: 62), 4N1/30_D3 (SEQ ID NO; 64), and 4N1/35_G5(SEQ ID NO: 66)).

DESCRIPTION OF THE SPECIFIC EMBODIMENTS

Figure 5:
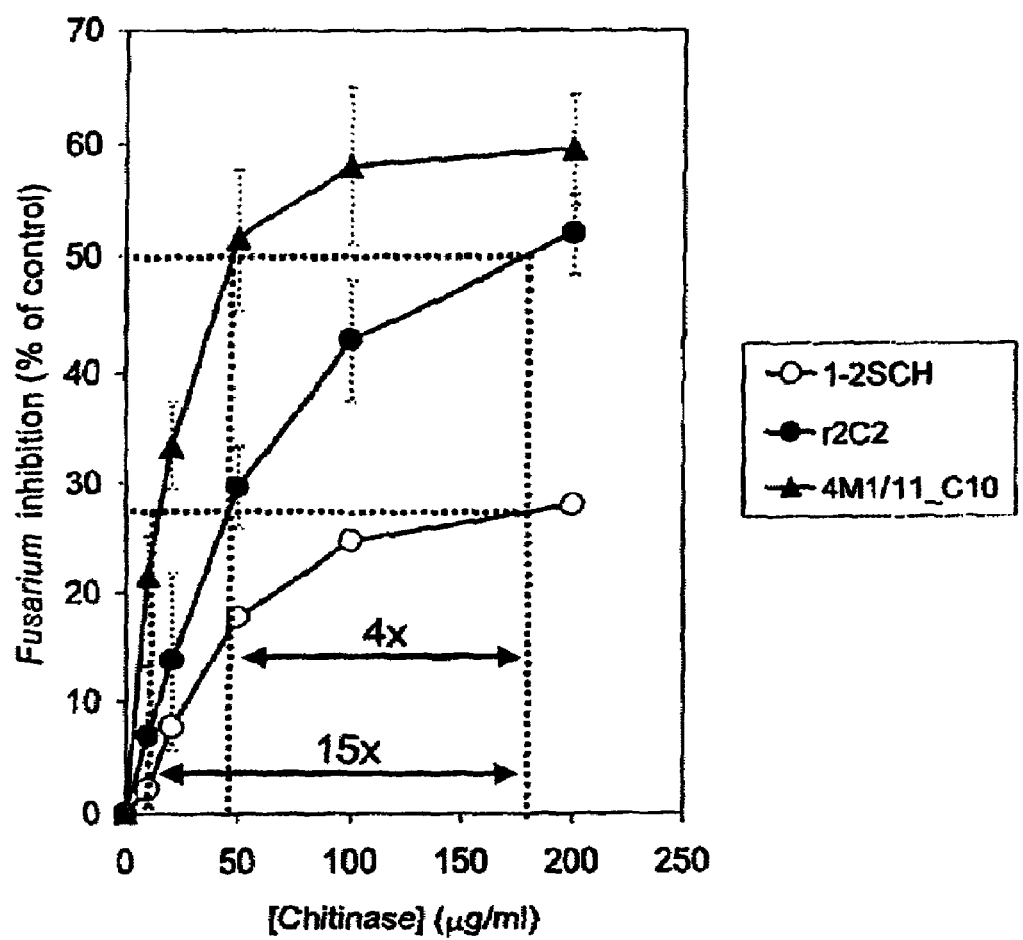
FIG. 5 illustrates antifungal activity of variant 4M1/11_C10 (SEQ ID NO: 22), as compared to the wild-type protein Chitinase A (labeled "1-2SCH" in the figure) and variant "r2C2" (SEQ ID NO: 12).

The present invention provides chitinase polypeptides, some of which possess improved enzymatic activity, i.e., increased activity compared to the activity of the maize chitinase A (SEQ ID NO:1). The invention also provides methods of improving plant resistance to fungal pathogens and other pests, such as insects. In particular, resistance to pests can be enhanced by introducing into plants a polynucleotide encoding a chitinase polypeptide of the invention.

The combination of alterations in the polypeptides of the invention result in a variety of levels of enzymatic activity. Thus, combinations of different alterations, which individually provide positive or negative effects, result in the ultimate variation in activity found in the polypeptides. For example, combinations of positive and negative (i.e., inhibitory) alterations can lead to improved activity over wild type chitinase activity. In some cases, it is possible that alterations that produce a negative effect when added singly can have a positive, synergistic effect when combined with other alterations.

Polypeptides of the Invention

Polypeptides of the invention are related to the polypeptides exemplified in SEQ ID NO:4, SEQ ID NO:6, SEQ ID NO:8, SEQ ID NO:10, SEQ ID NO:12, SEQ ID NO:14, SEQ ID NO:16 and SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64 or SEQ ID NO:66. In some cases polypeptides of the invention exhibit improved chitinase activity compared to that of the maize chitinase A proteins, in accordance with the activity assays described herein.

The amino acid sequences of the polypeptides of the invention comprise at least one amino acid difference from SEQ ID NO:1, SEQ ID NO:2, SEQ ID NO:17, SEQ ID NO:18, SEQ ID NO:19 or SEQ ID NO:20. The amino acid sequences of the chitinases exemplified in the application (e.g., even numbered sequences from 4 to 16 and 22–66) each have improved activity over maize Chitinases A (SEQ ID NO:1). Therefore, chitinases comprising some or all of the differences between the exemplified sequences and Chitinase A are likely to increase enzymatic activity of a chitinase polypeptide.

Polypeptides of the invention can optionally encompass a signal sequence to target the polypeptides of the invention to a particular organelle or compartment of the cell.

Purification of Chitinase Polypeptides

Either naturally occurring or recombinant chitinase polypeptides can be purified for use in functional assays. Naturally occurring chitinase polypeptides can be purified, e.g., from plant tissue and any other source of a chitinase. Recombinant chitinase polypeptides can be purified from any suitable expression system.

The chitinase polypeptides may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)(Ausubel et al.)).

A number of procedures can be employed when recombinant chitinase polypeptides are being purified. For example, proteins having established molecular adhesion properties can be reversibly fused to the chitinase polypeptides. With the appropriate ligand, the chitinase polypeptides can be selectively adsorbed to a purification column and then freed from the column in a relatively pure form. The fused protein can then be removed by enzymatic activity. Finally the chitinase polypeptides could be purified using immunoaffinity columns.

Cross-Reactivity Determinations

Immunoassays in a competitive binding format can be used to identify polypeptide sequences with cross reactivity to an antibody raised to a particular polypeptide or epitope of the invention. For example, a protein at least partially encoded by an odd numbered sequence between SEQ ID NO:3 and SEQ ID NO:15 or SEQ ID NO:21 and SEQ ID NO:65, or an immunogenic region thereof, can be immobilized to a solid support. Other competitor proteins such as SEQ ID NO:2, SEQ ID NO:17, SEQ ID NO:18 or maize chitinases A and B described in Huynh, et al., *J. Biol. Chem.* 267:6635–6640 (1992) (SEQ ID NO:19 or SEQ ID NO:20) or modifications or fragments thereof, can be added to the assay so as to compete for binding of the antisera to the immobilized antigen. In some cases, at least one protein as displayed in even-number sequences between SEQ ID NO:4 and SEQ ID NO:16 is used as a competitor protein. The ability of the added proteins to compete for binding of the antisera to the immobilized protein is compared to the ability of the particular polypeptide of the invention (e.g., even-numbered sequences from SEQ ID NO:22 to SEQ ID NO:66) to compete with itself. The percent cross-reactivity for the above proteins is calculated, using standard calculations. Those antisera with less than 10% cross-reactivity with each of the added competitor proteins listed above are selected and pooled. The cross-reacting antibodies are optionally removed from the pooled antisera by immunoabsorption with the added considered competitor proteins, e.g., distantly related homologs, or other homologs of the polypeptide of the invention (e.g., SEQ ID NO:1, SEQ ID NO:2 (see, e.g., PCT WO 00/56908), SEQ ID NO:17 (Genbank Accession No. M84164) and SEQ ID NO:18 (Genbank Accession No. M84165), SEQ ID NO:19 and SEQ ID NO:20 (see, e.g., Huynh, et al., *J. Biol. Chem.* 267:6635–6640 (1992)).

The immunoabsorbed and pooled antisera are then used in a competitive binding immunoassay as described below to compare a second protein, thought to be perhaps an allele or polymorphic variant of the particular chitinase, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the chitinase polypeptide of the invention that is required to inhibit 50% of binding, then the second protein is said to specifically bind to the polyclonal antibodies generated to the respective chitinase immunogen.

Competitive Immunoassay Formats

In competitive assays, the amount of the chitinase present in the sample is measured indirectly by measuring the amount of known, added (exogenous) chitinase displaced (competed away) from an anti-chitinase antibody by the unknown chitinase present in a sample. In one competitive assay, a known amount of the chitinase is added to a sample and the sample is then contacted with an antibody that specifically binds to the chitinase. The amount of exogenous chitinase bound to the antibody is inversely proportional to the concentration of the chitinase present in the sample. In a particularly preferred embodiment, the antibody is immobilized on a solid substrate. The amount of chitinase bound to the antibody may be determined either by measuring the amount of chitinase present in a chitinase/antibody complex, or alternatively by measuring the amount of remaining uncomplexed protein. The amount of chitinase may be detected by providing a labeled chitinase molecule.

A hapten inhibition assay is another preferred competitive assay. In this assay the known chitinase is immobilized on a solid substrate. A known amount of anti-chitinase antibody is added to the sample, and the sample is then contacted with the immobilized chitinase. The amount of anti-chitinase antibody bound to the known immobilized chitinase is inversely proportional to the amount of chitinase present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Chitinase Nucleic Acids

Nucleic acids of the invention generally comprise all or part of a polynucleotide encoding a chitinase polypeptide of the invention.

Nucleic acids of the invention also encompass nucleic acid probes. Probes are useful, for instance, to detect differences between maize chitinase genes A and B (SEQ ID NOs: 1 and 2) and polynucleotides encoding alterations in the maize chitinase A and B sequences that give rise to improved or altered enzymatic activity. Such alterations can result from, e.g., insertions, deletions or point mutations. In some embodiments, the alterations are linear combinations of SEQ ID NO:1 and SEQ ID NO:2. Probes can be of any length useful to detect a desired polynucleotide.

In one aspect of the invention, probes are designed to bind to the polynucleotides of the invention at sequences comprised of fusions of subsequences of SEQ ID NO:1 and SEQ ID NO:2. For example, nucleotides 498 to 776 of SEQ ID NO:3 comprises nucleotides 613 to 767 of SEQ ID NO:1 and nucleotides 468 to 594 of SEQ ID NO:2. For example, those of skill in the art will recognize that probes can be designed to selectively hybridize to a polynucleotide encoding the polypeptides or polypeptide subsequences of the invention but not hybridize to the native maize Chitinase A or B polynucleotide sequences (SEQ ID NO:s 1 and 2) or SEQ ID NO:s 17 or 18.

Chitinases or enzymatically functional equivalents thereof can be constructed synthetically by using the polymerase chain reaction (PCR), either independently of the cloning vector used (Dillon, et al. *BioTechniques* 9:298–300 (1990); Sandhu, et al. *BioTechniques* 12:12–16 (1992)) or by direct cloning into a vector (Ivanov, et al. *Gene* 95:295–299 (1990); Foguet, et al. *BioTechniques* 13:674–675 (1992)). Alternatively, complete genes can be constructed from synthetic PCR fragments or duplex oligonucleotides through in-frame cloning (Pierce, J. C. *Methods Mol. Biol.* 67:151–65 (1997)).

Chitinase polynucleotides of the invention can be readily modified using methods that are well known in the art to improve or alter chitinase activity. A variety of diversity generating protocols are available and described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, nucleic acid libraries) which are useful, for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids that encode proteins with or which confer desirable properties. Following diversification by one or more of the methods herein, or otherwise available to one of skill, any nucleic acids that are produced can be selected for a desired activity or property, e.g. chitinase activity. This can include identifying any activity that can be detected, for example, in an automated or automatable format, by any of the assays in the art, for example, by assaying the hydrolysis of carboxymethyl-chitin-remazol brilliant violet, as described herein. A variety of related (or even unrelated) properties can be evaluated, in serial or in parallel, at the discretion of the practitioner.

Descriptions of a variety of diversity generating procedures for generating modified chitinase nucleic acid sequences of the invention are found in the following publications and the references cited therein: Stemmer, et al. (1999) "Molecular breeding of viruses for targeting and other clinical properties" *Tumor Targeting* 4:1–4; Ness et al. (1999) "DNA Shuffling of subgenomic sequences of subtilisin" *Nature Biotechnology* 17:893–896; Chang et al. (1999) "Evolution of a cytokine using DNA family shuffling" *Nature Biotechnology* 17:793–797; Minshull and Stemmer (1999) "Protein evolution by molecular breeding" *Current Opinion in Chemical Biology* 3:284–290; Christians et al. (1999) "Directed evolution of thymidine kinase for AZT phosphorylation using DNA family shuffling" *Nature Biotechnology* 17:259–264; Crameri et al. (1998) "DNA shuffling of a family of genes from diverse species accelerates directed evolution" *Nature* 391:288–291; Crameri et al. (1997) "Molecular evolution of an arsenate detoxification pathway by DNA shuffling," *Nature Biotechnology* 15:436–438; Zhang et al. (1997) "Directed evolution of an effective fucosidase from a galactosidase by DNA shuffling and screening" *Proc. Natl. Acad. Sci. USA* 94:4504–4509; Patten et al. (1997) "Applications of DNA Shuffling to Pharmaceuticals and Vaccines" *Current Opinion in Biotechnology* 8:724–733; Crameri et al. (1996) "Construction and evolution of antibody-phage libraries by DNA shuffling" *Nature Medicine* 2:100–103; Crameri et al. (1996) "Improved green fluorescent protein by molecular evolution using DNA shuffling" *Nature Biotechnology* 14:315–319; Gates et al. (1996) "Affinity selective isolation of ligands from peptide libraries through display on a lac repressor 'headpiece dimer'" *Journal of Molecular Biology* 255: 373–386; Stemmer (1996) "Sexual PCR and Assembly PCR" In: *The Encyclopedia of Molecular Biology*. VCH Publishers, New York. pp. 447–457; Crameri and Stemmer (1995) "Combinatorial multiple cassette mutagenesis creates all the permutations of mutant and wildtype cassettes" *BioTechniques* 18:194–195; Stemmer et al., (1995) "Single-step assembly of a gene and entire plasmid form large numbers of oligodeoxy-ribonucleotides" *Gene,* 164:49–53; Stemmer (1995) "The Evolution of Molecular Computation" *Science* 270: 1510; Stemmer (1995) "Searching Sequence Space" *Bio/Technology* 13:549–553; Stemmer (1994) "Rapid evolution of a protein in vitro by DNA shuffling" *Nature* 370:389–391; and Stemmer (1994) "DNA shuffling by random fragmentation and reassembly: In vitro recombination for molecular evolution." *Proc. Natl. Acad. Sci. USA* 91:10747–10751.

Mutational methods of generating diversity include, for example, site-directed mutagenesis (Ling et al. (1997) "Approaches to DNA mutagenesis: an overview" *Anal. Biochem.* 254(2): 157–178; Dale et al. (1996) "Oligonucleotide-directed random mutagenesis using the phosphorothioate method" *Methods Mol. Biol.* 57:369–374; Smith (1985) "In vitro mutagenesis" *Ann. Rev. Genet.* 19:423–462; Botstein & Shortle (1985) "Strategies and applications of in vitro mutagenesis" *Science* 229:1193–1201; Carter (1986) "Site-directed mutagenesis" *Biochem. J.* 237:1–7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488–492; Kunkel et al. (1987) "Rapid and efficient site-specific mutagenesis without phenotypic selection" *Methods in Enzymol.* 154, 367–382; Bass et al. (1988) "Mutant Trp repressors with new DNA-binding specificities" *Science* 249:240–245); oligonucleotide-directed mutagenesis (*Methods in Enzymol.* 100: 468–500 (1983); *Methods in Enzymol.* 154: 329–350 (1987); Zoller & Smith (1982) "Oligonucleotide-directed mutagenesis using M13-derived vectors: an efficient and general procedure for the production of point mutations in any DNA fragment" *Nucleic Acids Res.* 10:6487–6500; Zoller & Smith (1983) "Oligonucleotide-directed mutagenesis of DNA fragments cloned into M13 vectors" *Methods in Enzymol.* 100:468–500; and Zoller & Smith (1987) "Oligonucleotide-directed mutagenesis: a simple method using two oligonucleotide primers and a single-stranded DNA template" *Methods in Enzymol.* 154:329–350); phosphorothioate-modified DNA mutagenesis (Taylor et al. (1985) "The use of phosphorothioate-modified DNA in restriction enzyme reactions to prepare nicked DNA" *Nucl. Acids Res.* 13: 8749–8764; Taylor et al. (1985) "The rapid generation of oligonucleotide-directed mutations at high frequency using phosphorothioate-modified DNA" *Nucl. Acids Res.* 13: 8765–8787 (1985); Nakamaye & Eckstein (1986) "Inhibition of restriction endonuclease Nci I cleavage by phosphorothioate groups and its application to oligonucleotide-directed mutagenesis" *Nucl. Acids Res.* 14: 9679–9698; Sayers et al. (1988) "Y-T Exonucleases in phosphorothioate-based oligonucleotide-directed mutagenesis" *Nucl. Acids Res.* 16:791–802; and Sayers et al. (1988) "Strand specific cleavage of phosphorothioate-containing DNA by reaction with restriction endonucleases in the presence of ethidium bromide" *Nucl. Acids Res.* 16: 803–814); mutagenesis using gapped duplex DNA (Kramer et al. (1984) "The gapped duplex DNA approach to oligonucleotide-directed mutation construction" *Nucl. Acids Res.* 12: 9441–9456; Kramer & Fritz (1987) *Methods in Enzymol.* "Oligonucleotide-directed construction of mutations via gapped duplex DNA" 154: 350–367; Kramer et al. (1988) "Improved enzymatic in vitro reactions in the gapped duplex DNA approach to oligonucleotide-directed construction of mutations" *Nucl. Acids Res.* 16: 7207; and Fritz et al. (1988) "Oligonucleotide-directed construction of mutations: a gapped duplex DNA procedure without enzymatic reactions in vitro" *Nucl. Acids Res.* 16: 6987–6999).

Additional suitable methods include point mismatch repair (Kramer et al. (1984) "Point Mismatch Repair" *Cell* 38:879–887), mutagenesis using repair-deficient host strains (Carter et al. (1985) "Improved oligonucleotide site-directed mutagenesis using M13 vectors" *Nucl. Acids Res.* 13: 4431–4443; and Carter (1987) "Improved oligonucleotide-directed mutagenesis using M13 vectors" *Methods in Enzymol.* 154: 382–403), deletion mutagenesis (Eghtedarzadeh & Henikoff(1986) "Use of oligonucleotides to generate large deletions" *Nucl. Acids Res.* 14: 5115), restriction-selection and restriction-selection and restriction-purification (Wells et al. (1986) "Importance of hydrogen-bond formation in stabilizing the transition state of subtilisin" *Phil. Trans. R. Soc. Lond. A* 317: 415–423), mutagenesis by total gene synthesis (Nambiar et al. (1984) "Total synthesis and cloning of a gene coding for the ribonuclease S protein" *Science* 223: 1299–1301; Sakamar and Khorana (1988) "Total synthesis and expression of a gene for the a-subunit of bovine rod outer segment guanine nucleotide-binding protein (transducin)" *Nucl. Acids Res.* 14: 6361–6372; Wells et al. (1985) "Cassette mutagenesis: an efficient method for generation of multiple mutations at defined sites" *Gene* 34:315–323; and Grundström et al. (1985) "Oligonucleotide-directed mutagenesis by microscale 'shot-gun' gene synthesis" *Nucl. Acids Res.* 13: 3305–3316), double-strand break repair (Mandecki (1986); Arnold (1993) "Protein engineering for unusual environments" *Current Opinion in Biotechnology* 4:450–455. "Oligonucleotide-directed double-strand break repair in plasmids of *Escherichia coli*: a method for site-specific mutagenesis" *Proc. Natl. Acad. Sci. USA*, 83:7177–7181). Additional details on many of the above methods can be found in *Methods in Enzymology* Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library,"

WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding various diversity generating methods, including "Shuffling of Codon Altered Genes" by Patten et al. filed Sep. 28, 1999, (U.S. Ser. No. 09/407,800); "Evolution of Whole Cells and Organisms by Recursive Sequence Recombination", by del Cardayre et al. filed Jul. 15, 1998 (U.S. Ser. No. 09/166,188), and Jul. 15, 1999 (U.S. Ser. No. 09/354,922); "Oligonucleotide Mediated Nucleic Acid Recombination" by Crameri et al., filed Sep. 28, 1999 (U.S. Ser. No. 09/408,392), and "Oligonucleotide Mediated Nucleic Acid Recombination" by Crameri et al., filed Jan. 18, 2000 (PCT/US00/01203); "Use of Codon-Based Oligonucleotide Synthesis for Synthetic Shuffling" by Welch et al., filed Sep. 28, 1999 (U.S. Ser. No. 09/408,393); "Methods for Making Character Strings, Polynucleotides & Polypeptides Having Desired Characteristics" by Selifonov et al., filed Jan. 18, 2000, (PCT/US00/01202) and, e.g., "Methods for Making Character Strings, Polynucleotides & Polypeptides Having Desired Characteristics" by Selifonov et al., filed Jul. 18, 2000 (U.S. Ser. No. 09/618,579); "Methods of Populating Data Structures for Use in Evolutionary Simulations" by Selifonov and Stemmer (USSN PCT/US00/01138), filed Jan. 18, 2000; and "Single-Stranded Nucleic Acid Template-Mediated Recombination and Nucleic Acid Fragment Isolation" by Affholter, USSN. 60/186,482, filed Mar. 2, 2000.

In brief, several different general classes of sequence modification methods, such as mutation, recombination, etc. are applicable to the present invention and set forth in the references above. Accordingly, the chitinase nucleic acids of the invention can be generated from wild type sequences. Moreover, the chitinase nucleic acid sequences of the invention can be modified to create modified sequences with the same or different activity.

The following illustrate some exemplary formats for diversity generation in the context of the present invention, in including, certain recombination based diversity generation formats.

Nucleic acids can be recombined in vitro by any of a variety of techniques discussed in the references above, including, DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described in several of the references above, such as, in Stemmer (1994) *Proc. Natl. Acad. Sci. USA* 91:10747–10751. Thus, nucleic acids encoding chitinase with modified activity can be generated.

Similarly, nucleic acids can be recursively recombined in vivo by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above.

Whole genome recombination methods can also be used in which whole genomes of cells or other organisms are recombined, optionally including spiking of the genomic recombination mixtures with desired library components (for example, genes corresponding to the pathways of the present invention). These methods have many applications, including those in which the identity of a target gene is not known. Details on such methods are found in WO 98/31837 by del Cardayre et al. "Evolution of Whole Cells and Organisms by Recursive Sequence Recombination;" and in PCT/US99/15972 by del Cardayre et al., also entitled "Evolution of Whole Cells and Organisms by Recursive Sequence Recombination."

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods or can be made by tri-nucleotide synthetic approaches. Details regarding such approaches are found in the references noted above, including, "Oligonucleotide Mediated Nucleic Acid Recombination" by Crameri et al., filed Sep. 28, 1999 (U.S. Ser. No. 09/408,392), and "Oligonucleotide Mediated Nucleic Acid Recombination" by Crameri et al., filed Jan. 18, 2000 (PCT/US00/01203); "Use of Codon-Based Oligonucleotide Synthesis for Synthetic Shuffling" by Welch et al., filed Sep. 28, 1999 (U.S. Ser. No. 09/408,393); "Methods for Making Character Strings, Polynucleotides & Polypeptides Having Desired Characteristics" by Selifonov et al., filed Jan. 18, 2000, (PCT/US00/01202); "Methods of Populating Data Structures for Use in Evolutionary Simulations" by Selifonov and Stemmer (PCT/US00/01138), filed Jan. 18, 2000; and, e.g., "Methods for Making Character Strings, Polynucleotides & Polypeptides Having Desired Characteristics" by Selifonov et al., filed Jul. 18, 2000 (U.S. Ser. No. 09/618,579).

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (for example, based on cross-over site selection) as well as designed, pseudo-random or random recombination methods are described in "Methods for Making Character Strings, Polynucleotides & Polypeptides Having Desired Characteristics" by Selifonov et al., filed Jan. 18, 2000, (PCT/US00/01202) "Methods of Populating Data Structures for Use in Evolutionary Simulations" by Selifonov and Stemmer (PCT/US00/01138), filed Jan. 18, 2000; and, e.g., "Methods for Making Character Strings, Polynucleotides & Polypeptides Having Desired Characteristics" by Selifonov et al., filed Jul. 18, 2000 (U.S. Ser. No. 09/618,579). Extensive details regarding in silico recombination methods are found in these applications. This methodology is generally applicable to the present invention in providing for recombination of the chitinase nucleic acids in silico and/or the generation of corresponding nucleic acids or proteins.

Many methods of accessing natural diversity, such as, by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, in "Single-Stranded Nucleic Acid Template-Mediated Recombination and Nucleic Acid Fragment Isolation" by Affholter, USSN 60/186,482, filed Mar. 2, 2000.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library of enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see e.g., U.S. Pat. No. 5,965,408, "Method of DNA reassembly by interrupting synthesis" to Short, and the references above), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) "A combinatorial approach to hybrid enzymes independent of DNA homology" *Nature Biotech* 17:1205. This approach can be used to generate an initial library of variants which can optionally serve as a substrate for one or more in vitro or in vivo recombination methods. See, also, Ostermeier et al. (1999) "Combinatorial Protein Engineering by Incremental Truncation," *Proc. Natl. Acad. Sci. USA*, 96: 3562–67; and Ostermeier et al. (1999), "Incremental Truncation as a Strategy in the Engineering of Novel Biocatalysts," *Biological and Medicinal Chemistry*, 7: 2139–44.

Mutational methods which result in the alteration of individual nucleotides or groups of contiguous or non-contiguous nucleotides can be favorably employed to introduce nucleotide diversity. Thus, modified chitinase nucleic acids of the invention can be generated, including for optimized codon usage for an organism of interest, as well as nucleic acids encoding chitinase polypeptides with improved and/or modified activity. Many mutagenesis methods are found in the above-cited references; and additional details regarding mutagenesis methods can be found in the references discussed below, which can also be applied to the present invention.

For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, in Leung et al. (1989) *Technique* 1:11–15 and Caldwell et al. (1992) *PCR Methods Applic.* 2:28–33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and in Reidhaar-Olson et al. (1988) *Science*, 241:53–57. Similarly, cassette mutagenesis can be used in a process that replaces a small region of a double stranded DNA molecule with a synthetic oligonucleotide cassette that differs from the native sequence. The oligonucleotide can contain, completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) *Proc. Natl. Acad. Sci. USA* 89:7811–7815.

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11:1548–1552.

In vivo mutagenesis can be used to generate random mutations in any cloned DNA of interest by propagating the DNA in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g., a bacterial, fungal, animal or plant genome, can be used in conjunction with the above described and/or referenced methods. For example, in addition to the methods above, techniques have been proposed which produce nucleic acid multimers suitable for transformation into a variety of species (see, for example, Schellenberger U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, such as PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783, 431 "Methods for Generating and Screening Novel Metabolic Pathways," and Thompson, et al. (1998) U.S. Pat. No. 5,824,485 Methods for Generating and Screening Novel Metabolic Pathways) and their use to identify protein activities of interest has been proposed (in addition to the references noted above, see, Short (1999) U.S. Pat. No. 5,958, 672 "Protein Activity Screening of Clones Having DNA from Uncultivated Microorganisms"). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, for example, bacterial species, eukaryotic cells. In some cases, the library is biased by preselecting sequences which encode a protein of interest, or which hybridize to a nucleic acid of interest. Any such libraries can be provided as substrates for any of the methods herein described.

The above described procedures have been largely directed to increasing nucleic acid and/or encoded protein diversity. However, in many cases, not all of the diversity is useful, for example, functional, and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, for example, by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined complementarity determining regions (CDRs) derived from B cell cDNA libraries can be amplified and assembled into framework regions (see, Jirholt et al. (1998) "Exploiting sequence space: shuffling in vivo formed complementarity determining regions into a master framework" *Gene* 215: 471) prior to diversifying according to any of the methods described herein.

Libraries can be biased towards nucleic acids which encode proteins with desirable enzyme activities. For example, after identifying a clone from a library that exhibits a specified activity, the clone can be mutagenized using any known method for introducing DNA alterations. A library comprising the mutagenized homologues is then screened for a desired activity, which can be the same as or different from the initially specified activity. An example of such a procedure is proposed in Short (1999) U.S. Pat. No. 5,939, 250 for "Production of Enzymes Having Desired Activities by Mutagenesis." Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (see, WO 98/58085) that clones with desired activities can be identified by inserting bioactive substrates into samples of the library, and detecting bioactive fluorescence corresponding to the product of a desired activity using a fluorescent analyzer, such as, a flow cytometry device, a charge couple device (CCD), a fluorometer, or a spectrophotometer.

Libraries can also be biased towards nucleic acids which have specified characteristics, for example, hybridization to a selected nucleic acid probe. In particular, application WO 99/10539 proposes that polynucleotides encoding a desired activity (for example, an enzymatic activity, such as, a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in a recombination-based approach that employs a single-stranded template, as described above.

"Non-Stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods can be applied to the present invention as well.

It will readily be appreciated that any of the above described techniques, which are suitable for enriching a library prior to diversification can also be used to screen the products, or libraries of products, produced by the diversity generating methods.

Kits for mutagenesis, library construction and other diversity generation methods are also commercially available. For example, kits are available from, for example, Stratagene (QuickChange™ site-directed mutagenesis kit; and Chameleon™ double-stranded, site-directed mutagenesis kit), Bio/Can Scientific, Bio-Rad (using the Kunkel method described above), Boehringer Mannheim Corp., Clonetech Laboratories, DNA Technologies, Epicentre Technologies (5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (using the Eckstein method above), and Anglian Biotechnology Ltd (using the Carter/Winter method above).

The above references provide many mutational formats, including recombination, recursive recombination, recursive mutation and combinations or recombination with other forms of mutagenesis, as well as many modifications of these formats. Regardless of the diversity generation format that is used, the nucleic acids of the invention can be recombined (with each other, or with related (or even unrelated) sequences) to produce a diverse set of recombinant nucleic acids, including, for example, sets of homologous nucleic acids, as well as corresponding polypeptides.

Modification of Chitinase Nucleic Acids for Common Codon Usage in an Organism

The polynucleotide sequence encoding a particular chitinase can be altered to coincide with the codon usage of a particular host. For example, the codon usage of a monocot plant can be used to derive a polynucleotide that encodes a chitinase polypeptide of the invention and comprises preferred monocot codons. The frequency of preferred codon usage exhibited by a host cell can be calculated by averaging the frequency of preferred codon usage in a large number of genes expressed by the host cell. This analysis is preferably limited to genes that are highly expressed by the host cell. U.S. Pat. No. 5,824,864, for example, provides the frequency of codon usage by highly expressed genes exhibited by dicotyledonous plants and monocotyledonous plants.

When synthesizing a gene for improved expression in a host cell, it is desirable to design the gene such that its frequency of codon usage approaches the frequency of preferred codon usage of the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons.

Screens for Determining the Hydrolytic Activity of Chitinases

A method was developed by which yeast libraries could be screened for the functional expression of cloned chitinases. A plate-clearing assay (see, Wirth and Wolf, J. Microbiol. Methods 12:197–205 (1990)) was developed for determining the hydrolytic activity of chitinases. Briefly, a yeast strain (Pichia pastoris KM-71 (Invitrogen)) was modified by two rounds of EMS mutagenesis, in order to reduce the clearing zones generated by KM-71 colonies grown on CM-chitin-RBV-containing agar plates. After transformation of the mutagenized Pichia pastoris strain with libraries of chitinases or chitinase variants or fragments, functional enzymes can be identified by the presence of a clearing zone surrounding the colonies successfully expressing functional chitinases. The identified clones are then selected for subsequent characterization. The selected clones are grown in liquid and the expressed recombinant protein activity is determined in kinetic assays. Such kinetic assays can, for example, involve CM-chitin-RBV, or colloidal chitin as substrates (Wirth and Wolf, J. Microbiol. Methods 12:197–205 (1990); Reissig et al., J. Biol. Chem. 217: 959–966 (1955); Legrand et al., Proc. Natl. Acad. Sci. USA 84:6750–6754 (1987)). Specific activity measurements are then taken in substrate-saturating conditions.

Screens for Determining Anti-Fungal Activity of Chitinases

General methods to perform assays to test the effect of chitinases for anti-fungal activity are known in the art. These assays include both in vivo and in vitro methods of testing a polypeptide for anti-fungal activity.

In vivo methods for testing for anti-fungal activity include expressing a candidate chitinase polypeptide in a plant and then growing the plant in the presence of a fungal pathogen. Improved plant health of the transformant relative to an untransformed control indicates that the polypeptide has anti-fungal activity. Alternatively, fungal populations either in plant tissue or on the exterior of the plant or in the surrounding soil can be measured relative to the tissues or soil associated with untransformed control plants.

In vitro methods of assaying for antifungal activity include zone clearing assays, in which fungal spores or hyphae are allowed to grow on a solid growth medium. Chitinases are added to the growth medium, for example, by deposition onto filter paper disks, or by direct addition to wells that were previously formed in the medium. Alternatively, chitinases can be secreted by an expression host maintained on the same medium as the fungal pathogen. Antifungal activity is evidenced by the formation of a clearing zone around the chitinase or the chitinase-producing host. Antifungal activity can also be monitored in liquid format, preferably in microtiter plates. In this case, a purified chitinase, or a crude protein mix containing chitinase, is assayed in a liquid growth medium, in which fungal spores were allowed to germinate. The efficiency of the chitinase at preventing the growth of the fungal pathogen is evidenced by the turbidity of the liquid growth medium (absorbance measurement).

Isolation of Chitinase Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, Cold Spring Harbor Laboratory, Cold Spring Harbor, N.Y., (1989) or Current Protocols in Molecular Biology Volumes 1–3, John Wiley & Sons, Inc. (1994–1998) ("Ausubel et al.").

The isolation of chitinase nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, using restriction endonucleases, and are ligated with vector DNA to form concatemers that can be packaged into the appropriate vector. To prepare a cDNA library, mRNA is isolated from the desired organ, such as leaves, and a cDNA library which contains a chitinase gene transcript is prepared from the mRNA. Alternatively, cDNA may be prepared from mRNA extracted from other tissues in which chitinase genes or homologues are expressed.

The cDNA or genomic library can then be screened using a probe based upon the sequence of a cloned chitinase gene disclosed here. Probes may be used to hybridize with genomic DNA or cDNA sequences to isolate homologous genes in the same or different plant species. Alternatively, antibodies raised against a chitinase polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of chitinase genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR, see *PCR Protocols: A Guide to Methods and Applications*. (Innis, M, Gelfand, D., Sninsky, J. and White, T., eds.), *Academic Press*, San Diego (1990). Appropriate primers and probes for identifying chitinase sequences from plant tissues are generated from comparisons of the sequences provided here (odd numbered sequences between SEQ ID NO:3 and SEQ ID NO:15 and between SEQ ID NO: 21 and SEQ ID NO: 65).

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

One useful method to produce the nucleic acids of the invention is to isolate and modify the wild type maize chitinase polynucleotide sequences displayed in SEQ ID NO:1 and SEQ ID NO:2. Other sequences that can be modified include SEQ ID NO: 17 and SEQ ID NO:18. Several methods for sequence-specific mutagenesis of a nucleic acid are known and are described above. In addition, Ausubel et al., supra, describes oligonucleotide-directed mutagenesis as well as directed mutagenesis of nucleic acids using PCR. Such methods are useful to insert specific codon changes into the wild type maize chitinase A or B polynucleotide sequences, thereby constructing the nucleic acids of the invention. Basic cloning and PCR methods are also useful in combining subsequences of SEQ ID NO:1 and SEQ ID NO:2 to produce the polynucleotides of the invention.

Preparation of Recombinant Vectors

The nucleic acid sequences of the present invention can be expressed in a host cell such as bacteria, yeast, insect, mammalian, or preferably plant cells. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (such as, shuttle vectors) and selection markers for both prokaryotic and eukaryotic systems. Vectors are suitable for replication and integration in prokaryotes, eukaryotes, or both. See, Giliman & Smith, *Gene* 8:81 (1979); Roberts, et al., *Nature,* 328:731 (1987); Schneider, B., et al., *Protein Expr. Purif.* 6435:10 (1995); Berger, Sambrook, Ausubel (all supra). A catalogue of Bacteria and Bacteriophages useful for cloning is provided by the ATCC, The ATCC Catalogue of Bacteria and Bacteriophage (1992) Gherna et al. (eds). Additional basic procedures for sequencing, cloning and other aspects of molecular biology and underlying theoretical considerations are also found in Watson et al. (1992) RECOMBINANT DNA Second Edition Scientific American Books, NY.

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). In some embodiments a DNA sequence coding for the desired polypeptide, for example a cDNA sequence encoding a full length protein, is combined with transcriptional and translational initiation regulatory sequences which will direct the transcription of the sequence from the gene in the intended tissues of the transformed plant. Native or heterologous promoters can be operatively linked to transcriptional sequences.

Specifically, the chitinase sequences of the invention are provided in expression cassettes or DNA constructs for expression in the plant of interest. The cassette will include 5' and 3' regulatory sequences operably linked to a chitinase sequence of the invention. By "operably linked" a functional linkage between a promoter and a second sequence, wherein the promoter sequence initiates and mediates transcription of the DNA sequence corresponding to the second sequence is intended. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the chitinase sequence to be under the transcriptional regulation of the regulatory regions. The expression cassette may additionally contain selectable marker genes.

The expression cassette will include in the 5'–3' direction of transcription, a transcriptional and translational initiation region, a chitinase DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" it is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of chitinase in the host cell (i.e., plant or plant cell). Thus, the phenotype of the host cell (i.e., plant or plant cell) is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, as described above, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. As discussed above, the G-C content of the sequence may be adjusted to levels that are average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include, but are not limited to: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986) *Virology* 154:9–20); MDMV leader (Maize Dwarf Mosaic Virus); human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, Ed., Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334: 721–724 and U.S. patent application Ser. No. 10/072,307. Such disclosures are herein incorporated by reference. The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in the host cell of interest. In particular, for overexpression, a plant promoter fragment may be employed which will direct expression of the gene in all tissues of a regenerated plant. Such promoters are referred to herein as "constitutive" promoters and are active under most environmental conditions and states of development or cell differentiation. Such constitutive promoters include, for example, the core promoter of the Rsyn7 promoter (WO 99/43838 and U.S. Pat. No. 6,072,050); the core CaMV 35S promoter (Odell et al. (1985) *Nature* 313:810–812); rice actin (McElroy et al. (1990) *Plant Cell,* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, those disclosed in U.S. Pat. Nos. 5,608,149; 5,608,144; 5,604,121; 5,569, 597; 5,466,785; 5,399,680; 5,268,463; and 5,608,142, and the 1'- or 2'-promoter derived from T-DNA of *Agrobacterium tumafaciens*, and other transcription initiation regions from various plant genes known to those of skill. Such genes include for example, ACT11 from *Arabidopsis* (Huang et al. *Plant Mol. Biol.* 33:125–139(1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol.* 208:551–565 (1989)), and Gpc2 from maize (GenBank No. U45855, Manjunath et al., *Plant Mol. Biol.* 33:97–112 (1997)).

Alternatively, the plant promoter may direct expression of chitinase nucleic acids in a specific tissue, organ or cell type (i.e. tissue-specific promoters) or may be otherwise under more precise environmental or developmental control (for example, inducible promoters). Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also, WO 99/43819, which is herein incorporated by reference. Examples of environmental conditions that may effect transcription by inducible promoters include anaerobic conditions, elevated temperature, the presence of light, or spraying with chemicals/hormones. Tissue-specific promoters can be inducible. Similarly, tissue-specific promoters may only promote transcription within a certain time frame or developmental stage within that tissue. Other tissue specific promoters may be active throughout the life cycle of a particular tissue. One of skill will recognize that a tissue-specific promoter may drive expression of operably linked sequences in tissues other than the target tissue. Thus, as used herein, a tissue-specific promoter is one that drives expression preferentially in the target tissue or cell type, but may also lead to some expression in other tissues as well.

A number of tissue-specific promoters can also be used in the invention. With the appropriate promoter, any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. For instance, promoters that direct expression of nucleic acids in leaves, roots or flowers are useful for enhancing resistance to pests that infect those organs. For expression of a chitinase polynucleotide in the aerial vegetative organs of a plant, photosynthetic organ-specific promoters, such as the RBCS promoter (Khoudi, et al., *Gene* 197:343, 1997), can be used. Root-specific expression of chitinase polynucleotides can be achieved under the control of a root-specific promoter, for example, from the ANR1 gene (Zhang & Forde, *Science,* 279:407, 1998) and Keller, et al., *The Plant Cell* 3(10):1051–1061 (1991), which describes a root-specific control element in the GRP 1.8 gene of French bean. Any strong, constitutive promoters, such as the CaMV 35S promoter, can be used for the expression of chitinase polynucleotides throughout the plant.

Of particular interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include the potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225: 1570–1573); WIPI (Rohrneier et al. (1993) *Plant Mol. Biol.* 22:783–792 and Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners; the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced chitinase expression within a particular plant tissue. Tissue-preferred promoters include those disclosed in Yamamoto et al. (1997) *Plant J.* 12(2):255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

Leaf-specific promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol.*

*Biol.* 23(6):1129–1138; and Matsuoka et al. (1993) *Proc. Natl. Acad. Sci. USA* 90(20):9586–9590.

Root-preferred promoters are known and can be selected from the many available from the literature or isolated de novo from various compatible species. See, for example, Hire et al. (1992) *Plant Mol. Biol.* 20(2):207–218 (soybean root-specific glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of *Agrobacterium tumefaciens*); and Miao et al. (1991) *Plant Cell* 3(1):11–22 (full-length cDNA clone encoding cytosolic glutamine synthetase (GS), which is expressed in roots and root nodules of soybean). See also Bogusz et al. (1990) *Plant Cell* 2(7):633–641, which discloses two root-specific promoters isolated from hemoglobin genes from the nitrogen-fixing nonlegume *Parasponia andersonii* and the related non-nitrogen-fixing nonlegume *Trema tomentosa*. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69–76). They concluded that enhancer and tissue-preferred DNA determinants are dissociated in those promoters. Teeri et al. (1989) (*EMBO J.* 8(2): 343–350) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, which is an especially desirable combination of characteristics for use with an insecticidal or larvicidal gene. The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4): 759–772); the ZRP2 promoter (U.S. Pat. No. 5,633,363); the IFS1 promoter (U.S. patent application Ser. No. 10/104,706) and the rolB promoter (Capana et al. (1994) *Plant Mol. Biol.* 25(4):681–691. See also U.S. Pat. Nos. 5,837,876; 5,750, 386; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see U.S. Pat. No. 6,225,529, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Production of Transgenic Plants

The method of transformation/transfection is not critical to the instant invention. Various methods of transformation or transfection are currently available. As newer methods are available to transform crops or other host cells they may be directly applied to the present invention. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed with the nucleotide sequences of the present invention.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (U.S. Pat. Nos. 5,563,055 and 5,981,840), direct gene transfer (Paszkowski et al. (1984) *EMBO J.* 3:2717–2722), and ballistic particle acceleration (see, for example, U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, Eds., Gamborg and Phillips (Springer-Verlag, Berlin); and McCabe et al. (1988) *Biotechnology* 6:923–926), and Lec1 transformation (WO 00/28058). See also, Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); U.S. Pat. Nos. 5,240,855, 5,322,783 and 5,324,646; Klein et al. (1988) *Plant Physiol.* 91:440–444 (maize); Fromm et al. (1990) *Biotechnology* 8:833–839 (maize); Hooykaas-Van Slogteren et al. (1984) *Nature*(London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrids having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago saliva*), rice (*Oryza saliva*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseoles vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057), and the lambda derived P L promoter and N-gene ribosome binding site (Shimatake et al. (1981) *Nature* 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. (Palva et al. (1983) *Gene* 22:229–235 and Mosbach et al. (1983) *Nature* 302: 543–545) and *Salmonella*.

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for the production of the proteins of the instant invention.

Synthesis of heterologous nucleotide sequences in yeast is well known. Sherman, F., et al. (1982) *Methods in Yeast Genetics*, Cold Spring Harbor Laboratory, is a well recognized work describing the various methods available to produce a protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, an origin of replication, termination sequences and the like, as desired.

A protein of the present invention, once expressed, can be isolated from yeast by lysing the cells and applying standard protein isolation techniques to the lysate. The monitoring of the purification process can be accomplished by using Western blot techniques, radioimmunoassay or other standard immunoassay techniques.

The sequences of the present invention can also be ligated into various expression vectors for use in transfecting cell cultures of, for instance, mammalian, insect, or plant origin. Illustrative cell cultures useful for the production of these peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider, *J. Embryol. Exp. Morphol.* 27:353–365 (1987).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al. (1983) *J. Virol.* 45:773–781). Additionally, gene sequences to control replication in the host cell may be incorporated into the vector such as those found in bovine papilloma virus type-vectors. See, Saveria-Campo, M., (1985) Bovine Papilloma Virus DNA a Eukaryotic Cloning Vector in *DNA Cloning Vol. II A Practical Approach*, D. M. Glover, Ed., IRL Press, Arlington, Va. pp. 213–238.

Animal and lower eukaryotic (e.g., yeast) host cells are competent or rendered competent for transfection by various means. There are several well-known methods of introducing DNA into animal cells. These include, but are not limited to: calcium phosphate precipitation, fusion of the recipient cells with bacterial protoplasts containing a DNA of interest, treatment of the recipient cells with liposomes containing a DNA of interest, DEAE dextrin, electroporation, biolistics, and micro-injection of a DNA of interest directly into the cells. The transfected cells are cultured by means well known in the art. See, Kuchler, R. J. (1997) *Biochemical Methods in Cell Culture and Virology*, Dowden, Hutchinson and Ross, Inc.

It is recognized that antisense constructions complementary to at least a portion of the messenger RNA (mRNA) for the chitinase sequences of the present invention can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

In some embodiments, the content and/or composition of polypeptides of the present invention in a plant, may be modulated by altering, in vivo or in vitro, the promoter of the nucleotide sequence to up- or down-regulate expression. For instance, an isolated nucleic acid comprising a promoter sequence operably linked to a polynucleotide of the present invention is transfected into a plant cell. Subsequently, a plant cell comprising the promoter operably linked to the polynucleotide of the present invention is selected for by means known to those of skill in the art such as, but not limited to, Southern blot, DNA sequencing, or PCR analysis using primers specific to the promoter and to the polynucleotide of the present invention and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, the concentration or composition of the polypeptides of the present invention is increased or decreased by at least 5%, 10%, 20%, 30%, 40%, 50%, 60%, 70%, 80%, or 90% relative to a native control plant, plant part, or cell lacking the aforementioned recombinant expression cassette. Accordingly, modulation in the present invention may occur during and/or subsequent to growth of the plant to the desired stage of development. Accordingly, modulating nucleic acid expression temporally and/or in particular tissues can be controlled by employing the appropriate promoter operably linked to a polynucleotide of the present invention in, for example, sense or antisense orientation as discussed in greater detail, supra. Induction of the expression of a polynucleotide of the present invention can also be controlled by exogenous administration of an effective amount of inducing compound. Inducible promoters and inducing compounds, which activate expression from these promoters, are well known in the art. In preferred embodiments, the polypeptides of the present invention are modulated in monocots, particularly maize.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of chitinase mRNA or protein in transgenic plants. Methods for detecting and quantitation of mRNAs or proteins are well known in the art.

Methods of Assaying Chitinase Activity

A variety of assays can be used to determine whether a particular polypeptide has chitinase activity. Typically, activity of a chitinase candidate is compared to a negative control (i.e., a sample that comprises no proteins with chitinase activity or that comprise the reagents of the sample without any other proteins). As an additional control, a candidate polypeptide's chitinase activity can be compared to chitinases such as SEQ ID NOs: 1 and 2 to identify candidates with improved enzymatic activity relative to the chitinases of SEQ ID NO:1 and 2.

One simple test includes assaying for the ability of a polypeptide to hydrolyze carboxymethyl-chitin-remazol brilliant violet. Carboxymethyl-chitin-remazol brilliant violet is prepared according to Wirth and Wolf, supra. Briefly, chitin (for example, crab shell chitin (practical grade) is suspended in a base (such as, sodium hydroxide), shaken and the filtered. The dry chitin cake (retentate) is resuspended in a solution of acid in alcohol (for example, 12% chloroacetic acid in isopropanol, shaken and filtered again. The retentate is then washed twice in isopropanol and dissolved in water. The pH of the CM-chitin solution is then adjusted to about 7.

Dye can be linked to the chitin as follows. Carboxymethyl chitin (e.g., 1 liter) can be heated to about 50° C. and remazol brilliant violet (Sigma) (e.g., 5 g) is added under constant stirring. Sodium sulfate (e.g., 100 g) is then added in small amounts, followed by trisodium phosphate (dodecahydrate) (e.g., 7.8 g). After further stirring (e.g., at 50° C.), the CM-chitin-RBV is dialyzed against water and autoclaved.

The prepared carboxymethyl-chitin-remazol brilliant violet can be used to monitor hydrolysis as follows. Typically a purified polypeptide, crude bacterial or yeast lysate, culture supernatant or crude plant lysate containing the candidate polypeptide is added to a buffered solution (e.g., 20 mM sodium acetate, pH 5.5). Following an incubation period, non-hydrolyzed chitin is precipitated with hydrochloric acid, and chitin hydrolysis is estimated by measuring the absorbance of the soluble fraction at 550 nm.

An alternate screen involves measuring the endochitinase activity of candidate polypeptides on colloidal chitin. See, Reissig, et al. *J. Biol. Chem.* 217:959–966 (1955); Legrand, M., et al., *Proc. Natl. Acad. Sci USA* 84:6750–6754 (1987).

Methods of Enhancing Plant Resistance to Fungal Pathogens

The present invention provides for methods of enhancing plant resistance to fungal pathogens and insects by expressing chitinase polynucleotides and/or polypeptides in plants. Such methods find use in agriculture particularly in limiting the impact of plant pathogens on crop plants. While the choice of promoter will depend on the desired timing and location of expression of the anti-pathogenic nucleotide sequences, particular promoters include constitutive and pathogen-inducible promoters. Accordingly, transformed plants, plant cells, plant tissues and seeds thereof are provided. The antifungal activity of certain chitinase proteins has been described previously. See, e.g., U.S. Pat. Nos. 6,087,560; 5,993,808; 5,633,450; and 5,554,521. For example, in some embodiments, the chitinase polypeptides of the invention can be incorporated into and expressed by the tissues of a susceptible plant so that in the course of infecting the plant, the anti-fungal amounts of the selected chitinase come in contact with the invading hyphae of the invading fungus.

Enhanced resistance to any fungal pathogen is contemplated, including fungal pests such as species of *Fusarium, Sclerotinia, Botrytis, Cercospora, Gibberella, Oidium, Phytophthora, Sephoria, Verticillium, Alternaria, Cladisporium, Rhizoctonia, Ustilago,* or *Puccinia*. Other fungal pathogens are described in, e.g., Agrios, PLANT PATHOLOGY (1988). Enhanced resistance is generally achieved by introducing into a plant, or tissue or cell thereof, a structural gene encoding a chitinase of the invention, operably linked to plant regulatory sequences which cause expression of the chitinase gene in the plant.

As an alternative to expressing the polypeptides of the invention in plant cells, the presentation of the polypeptides can be made by formulating the polypeptide into an agricultural composition that is applied to the plant. In particular, the proteins of the invention can be formulated with an acceptable carrier into a pesticidal composition(s) for example, a suspension, a solution, an emulsion, a dusting powder, a dispersible granule, a wettable powder, and an emulsifiable concentrate, an aerosol, an impregnated granule, an adjuvant, a cotable paste, and also encapsulations in, for example, polymer substances. Thus, presentation of the agricultural composition may be achieved by external application either directly or in the vicinity of the plants or plant parts. The agricultural compositions may be applied to the environment of the fungal and insect pest(s), e.g., plants, soil or water, by spraying, dusting, sprinkling, or the like.

The present invention further contemplates using recombinant hosts, including microbial hosts and insect viruses, transformed with a gene encoding the chitinase polypeptides of the invention and applied on or near a selected plant or plant part susceptible to attack by a target insect. The hosts may be capable of colonizing a plant tissue susceptible to insect infestation or of being applied as dead or non-viable cells containing the chitinase. Microbial hosts of particular interest will be the prokaryotes and the lower eukaryotes, such as non-chitin-containing fungi (e.g., oomycetes). In some embodiments, the microbial host secretes the chitinase into their surrounding environment so as to contact a fungal cell.

Examples of prokaryotes, both Gram-negative and -positive, that are potentially useful for expressing chitinases include Enterobacteriaceae, such as *Escherichia*; Bacillaceae; Rhizoboceae, such as *Rhizobium* and Rhizobacter; Spirillaceae (such as *photobacterium*), *Zymomonas, Serratia, Aeromonas, Vibrio, Desulfovibrio, Spirillum; Lactobacillaceae; Pseudomonadaceae* (such as *Pseudomonas* and *Acetobacter*); *Azotobacteraceae* and *Nitrobacteraceae*.

Bacteria, and particularly *rhizobacteria*, modified in accordance with the present invention and grown to sufficient proportions, e.g., by fermentation, can be used to combat chitin-containing soil pathogens by application of the bacteria to soil, seeds, vegetative plant parts or irrigation water. For example, mucolytic bacteria created in accordance with the invention can be used in such ways to attack or inhibit fungi. The microbial host can be applied in various formulations containing agronomically acceptable adjuvants or carriers in dosages and concentrations chosen to maximize the beneficial effect of the *rhizobacteria*.

For application to soil, to soil mixes, or to artificial plant growth media, the microbial host may be applied as a powder or granule in a suitable carrier. Alternatively, the microbial host may be applied as a suspension or dispersion, e.g., as an aqueous suspension with a suitable protectant such as methylcellulose, dextran, dextrin, alginate, magnesium silicate. The microbial host may also be applied as a wettable powder.

For application to seeds, the microbial host may be applied as part of a seed coating composition, for instance mixed with xanthan gum, magnesium silicate, methylcellulose, gum arabic, polyvinyl pyrollidone, dextrins or dextrans. In addition, small amounts of partially hydrolyzed chitin may be added to the pelleting mix, dust granule, suspension, or wettable powder to enhance chitinase production. See, generally, Suslow et al., *Phytopathology* 72:199–206 (1982); and Kloepper et al., *Phytopathology* 71:590–592 (1981), for a discussion of *rhizobacteria* and seed coating compositions.

Bacteria expressing a chitinase in accordance with the present invention may also be applied to the above-ground surface of a plant, e.g., the leaf or stem surface, either to permit the modified bacteria to travel or spread to the roots or to inhibit chitinase-sensitive pathogens which may be present on blossoms or plant surfaces, for instance, fungal pathogens such as *Botrytis, Monilinia, Alternaria,* and *Cercospora*. Blossoms of *Prunus* sp., in particular, provide an ideal environment for the growth of epiphytic bacteria, e.g., *Pseudomonas syringae* or *Erwinia herbicola*, which have the ability to produce inhibitory levels of chitinase.

The method of the invention can also be used for introduction of chitinase genes into species of *Rhizobium* which enter into a nitrogen fixing symbiosis within the nodules of leguminous plants. The nodules are frequently the point of entry of pathogenic fungi and nematodes.

The recombinant host may be formulated in a variety of ways. It may be employed in wettable powders, granules or dusts, or by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other insecticidal additives, surfactants, and bacterial nutrients or other agents to enhance growth or stabilize bacterial cells. Liquid formulations may be aqueous-based or non-aqueous and employed as foams, gels, suspensions, emulsifiable concentrates, or the like. The ingredients may include rheological agents, surfactants, emulsifiers, dispersants, or polymers. In general, inoculants can be applied at any time during plant growth. Inoculation of large fields can be accomplished most effectively by spraying.

Selecting for Plants with Enhanced Resistance

Plants with enhanced resistance can be selected in many ways known to those of skill in the art. For example, to assess resistance to fungal attack, transgenic plants expressing the polypeptides of the invention are exposed to a fungal pathogen to which the wild type plant is susceptible. In some cases, for instance, the soil is infested with fungal spores. The plants are then monitored over a time period sufficient for pathogenesis by the fungus (e.g., one to four weeks). Monitoring of plants includes observation of viability, height, root mass and leaf area.

Combining Chitinase Polypeptides of the Invention with Other Proteins to Enhance Pest Resistance The polypeptides of the invention may be used alone or in combination with other proteins or agents to control different fungal pathogens. For example, chitinase can be combined with β-1,3 glucanase and/or ribosome inactivating protein (RIP). See, e.g., Jach, *Plant J* 8(1):97–109 (1995). Other antimicrobial components that can be combined with the chitinase of the invention include those discussed in Lamb, et al. *Biotechnology (N.Y.)* 10(11):1436–45 (1992).

Other examples of proteins that may be used in combination with antifungal proteins according to the invention include, but are not limited to, β-1,3-glucanases and other chitinases such as those obtainable from barley (Swegle M. et al, 1989, *Plant Mol. Biol.* 12, 403–412; Balance G. M. et al, 1976, *Can. J. Plant Sci.* 56, 459–466; Hoj P. B. et al, 1988, *FEBS Lett.* 230, 67–71; Hoj P. B. et al, 1989, *Plant Mol. Biol.* 13, 31–42 1989), bean (Boller T. et al, 1983, *Planta* 157, 22–31; Broglie K. E. et al. 1986, *Proc. Natl. Acad. Sci. USA* 83, 6820–6824; 1988 *Planta* 174, 364–372); Mauch F. & Staehelin L. A., 1989, *Plant-Cell* 1, 447–457); cucumber (Metraux J. P. & Boller T. (1986), *Physiol. Mol. Plant Pathol.* 28, 161–169); leek (Spanu P. et al, 1989, *Planta* 177, 447–455); maize (Nasser W. et al., 1988, *Plant Mol. Biol.* 11, 529–538), oat (Fink W. et al, 1988, *Plant Physiol.* 88, 270–275), pea (Mauch F. et al 1984, *Plant Physiol.* 76, 607–611; Mauch F. et al, 1988, *Plant Physiol.* 87, 325–333), poplar (Parsons, T. J. et al, 1989, *Proc. Natl. Acad. Sci. USA.* 86, 7895–7899), potato (Gaynor J. J. 1988, *Nucl. Acids Res.* 16, 5210; Kombrink E. et al 1988, *Proc. Natl. Acad. Sci. USA* 85, 782–786; Laflamme D. and Roxby R., 1989, *Plant Mol. Biol.* 13, 249–250), tobacco (e.g. Legrand M. et al 1987, *Proc. Natl. Acad. Sci. USA* 84, 6750–6754; Shinshi H. et al. 1987, *Proc. Natl. Acad. Sci. USA* 84, 89–93), tomato (Joosten M. H. A. & De Wit P. J. G. M. 1989, *Plant Physiol.* 89, 945–951), wheat (Molano J. et al, 1979, *J. Biol. Chem.* 254, 4901–4907), and the like.

The following examples are offered by way of illustration and not by way of limitation.

EXAMPLES

Example 1

Cloning and Protein Expression of the Polynucleotides of the Invention

Genes, referred to as parent genes, were amplified by PCR, with flanking regions containing restriction sites Cla I at the 5'-end and Xba I followed by a stop site at the 3'-end. The amplified sequences were ligated, in frame with the α-factor signal sequence, to the *E. coli-Pichia pastoris* shuttle vector pPICZαC (Invitrogen) in which the DNA fragment comprised between Cla I and Xba I had been deleted. Cloning of the constructed plasmid in the *E. coli* strain Top 10 F' (Invitrogen) was performed according to the manufacturer's instructions.

A library of nucleic acids (in some cases comprising a polynucleotide encoding a histidine tag) related to the parent gene sequences was obtained. The polynucleotides of the library were then ligated into pPICZαC, transformed into *E. coli* and the library was then amplified on LSLB agar plates supplemented with 25 μM Zeocin.

Plasmid DNA from the entire library was extracted, linearized at a unique Pme I restriction site, and transformed by multiple electroporation events into the *Pichia pastoris* strain KM71. After selection of *Pichia pastoris* transformants on YPDS agar plates containing 100 μM Zeocin, expression of the chitinases was induced in liquid format. High throughput expression required initial growth of the selected *Pichia pastoris* clones in 400 to 800 μl of BMGY medium, supplemented with a glass bead (biomass production). Growth was performed at 30° C. and 80% humidity under vigorous shaking. After 2–3 days of biomass production, the *Pichia* cultures were centrifuged and resuspended in minimal medium (BMMH) for chitinase expression. Maximum expression was obtained after four days of culture under conditions similar to those used for biomass production.

Example 2

Identification of Chitinase Clones with Improved Chitinase Activity

In general, the chitinases with improved activity were identified as follows. Proteins secreted to the culture medium were assayed for their ability to hydrolyze chitin. The clones with the best hydrolytic activity against carboxymethyl-chitin-remazol brilliant violet (CM-chitin-RBV) were selected. DNA from the most active clones was isolated. Selected chitinase clones were sequenced by using PCR primers specific to regions flanking the genes.

Improved Chitinases were Identified by Screening for their Ability to Hydrolyze Chitin Two colorimetric methods were used to determine the chitinolytic activity of the clones: one based on the hydrolysis of the soluble, dye-labelled substrate carboxymethyl-chitin-remazol brilliant violet (CM-chitin-RBV) (Wirth and Wolf *J. Microbiol. Methods* 12:197–205 (1990)), and the second by measuring the endochitinase activity of the enzymes on colloidal chitin (Reissig, et al. *J. Biol. Chem.* 217:959–966 (1955); Legrand, et al. *Proc. Natl. Acad. Sci USA* 84:6750–6754) (1987))

Selection of active clones was performed in 96-well microtiter plates by adding 5 μl of *Pichia* culture supernatant to wells containing the substrate CM-chitin-RBV in 20 mM sodium acetate buffer, pH 5.5. After a 30 min incubation at 37° C., acid-insoluble chitin was precipitated with HCl and the amount of chitin hydrolyzed by the enzymatic treatment was estimated by measuring the absorbance at 550 nm of the supernatant.

Clones that tested positive for enzyme activity were re-arrayed into mitrotiter plates, expressed again and re-tested. The clones with the best activity were then further characterized.

Characterization of Improved Chitinase Clones

The clones with the best activity were grown and expressed in bulk. The so produced chitinases, which represented ~90% of the protein content of the *Pichia* culture supernatants, were concentrated 100 to 200-fold with centrifugal concentration devices and dialyzed over night against reaction buffer (20 mM sodium acetate, pH 5.5). Chitinases normalized for protein concentration were used in endochitinase and in CM-chitin-RBV hydrolysis assays under substrate-saturating conditions. Under such conditions, the chitinolytic reactions were linear with respect to enzyme concentration. The activity of the improved chitinases was expressed in multiples of the activity of the best wild-type control protein (Chitinase A (SEQ ID NO:1)). Table 1 demonstrates the results of the CM-chitin-RBV hydrolysis assays. Table 2 shows the results of the endochitinase assays.

$K_m$ and $V_{max}$ values were determined for the product of the clone r1B$_{10}$ using the CM-chitin-RBV hydrolysis assay. The gene product was found to have the same $K_m$ as the expressed wild-type Chitinase A (SEQ ID NO:1). The $V_{max}$ of the gene product was 3- to 4-fold higher than wild-type Chitinase A.

FIGS. 2 and 3 illustrate the sequence relationship between SEQ ID NO:1 and the improved chitinase sequences. FIG. 2 illustrates the nucleotide differences between the clones and FIG. 3 illustrates amino acid differences between the gene products.

TABLE 1

Activity of the novel chitinases as determined by the endochitinase assay

| Clone | Improvement over wild-type Chitinase A (SEQ ID NO: 1) |
|---|---|
| r1B6 (SEQ ID NO: 4) | 3.2-fold |
| r1B10 (SEQ ID NO: 6) | 3.6-fold |
| r1D4 (SEQ ID NO: 8) | 3.9-fold |
| r2A2 (SEQ ID NO: 10) | 4.3-fold |
| r2C2 (SEQ ID NO: 12) | 3.2-fold |
| r2E1 (SEQ ID NO: 14) | 6.6-fold |
| r2H2 (SEQ ID NO: 16) | 4.6-fold |

TABLE 2

Activity of the novel chitinases as determined by CM-chitin-RBV hydrolysis

| Clone | Improvement over wild-type Chitinase A (SEQ ID NO: 1) |
|---|---|
| r1B6 (SEQ ID NO: 4) | 5.6-fold |
| r1B10 (SEQ ID NO: 6) | 5.1-fold |
| r1D4 (SEQ ID NO: 8) | 1.9-fold |
| r2A2 (SEQ ID NO: 10) | 4.8-fold |
| r2C2 (SEQ ID NO: 12) | 4.5-fold |
| r2E1 (SEQ ID NO: 14) | 5.4-fold |
| r2H2 (SEQ ID NO: 16) | 8.9-fold |

Example 3

Improved Antifungal Activity of a Chitinase Clone with Enhanced Chitinolytic

Activity

Clones with enhanced chitinase activity were tested for their ability to prevent hyphal growth of the pathogenic fungus *Fusarium moniliforme*. For preliminary screens, secreted protein was concentrated and buffer-exchanged before being used in antifungal assays. The secreted gene product was typically 90–95% pure, according to Coomassie-stained SDS-PAGE. For more precise characterization, protein secreted into the *Pichia pastoris* culture medium was concentrated and purified before being used in the antifungal assays.

Improved Chitinase Gene Products were Identified by their Ability to Inhibit Hyphal Growth of the Phytopathogenic Fungus *Fusarium Moniliforme*

Spores of *Fusarium moniliforme* were pre-germinated in clear 96-well microtiter plates in Vogel's Minimal Medium (VMM) (Vogel, *Microb. Genet. Bull.* 13:42–43 (1956); Vogel, *Am. Nature* 98:435–446 (1964)). Chitinases expressed with a histidine tag at their C-terminus were purified over nickel-nitrilotriacetic acid-charged agarose beads (Ni-NTA Superflow, Qiagen) according to the manufacturer's instructions. Chitinases were eluted from the Ni-NTA matrix with a phosphate buffer containing 250 mM imidazole. The imidazole-containing buffer was exchanged for 20 mM sodium acetate, pH 5.5, by dialysis or by centrifugation through centrifugal filtration devices. Purified chitinases were added to the germinated spores to final concentrations of 0, 20, 50, 100, 200 and 500 μg/ml. In some instances, 6 μg/ml of β-1,3-glucanase from *Helix pomatia* was added to the mix. After incubation at 25° C. for ~45 h, the absorbance at 600 nm was recorded for each of the chitinase-containing microtiter wells. FIG. 1 demonstrates the antifungal activity of the gene product r2C2 (SEQ ID NO:12) as compared to the antifungal activity of the Chitinase A (SEQ ID NO:1). Forty percent inhibition of hyphal growth was achieved with a ~4-fold lower concentration of the r2C2 gene product, as compared to Chitinase A (SEQ ID NO:1).

Example 4

Improved Antifungal Activity of Additional Chitinase Clones with Enhanced Chitinolytic Activity Additional clones with enhanced chitinase activity were tested for their ability to prevent hyphal growth of the pathogenic fungus *Fusarium moniliforme*. For preliminary screens, secreted protein was concentrated and buffer-exchanged before being used in antifungal assays. The secreted gene product was typically 90–95% pure, according to Coomassie-stained SDS-PAGE. For more precise characterization, protein secreted into the *Pichia pastoris* culture medium was concentrated and purified before being used in the antifungal assays.

Antifungal Activity of Purified Chitinases

Spores of *Fusarium moniliforme* were pre-germinated in clear 96-well microtiter plates in Vogel's Minimal Medium (VMM) (Vogel, *Microb. Genet. Bull.* 13:42–43 (1956); Vogel, *Am. Nature* 98:435–446 (1964)). Purified chitinases were added to the germinated spores to final concentrations between 0 and 200 μg/ml. Six μg/ml of β-1,3-glucanase from *Helix pomatia* was added to the mix. After incubation at 25° C. for ~45 h, the absorbance at 600 nm was recorded for each of the chitinase-containing microtiter wells. FIGS. 4 and 5 demonstrate the improved antifungal activity of the gene products 4M1/1_H2 (SEQ ID NO: 24), 4M1/11_C10 (SEQ ID NO:22), and 2M1/26_C2 (SEQ ID NO:26) as compared to the antifungal activity of the previously identified "hit" r2C2 (SEQ ID NO: 12) and of the wild-type protein Chitinase A.

Example 5

Figure 8:
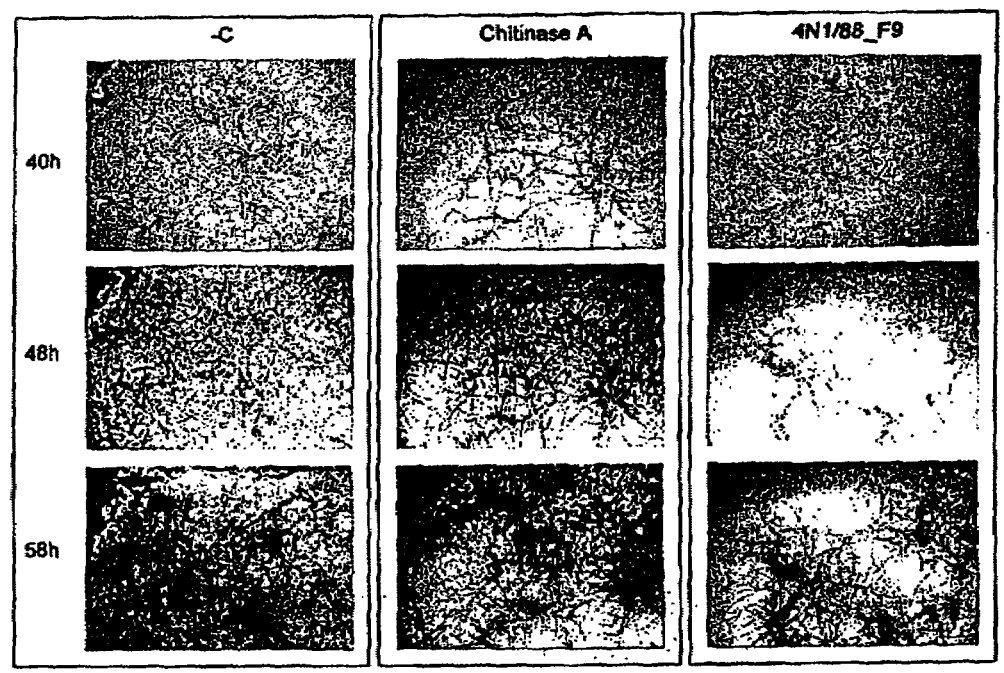
FIG. 8 illustrates antifungal activity of chitinases on solid medium. Purified chitinases were incorporated into cooling agar-VMM medium in 96-well microtiter plates. One hundred *Fusarium moniliforme* spores were added to each well and pictures were taken at 40 h, 48 h, and 58 h after the spore addition, on an inverted microscope (4× objective). Hyphal growth is compared in a control well not containing chitinase and in wells containing the wild-type chitinase 1-2SCH (Chitinase A) and the hit 4N1/88 F9 (SEQ ID NO: 56).

New Method for Testing the Antifungal Activity of Chitinases and the Improved Antifungal Activity of Additional Chitinase Clones with Enhanced Chitinolytic Activity Purified chitinases were tested for their ability to prevent hyphal growth of the pathogenic fungus *Fusarium moniliforme* grown on solid agar. In classic antifungal assays, anti-fungal proteins are added to filter paper disks deposited onto agar plates used to grow the pathogenic fungi. As the fungus grows towards the filter disk, a clearing zone is produced around the disk. We have found that *Fusarium moniliforme* responds poorly to these classic antifungal assays, either because the anti-fungal protein (i.e. chitinases) do not diffuse readily into the agar medium, or because *Fusarium moniliforme* hyphae can grow over a long distance without coming into contact with the medium. Therefore, we incorporated the chitinases under test directly into Vogel's Minimal Medium, VMM (Vogel, 1956, 1964), modified so as to contain only 1% sucrose, and poured the chitinase-agar medium into the wells of a 96-well microtiter plate. When the medium solidified, spores of *Fusarium moniliforme* were added to the wells and incubated at 22° C. The effect of the chitinases incorporated into the growth medium was evaluated under an inverted microscope. FIG. 8 demonstrates the effect of 100 or 300 μg of chitinase incorporated into 100 μl of solid growth medium. The wild-type chitinase, 1-2SCH (or chitinase A) is compared to the previously identified "hit" r2C2 (SEQ ID NO: 12) and the new "hit" 4N1/88_F9 (SEQ ID NO: 56).

Improvement of new chitinases as compared to the best wild-type clone and the previously identified hit "r2C2" (SEQ ID NO: 12) are illustrated in Table 3. The fold-improvement of a clone reflects the reduced protein concentration required to achieve similar inhibition of *Fusarium moniliforme* growth compared to "Chitinase A" and "r2C2".

TABLE 3

Antifungal activity of novel chitinases as compared to a wild-type chitinase and a previously identified hit.

| Clone | Fold improvement over r2C2 | Fold improvement over [Chitinase A] |
|---|---|---|
| r1AB2 (SEQ ID NO: 28) | 1.2 | 4.6 |
| r1AD4 (SEQ ID NO: 30) | 0.7 | 2.8 |
| r1AD6 (SEQ ID NO: 32) | 0.6 | 2.3 |
| r1AG9 (SEQ ID NO: 34) | 0.9 | 3.5 |
| r1AH8 (SEQ ID NO: 36) | 1.6 | 6.2 |
| r1AH9 (SEQ ID NO: 38) | 2.0 | 8.0 |
| r1BG5 (SEQ ID NO: 40) | 1.0 | 4.1 |
| r2C5 (SEQ ID NO: 42) | 0.7 | 2.8 |

Table 4 illustrates further improved chitinases. Purified chitinases were added to germinating spores of *Fusarium moniliforme* and their efficiency at inhibiting fungal growth was recorded by taking absorbance measurements at 600 nm. Activity measurements were compared to those obtained with the previously identified hit 4M1/11_C10 (SEQ ID NO: 22), and improvements relative to the wild-type clone 1-2SC (Chitinase A) were calculated.

TABLE 4

Antifungal activity of further improved chitinases

| Clone | Fold improvement over 4M1/11_C10 (SEQ ID NO: 22) | Fold improvement over [Chitinase A] |
|---|---|---|
| 4N1/11_B11 (SEQ ID NO: 62) | 1.2 | 18 |
| 4N1/14_B3 (SEQ ID NO: 58) | 1.1 | 17 |
| 4N1/2_H9 (SEQ ID NO: 50) | 1.35 | 20 |
| 4N1/23_G4 (SEQ ID NO: 52) | 1.5 | 23 |
| 4N1/30_D3 (SEQ ID NO: 64) | 1.4 | 21 |
| 4N1/33_F4 (SEQ ID NO: 60) | 1.4 | 21 |
| 4N1/35_G5 (SEQ ID NO: 66) | 1.55 | 23 |
| 4N1/68_E4 (SEQ ID NO: 54) | 1.25 | 19 |
| 4N1/75_D3 (SEQ ID NO: 48) | 1.3 | 20 |
| 4N1/80_F8 (SEQ ID NO: 46) | 1.15 | 17 |
| 4N1/88_F9 (SEQ ID NO: 56) | 1.55 | 23 |
| 4N1/95_H3 (SEQ ID NO: 44) | 1.3 | 20 |

Antifungal Activity of Purified Chitinases as Tested in Liquid Medium

Figure 9:
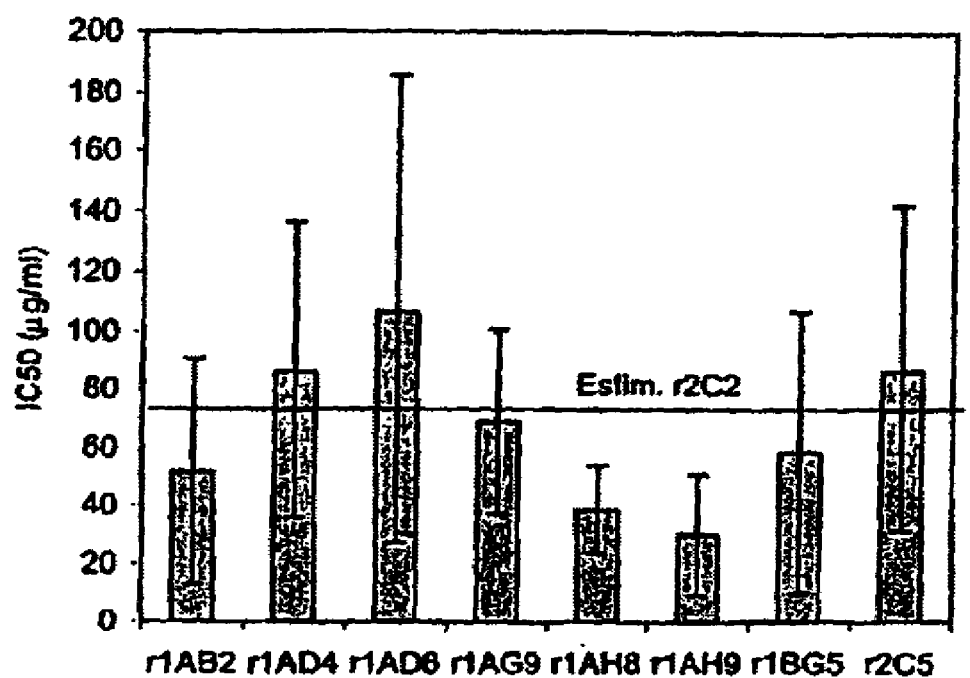
FIG. 9 illustrates antifungal activity of improved chitinases (r1AB2 (SEQ ID NO: 28), r1AD4 (SEQ ID NO: 30), r1AD6 (SEQ ID NO: 32), r1AG9 (SEQ ID NO: 34), r1AH8 (SEQ ID NO: 36), r1AH9 (SEQ ID NO: 38), r1BG5 (SEQ ID NO: 40), r2C5 (SEQ ID NO: 42)). Purified chitinases were added to germinating spores of *Fusarium moniliforme* and their efficiency at inhibiting fungal growth was recorded by taking absorbance measurements at 600 nm. The average concentration of chitinase required to inhibit fungal growth by 50% is reported. The horizontal line at IC50=60 µg/ml corresponds to the activity of hit r2C2 (SEQ ID NO: 12). Protein concentrations were determined with ovalbumin as a standard, therefore, IC50 values are in are given in ovalbumin equivalents.
Figure 10:
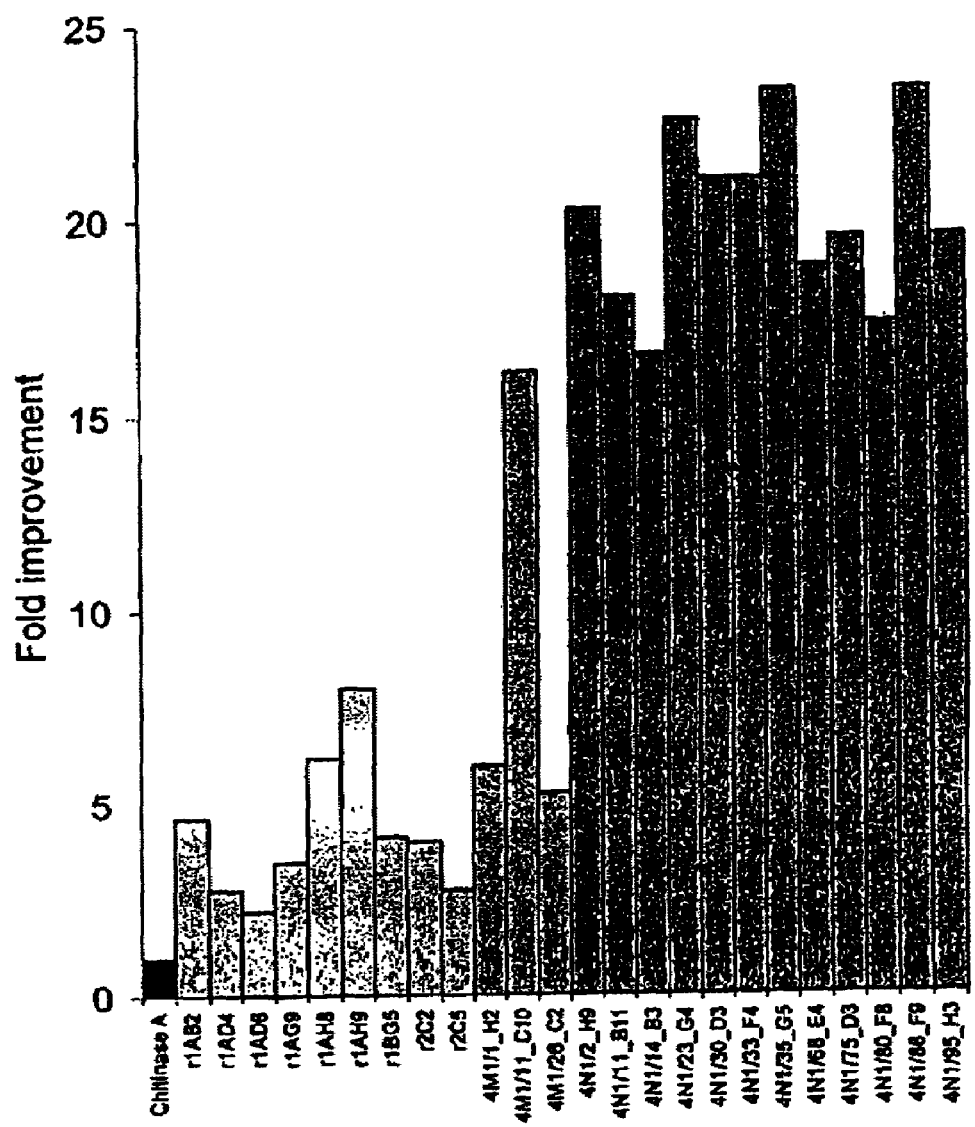
FIG. 10 illustrates improvements in the antifungal activity of later shuffled chitinases over previously shuffled chitinases (r1AB2 (SEQ ID NO: 28), r1AD4 (SEQ ID NO: 30, r1AD6 (SEQ ID NO: 32), r1AG9 (SEQ ID NO: 34), r1AH8 (SEQ ID NO: 36), r1AH9 (SEQ ID NO: 38), r1BG5 (SEQ ID NO: 40), r2C2 (SEQ ID NO: 12), r2C5 (SEQ ID NO: 42), 4M1/1_H2 (SEQ ID NO: 24), 4M1/11_C10 (SEQ ID NO: 22), 4M1/26_C2 (SEQ ID NO: 26), 4N1/2_H9 (SEQ ID NO: 50), 4N1/11_B11 (SEQ ID NO: 62), 4N1/14_B3 (SEQ ID NO: 58), 4N1/23_G4 (SEQ ID NO: 52), 4N1/30_D3 (SEQ ID NO: 64), 4N1/33_F4 (SEQ ID NO: 60), 4N1/35_G5 (SEQ ID NO: 66), 4N1/68_E4 (SEQ ID NO: 54), 4N1/75_D3 (SEQ ID NO: 48), 4N1/80_F8 (SEQ ID NO: 46), 4N1/88_F9 (SEQ ID NO: 56), and 4N1/95_H3 (SEQ ID NO: 44)). Purified chitinases were added to germinating spores of *Fusarium moniliforme* and their efficiency at inhibiting fungal growth was recorded by taking absorbance measurements at 600 nm. Activity measurements are expressed in number of folds the clones are improved over the wild-type clone 1-2SC (Chitinase A).

Spores of *Fusarium moniliforme* were pre-germinated in clear 96-well microtiter plates in Vogel's Minimal Medium (VMM) (Vogel, *Microb. Genet. Bull.* 13:42–43 (1956); Vogel, *Am. Nature* 98:435–446 (1964)). Purified chitinases were added to the germinated spores to final concentrations between 0 and 200 μg/ml. Six μg/ml of β-1,3-glucanase from *Helix pomatia* was added to the mix. After incubation at 25° C. for ~45 h, the absorbance at 600 nm was recorded for each of the chitinase-containing microtiter wells. FIG. 9 and Table 3 demonstrate the improved antifungal activity of gene products resulting from the first and second rounds of shuffling: r1AB2 (SEQ ID NO: 28); r1AD4 (SEQ ID NO: 30); r1AD6 (SEQ ID NO: 36); r1AG9 (SEQ ID NO: 34); r1AH8 (SEQ ID NO: 36); r1AH9 (SEQ ID NO: 38); r1BG5 (SEQ ID NO: 40), and r2C5 (SEQ ID NO: 42). They are compared to the antifungal activity of the previously identified "hit" r2C2 (SEQ ID NO: 12) and of the wild-type protein (Chitinase A), also named 1-2SCH in previous invention disclosures. Ovalbumin was used as a standard for protein determinations. Therefore, $IC_{50}$ values are expressed in ovalbumin equivalents. If bovine serum albumin (BSA) had been used as a standard, the $IC_{50}$ values would be reduced by a factor 4.5. In other words, the $IC_{50}$ values would be 4.5-times lower (or better). The results expressed in "fold improvement" would remain unchanged. Results from a further selection of improved chitinases are shown in Table 4. Average fold improvements are described. The average $IC_{50}$ for the 12 improved hits equals 23 μg/ml. A summary of improved hits is provided in FIG. 10. FIGS. 11 and 12 show alignments of nucleic acid and protein sequences (compared to clone r1AB2 (SEQ ID NO: 28)) identified in this improved set of chitinases.

Example 6

Transformation and Regeneration of Transgenic Plants

Immature maize embryos from greenhouse donor plants are bombarded with a plasmid containing a chitinase nucleotide sequence operably linked to a ubiquitin promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as described below. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the chitinase nucleotide sequence operably linked to a ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water

10 μl (1 μg) DNA in Tris EDTA buffer (1 μg total DNA)

100 μl 2.5 M $CaCl_2$

10 μl 0.1 M spermidine

Each reagent is added sequentially to the tungsten particle suspension, which is maintained on a multitube vortexer. The final mixture is sonicated briefly and allowed to incubate under constant vortexing for 10 minutes. After the precipitation period, the tubes are centrifuged briefly, liquid removed, washed with 500 ml of 100% ethanol, and centrifuged for 30 seconds. Again the liquid is removed, and 105 μls of 100% ethanol is added to the final tungsten particle pellet. For particle gun bombardment, the tungsten/DNA particles are briefly sonicated and 10 μl is spotted onto the center of each macrocarrier and allowed to dry for about 2 minutes before bombardment.

Particle Gun Treatment

The sample plates are bombarded at manufacturers recommended levels in a particle gun commercially available from BioRad Laboratories, Hercules, Calif. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5 pot) containing potting soil and grown for 1 week in a growth chamber, the plants are subsequently grown an additional 1–2 weeks in the greenhouse, then transferred to classic 600 pots (1.6 gallon) and grown to maturity. Plants are monitored and scored for altered antimicrobial activity.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-1$H_2O$ following adjustment to pH 5.8 with KOH); 3.0 g/l Gelrite (added after bringing to volume with D-1$H_2O$); and 0.85 mg/l silver nitrate and 3.0 mg/l Bailiffs (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 μl pyridoxine HCL, and 0.40 g/l glycine brought to volume with polished D-1$H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-1$H_2O$ after adjusting to pH 5.6); 3.0 g/l Gelrite (added after bringing to volume with D-I $H_2O$); and 1.0 mg/l indole acetic acid and 3.0 mg/l bialaphos (added after sterilizing the medium and cooling to 60° C.). Hormone-free medium (272V) comprises 4.3 g/l MS salts (GIBCO 11117–074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 7

Agrobacterium-Mediated Transformation in Maize

For *Agrobacterium*-mediated transformation of maize with a chitinase nucleotide sequence of the invention operably linked to a ubiquitin promoter, preferably the method of Zhao is employed (U.S. Pat. No. 5,981,840 and WO98/32326, the contents of which are hereby incorporated by reference). Briefly, immature embryos are isolated from maize and the embryos are contacted with a suspension of *Agrobacterium*, where the bacteria are capable of transferring the DNA construct containing the chitinase nucleotide sequence to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably, the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably, the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 8

Soybean Embryo Transformation

Soybean embryos are bombarded with a plasmid containing the chitinase nucleotide sequences operably linked to a ubiquitin promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures are maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the chitinase nucleotide sequence operably linked to the ubiquitin promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and again at eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Sunflower Meristem Tissue Transformation

Sunflower meristem tissues are transformed with an expression cassette containing the chitinase sequence operably linked to a ubiquitin promoter as follows (see also European Patent Number EP 0 486233, herein incorporated by reference, and Malone-Schoneberg et al. (1994) *Plant Science* 103:199–207). Mature sunflower seeds (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15:473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzylaminopurine (6-BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to *Agrobacterium* treatment (Bidney et al. (1992) *Plant Mol. Biol.* 18:301–313). Thirty to forty explants are placed in a circle at the center of a 60×20 mm plate. Approximately 4.7 mg of 1.8 mm tungsten microprojectiles are resuspended in 25 ml of sterile TE buffer (10 mM Tris HCl, 1 mM EDTA, pH 8.0) and a 1.5 ml aliquot is used per bombardment. Each plate is bombarded twice through a 150 mm nytex screen placed 2 cm above the samples in a PDS 1000® particle acceleration device available from BioRad Laboratories, Hercules, Calif.

Disarmed *Agrobacterium tumefaciens* strain EHA105 is used in all transformation experiments. A binary plasmid vector comprising the expression cassette that contains the chitinase gene operably linked to the ubiquitin promoter is introduced into *Agrobacterium* strain EHA105 via freeze-thawing as described by Holsters et al. (1978) *Mol. Gen.*

*Genet.* 163:181–187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on this selection media and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for chitinase activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by chitinase activity analysis of leaf extracts while transgenic seeds harvested from NPTII-positive $T_0$ plants are identified by chitinase activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours in the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no 6-BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for chitinase activity using assays known in the art. After positive (i.e., for chitinase expression) explants are identified, those shoots that fail to exhibit chitinase activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for chitinase expression are grafted to Pioneer® hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. in the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated nucleic acid comprising a polynucleotide encoding a chitinase polypeptide, wherein the chitinase polypeptide is at least 95% identical to SEQ ID NO:56.

2. The nucleic acid of claim 1, wherein the chitinase polypeptide exhibits a chitinase activity of at least 20% of the chitinase activity of Chitinase A (SEQ ID NO:1).

3. The nucleic acid of claim 1, wherein the chitinase polypeptide exhibits a chitinase activity of at least 200% of the chitinase activity of Chitinase A (SEQ ID NO:1).

4. An isolated nucleic acid comprising a polynucleotide encoding a chitinase polypeptide, wherein the chitinase polypeptide consists essentially of SEQ ID NO:56.

5. The nucleic acid of claim 4, wherein the chitinase polypeptide is SEQ ID NO:56.

6. An isolated nucleic acid comprising a polynucleotide encoding a polypeptide having chitinase activity, wherein the polynucleotide consists essentially of SEQ ID NO:55.

7. The nucleic acid of claim 6, wherein the polynucleotide is SEQ ID NO:55.

8. A recombinant expression cassette comprising the nucleic acid of claim 1 operably linked to a promoter.

9. The recombinant expression cassette of claim 8, wherein the promoter is a tissue-specific promoter.

10. The recombinant expression cassette of claim 8, wherein the promoter is a constitutive promoter.

11. The recombinant expression cassette of claim 8, wherein the promoter is an inducible promoter.

12. A vector comprising the recombinant expression cassette of claim 8.

13. The vector of claim 12, wherein the promoter is a tissue-specific promoter.

14. The vector of claim 12, wherein the promoter is a constitutive promoter.

15. The vector of claim 12, wherein the promoter is an inducible promoter.

16. A recombinant expression cassette comprising the nucleic acid of claim 4 operably linked to a promoter.

17. The recombinant expression cassette of claim 16, wherein the promoter is a tissue-specific promoter.

18. The recombinant expression cassette of claim 16, wherein the promoter is a constitutive promoter.

19. The recombinant expression cassette of claim 16, wherein the promoter is an inducible promoter.

20. A vector comprising the recombinant expression cassette of claim 16.

21. The vector of claim 20, wherein the promoter is a tissue-specific promoter.

22. The vector of claim 20, wherein the promoter is a constitutive promoter.

23. The vector of claim 20, wherein the promoter is an inducible promoter.

24. A recombinant expression cassette comprising the nucleic acid of claim 6 operably linked to a promoter.

25. The recombinant expression cassette of claim 24, wherein the promoter is a tissue-specific promoter.

26. The recombinant expression cassette of claim 24, wherein the promoter is a constitutive promoter.

27. The recombinant expression cassette of claim 24, wherein the promoter is an inducible promoter.

28. A vector comprising the recombinant expression cassette of claim 24.

29. The vector of claim 28, wherein the promoter is a tissue-specific promoter.

30. The vector of claim 28, wherein the promoter is a constitutive promoter.

31. The vector of claim 28, wherein the promoter is an inducible promoter.

32. A plant comprising a recombinant expression cassette comprising a promoter operably linked to a polynucleotide encoding a chitinase polypeptide having chitinase activity, wherein the polypeptide is consists essentially of SEQ ID NO:56.

33. The plant of claim 32, wherein the promoter is a tissue-specific promoter.

34. The plant of claim 32, wherein the promoter is a constitutive promoter.

35. The plant of claim 32, wherein the promoter is an inducible promoter.

36. The plant of claim 32, wherein the plant is maize.

37. A plant comprising a recombinant expression cassette comprising a promoter operably linked to a polynucleotide encoding a chitinase polypeptide having chitinase activity, wherein the polypeptide is consists essentially of a polypeptide at least 95% identical to SEQ ID NO:56.

38. The plant of claim 37, wherein the chitinase polypeptide exhibits a chitinase activity of at least 20% of the chitinase activity of Chitinase A (SEQ ID NO:1).

39. The plant of claim 37, wherein the chitinase polypeptide exhibits a chitinase activity of at least 200% of the chitinase activity of Chitinase A (SEQ ID NO:1).

40. The plant of claim 37, wherein the promoter is a tissue-specific promoter.

41. The plant of claim 37, wherein the promoter is a constitutive promoter.

42. The plant of claim 37, wherein the promoter is an inducible promoter.

43. The plant of claim 37, wherein the plant is maize.

44. A method of enhancing plant resistance to a fungus, the method comprising,
   a) introducing into a plant a recombinant expression cassette comprising a promoter operably linked to a polynucleotide encoding a chitinase polypeptide having chitinase activity, wherein the polypeptide consists essentially of SEQ ID NO:56; and
   b) selecting a plant with enhanced resistance to a fungus.

45. The method of claim 44, wherein the plant is maize.

46. The method of claim 44, wherein the promoter is a tissue-specific promoter.

47. A method of enhancing plant resistance to a fungus, the method comprising,
   a) introducing into a plant a recombinant expression cassette comprising a promoter operably linked to a polynucleotide encoding a chitinase polypeptide having chitinase activity, wherein the polypeptide consists essentially of a polypeptide at least 95% identical to SEQ ID NO:56; and
   b) selecting a plant with enhanced resistance for a fungus.

48. The method of claim 47, wherein the plant is maize.

49. The method of claim 47, wherein the fungus is from the genus *Fusarium*.

50. The method of claim 47, wherein the promoter is a tissue-specific promoter.

51. The method of claim 47, wherein the promoter is a constitutive promoter.

52. The method of claim 47, wherein the promoter is an inducible promoter.

53. A method of enhancing maize plant resistance to a fungus from the genus *Fusarium*, the method comprising,
   a) introducing into a maize plant a recombinant expression cassette comprising a promoter operably linked to a polynucleotide encoding a chitinase polypeptide having chitinase activity, wherein the polypeptide consists essentially of SEQ ID NO:56; and
   b) selecting a maize plant with enhanced resistance to a fungus from the genus *Fusarium*.

* * * * *

SEQUENCE LISTING

<160> NUMBER OF SEQ ID NOS: 66

<210> SEQ ID NO 1
<211> LENGTH: 255
<212> TYPE: PRT
<213> ORGANISM: Unknown
<220> FEATURE:
<223> OTHER INFORMATION: Chitinase A

<400> SEQUENCE: 1

```
Gln Asn Cys Gly Cys Gln Pro Asn Phe Cys Cys Ser Lys Phe Gly Tyr
  1               5                  10                  15

Cys Gly Thr Thr Asp Ala Tyr Cys Gly Asp Gly Cys Gln Ser Gly Pro
             20                  25                  30

Cys Arg Ser Gly Gly Gly Gly Gly Gly Gly Gly Gly Gly Gly Gly Gly
         35                  40                  45

Gly Ser Gly Gly Ala Asn Val Ala Asn Val Val Thr Asp Ala Phe Phe
 50                  55                  60

Asn Gly Ile Lys Asn Gln Ala Gly Ser Gly Cys Glu Gly Lys Asn Phe
 65                  70                  75                  80

Tyr Thr Arg Ser Ala Phe Leu Ser Ala Val Asn Ala Tyr Pro Gly Phe
                 85                  90                  95

Ala His Gly Gly Thr Glu Val Glu Gly Lys Arg Glu Ile Ala Ala Phe
            100                 105                 110

Phe Ala His Val Thr His Glu Thr Gly His Phe Cys Tyr Ile Ser Glu
        115                 120                 125

Ile Asn Lys Ser Asn Ala Tyr Cys Asp Ala Ser Asn Arg Gln Trp Pro
130                 135                 140

Cys Ala Ala Gly Gln Lys Tyr Tyr Gly Arg Gly Pro Leu Gln Ile Ser
145                 150                 155                 160

Trp Asn Tyr Asn Tyr Gly Pro Ala Gly Arg Asp Ile Gly Phe Asn Gly
                165                 170                 175

Leu Ala Asp Pro Asn Arg Val Ala Gln Asp Ala Val Ile Ala Phe Lys
            180                 185                 190

Thr Ala Leu Trp Phe Trp Met Asn Asn Val His Arg Val Met Pro Gln
        195                 200                 205

Gly Phe Gly Ala Thr Ile Arg Ala Ile Asn Gly Ala Leu Glu Cys Asn
    210                 215                 220

Gly Asn Asn Pro Ala Gln Met Asn Ala Arg Val Gly Tyr Tyr Lys Gln
225                 230                 235                 240

Tyr Cys Gln Gln Leu Arg Val Asp Pro Gly Pro Asn Leu Thr Cys
                245                 250                 255
```

<210> SEQ ID NO 2
<211> LENGTH: 248
<212> TYPE: PRT
<213> ORGANISM: Unknown
<220> FEATURE:
<223> OTHER INFORMATION: Chitinase B

<400> SEQUENCE: 2

```
Gln Asn Cys Gly Cys Gln Pro Asn Val Cys Cys Ser Lys Phe Gly Tyr
  1               5                  10                  15

Cys Gly Thr Thr Asp Glu Tyr Cys Gly Asp Gly Cys Gln Ser Gly Pro
             20                  25                  30

Cys Arg Ser Gly Gly Gly Gly Ser Ser Gly Gly Gly Gly Ala Asn Val
```

```
                35                  40                  45
Ala Ser Val Val Thr Gly Ser Phe Phe Asn Gly Ile Lys Ser Gln Ala
 50                  55                  60

Gly Ser Gly Cys Glu Gly Lys Asn Phe Tyr Thr Arg Ser Ala Phe Leu
 65                  70                  75                  80

Ser Ala Val Lys Ala Tyr Pro Gly Phe Ala His Gly Gly Ser Gln Val
                 85                  90                  95

Gln Gly Lys Arg Glu Ile Ala Ala Phe Phe Ala His Ala Thr His Glu
            100                 105                 110

Thr Gly His Phe Cys Tyr Ile Ser Glu Ile Asn Lys Ser Asn Ala Tyr
            115                 120                 125

Cys Asp Pro Thr Lys Arg Gln Trp Pro Cys Ala Ala Gly Gln Lys Tyr
130                 135                 140

Tyr Gly Arg Gly Pro Leu Gln Ile Ser Trp Asn Tyr Asn Tyr Gly Pro
145                 150                 155                 160

Ala Gly Arg Ala Ile Gly Phe Asp Gly Leu Gly Asp Pro Gly Arg Val
                165                 170                 175

Ala Arg Asp Ala Val Ala Phe Lys Ala Ala Leu Trp Phe Trp Met
            180                 185                 190

Asn Ser Val His Gly Val Val Pro Gln Gly Phe Gly Ala Thr Thr Arg
            195                 200                 205

Ala Ile Asn Gly Ala Leu Glu Cys Gly Gly Asn Asn Pro Ala Gln Met
210                 215                 220

Asn Ala Arg Val Gly Tyr Tyr Arg Gln Tyr Cys Arg Gln Leu Gly Val
225                 230                 235                 240

Asp Pro Gly Pro Asn Leu Thr Cys
                245

<210> SEQ ID NO 3
<211> LENGTH: 774
<212> TYPE: DNA
<213> ORGANISM: Unknown
<220> FEATURE:
<223> OTHER INFORMATION: Variant sequence produced by shuffling
      techniques r1B6 nucleic acid

<400> SEQUENCE: 3
tcgatgcaga actgcggctg ccagccaaac ttctgctgca gcaagttcgg ctactgcggc      60
acgaccgacg agtactgcgg cgacgggtgc cagtcgggcc cgtgccgctc gggcggcggc    120
ggcggcggcg gcggcggcgg aggcggcgga ggcagtggcg gtgcgaacgt ggctaatgta    180
gtcaccgacg cgttcttcaa cggcatcaag agccaggccg ggagcgggtg cgagggcaag    240
aacttctaca cccggagcgc gttcctgagc gccgtcaagg cgtacccagg cttcgcccat    300
ggcgggtcgc aggtgcaggg caagcgcgag atcgccgcct tcttcgcgca cgccacgcac    360
gagaccgggc atttctgcta catcaacgag atcgacgggc gagcaagaa ctactgcgac     420 cggaacaaca cgcagtggcc gtgccaggcg gggaaggggt actacggccg cggcccgctg    480
cagatctcct ggaacttcaa ctacgggccc gcggggaggg ccatcggctt cgacgggctc    540
ggggaccccg gcagggtggc gcgggacgcc gtggtggcgt tcaaggcggc gctctggttc    600
tggatgaaca gcgtgcacgg ggtgatgccg cagggcttcg cgccaccat cagggccatc     660 aacggcgccc tcgagtgcaa cgggaacaac cccgcccaga tgaacgcgcg cgtcggctac    720
tacaagcagt actgccagca gctccgcgtc gacccagggc caacctcac ttgc            774
```

```
<210> SEQ ID NO 4
<211> LENGTH: 258
<212> TYPE: PRT
<213> ORGANISM: Unknown
<220> FEATURE:
<223> OTHER INFORMATION: Variant sequence produced by shuffling
      techniques r1B6

<400> SEQUENCE: 4

Ser Met Gln Asn Cys Gly Cys Gln Pro Asn Phe Cys Cys Ser Lys Phe
  1               5                  10                  15

Gly Tyr Cys Gly Thr Thr Asp Glu Tyr Cys Gly Asp Gly Cys Gln Ser
             20                  25                  30

Gly Pro Cys Arg Ser Gly Gly Gly Gly Gly Gly Gly Gly Gly Gly Gly
         35                  40                  45

Gly Gly Gly Ser Gly Gly Ala Asn Val Ala Asn Val Val Thr Asp Ala
     50                  55                  60

Phe Phe Asn Gly Ile Lys Ser Gln Ala Gly Ser Gly Cys Glu Gly Lys
 65                  70                  75                  80

Asn Phe Tyr Thr Arg Ser Ala Phe Leu Ser Ala Val Lys Ala Tyr Pro
                 85                  90                  95

Gly Phe Ala His Gly Ser Gln Val Gln Gly Lys Arg Glu Ile Ala
            100                 105                 110

Ala Phe Phe Ala His Ala Thr His Glu Thr Gly His Phe Cys Tyr Ile
            115                 120                 125

Asn Glu Ile Asp Gly Pro Ser Lys Asn Tyr Cys Asp Arg Asn Asn Thr
130                 135                 140

Gln Trp Pro Cys Gln Ala Gly Lys Gly Tyr Tyr Gly Arg Gly Pro Leu
145                 150                 155                 160

Gln Ile Ser Trp Asn Phe Asn Tyr Gly Pro Ala Gly Arg Ala Ile Gly
                165                 170                 175

Phe Asp Gly Leu Gly Asp Pro Gly Arg Val Ala Arg Asp Ala Val Val
            180                 185                 190

Ala Phe Lys Ala Ala Leu Trp Phe Trp Met Asn Ser Val His Gly Val
            195                 200                 205

Met Pro Gln Gly Phe Gly Ala Thr Ile Arg Ala Ile Asn Gly Ala Leu
210                 215                 220

Glu Cys Asn Gly Asn Asn Pro Ala Gln Met Asn Ala Arg Val Gly Tyr
225                 230                 235                 240

Tyr Lys Gln Tyr Cys Gln Gln Leu Arg Val Asp Pro Gly Pro Asn Leu
                245                 250                 255

Thr Cys

<210> SEQ ID NO 5
<211> LENGTH: 753
<212> TYPE: DNA
<213> ORGANISM: Unknown
<220> FEATURE:
<223> OTHER INFORMATION: Variant sequence produced by shuffling
      techniques r1B10 nucleic acid

<400> SEQUENCE: 5
tcgatgcaga actgcggctg cgcgtcgggc ctgtgctgca gccggttcgg ctactgcggc      60
acgaccgacg cctactgcgg cgacgggtgc cagtcgggcc cgtgccgctc gggcggcggc     120
ggcagcagtg gcggcggtgg tgcgaacgtg gctagcgtcg tcaccggctc cttcttcaac     180
ggcatcaaga gccaggccgg gagcgggtgc gagggcaaga acttctacac ccggagcgcg     240
```

-continued

```
ttcctgagcg ccgtcaaggc gtacccaggc ttcgcccatg gcgggtcgga ggtggagggc    300
aagcgcgaga tcgccgcctt cttcgcgcac gtcacgcacg agaccgggca tttctgctac    360
atcaacgaga tcgacgggcc gagcaagaac tactgcgacc ggaacaacac gcagtggccg    420
tgccaggcgg ggaaggggta ctacggccgc ggcccgctgc agatctcgtg gaactacaac    480
tacgggcccg cggggagggc catcggcttc gacgggctcg ggacccccgg caggtggcg     540 cgggacgccg tggtggcgtt caaggcggcg ctctggttct ggatgaagaa catgcaccag    600
ctcatgcccc aggggttcgg cgccaccatc agggccatca acggcgccct cgagtgcaac    660
gggaacaacc ccgcccagat gaacgcgcgc gtcggctact acaggcagta ctgccgccag    720
ctcggcgtcg acccgggcaa caacctcacc tgc                                 753
```

<210> SEQ ID NO 6
<211> LENGTH: 251
<212> TYPE: PRT
<213> ORGANISM: Unknown
<220> FEATURE:
<223> OTHER INFORMATION: Variant sequence produced by shuffling techniques r1B10

<400> SEQUENCE: 6

```
Ser Met Gln Asn Cys Gly Cys Ala Ser Gly Leu Cys Cys Ser Arg Phe
  1               5                  10                  15

Gly Tyr Cys Gly Thr Thr Asp Ala Tyr Cys Gly Asp Gly Cys Gln Ser
                 20                  25                  30

Gly Pro Cys Arg Ser Gly Gly Gly Ser Ser Gly Gly Gly Ala
             35                  40                  45

Asn Val Ala Ser Val Val Thr Gly Ser Phe Phe Asn Gly Ile Lys Ser
 50                  55                  60

Gln Ala Gly Ser Gly Cys Glu Gly Lys Asn Phe Tyr Thr Arg Ser Ala
 65                  70                  75                  80

Phe Leu Ser Ala Val Lys Ala Tyr Pro Gly Phe Ala His Gly Gly Ser
                 85                  90                  95

Glu Val Glu Gly Lys Arg Glu Ile Ala Ala Phe Phe Ala His Val Thr
            100                 105                 110

His Glu Thr Gly His Phe Cys Tyr Ile Asn Glu Ile Asp Gly Pro Ser
            115                 120                 125

Lys Asn Tyr Cys Asp Arg Asn Asn Thr Gln Trp Pro Cys Gln Ala Gly
130                 135                 140

Lys Gly Tyr Tyr Gly Arg Gly Pro Leu Gln Ile Ser Trp Asn Tyr Asn
145                 150                 155                 160

Tyr Gly Pro Ala Gly Arg Ala Ile Gly Phe Asp Gly Leu Gly Asp Pro
                165                 170                 175

Gly Arg Val Ala Arg Asp Ala Val Ala Phe Lys Ala Ala Leu Trp
            180                 185                 190

Phe Trp Met Lys Asn Met His Gln Leu Met Pro Gln Gly Phe Gly Ala
            195                 200                 205

Thr Ile Arg Ala Ile Asn Gly Ala Leu Glu Cys Asn Gly Asn Asn Pro
    210                 215                 220

Ala Gln Met Asn Ala Arg Val Gly Tyr Tyr Arg Gln Tyr Cys Arg Gln
225                 230                 235                 240

Leu Gly Val Asp Pro Gly Asn Asn Leu Thr Cys
                245                 250
```

<210> SEQ ID NO 7

<211> LENGTH: 845
<212> TYPE: DNA
<213> ORGANISM: Unknown
<220> FEATURE:
<223> OTHER INFORMATION: Variant sequence produced by shuffling techniques r1D4 nucleic acid

<400> SEQUENCE: 7

```
tcgatgcaga actgcggctg ccagccgaac gtatgctgca gcaagtttgg ctactgcggc      60
acgaccgacg agtatcgatg cagaactgcg gctgccagcc gaacgtatgc tgcagcaagt     120
ttggctactg cggcacgacc gacgagtact cggcgacgg gtgccagtcg ggcccgtgcc     180
gctcgggcgg cggcggcggc ggcggcggcg gcggaggcgg cggaggcagt ggcggtgcga     240
acgtggctag cgtcgtcacc ggctccttct tcaacggcat caagagccag gccgggagcg     300
ggtgcgaggg caagaacttc tacacccgga gcgcgttcct gagcgccgtc aacgcgtacc     360
cgggcttcgc ccatggcggg acggaggtgg agggcaagcg cgagatcgcc gccttcttcg     420
cgcacgccac gcacgagacc gggcatttct gctacatcag cgagatcaac aagagcaacg     480
cctactgcga cgcgagcaac aggcagtggc cgtgcgcggc ggggcagaag tactacgggc     540
gcggcccgct gcagatctcg tggaactaca actacgggcc ggcggggagg agcctcggct     600
tcgacgggct gggcgacccc gacgcggtgg cgcgcagcgc cgtgctcgcg ttccgctccg     660
cgctctggta ctggatgaac aacgtgcacg gggtggtgcc gcaggggttc ggcgccacca     720
ccagggccat caacggcgcc ctcgagtgca cgggaacaa cccgcccag atgaacgcgc     780
gcgtcggcta ctacaggcag tactgccgcc agctcggcgt cgaccccggg cccaacctca     840
cctgc                                                                 845
```

<210> SEQ ID NO 8
<211> LENGTH: 257
<212> TYPE: PRT
<213> ORGANISM: Unknown
<220> FEATURE:
<223> OTHER INFORMATION: Variant sequence produced by shuffling techniques r1D4

<400> SEQUENCE: 8

```
Ser Met Gln Asn Cys Gly Cys Gln Pro Asn Val Cys Cys Ser Lys Phe
1               5                   10                  15
Gly Tyr Cys Gly Thr Thr Asp Glu Tyr Cys Gly Asp Gly Cys Gln Ser
            20                  25                  30
Gly Pro Cys Arg Ser Gly Gly Gly Gly Gly Gly Gly Gly Gly Gly Gly
        35                  40                  45
Gly Gly Gly Ser Gly Gly Ala Asn Val Ala Ser Val Val Thr Gly Ser
    50                  55                  60
Phe Phe Asn Gly Ile Lys Ser Gln Ala Gly Ser Gly Cys Glu Gly Lys
65                  70                  75                  80
Asn Phe Tyr Thr Arg Ser Ala Phe Leu Ser Ala Val Asn Ala Tyr Pro
                85                  90                  95
Gly Phe Ala His Gly Gly Thr Glu Val Glu Gly Lys Arg Glu Ile Ala
            100                 105                 110
Ala Phe Phe Ala His Ala Thr His Glu Thr Gly His Phe Cys Tyr Ile
        115                 120                 125
Ser Glu Ile Asn Lys Ser Asn Ala Tyr Cys Asp Ala Ser Asn Arg Gln
    130                 135                 140
Trp Pro Cys Ala Ala Gly Gln Lys Tyr Tyr Gly Arg Gly Pro Leu Gln
145                 150                 155                 160
```

```
Ile Ser Trp Asn Tyr Asn Tyr Gly Pro Ala Gly Arg Ser Leu Gly Phe
            165                 170                 175

Asp Gly Leu Gly Asp Pro Asp Ala Val Ala Arg Ser Ala Val Leu Ala
        180                 185                 190

Phe Arg Ser Ala Leu Trp Tyr Trp Met Asn Asn Val His Gly Val Val
    195                 200                 205

Pro Gln Gly Phe Gly Ala Thr Thr Arg Ala Ile Asn Gly Ala Leu Glu
    210                 215                 220

Cys Asn Gly Asn Asn Pro Ala Gln Met Asn Ala Arg Val Gly Tyr Tyr
225                 230                 235                 240

Arg Gln Tyr Cys Arg Gln Leu Gly Val Asp Pro Gly Pro Asn Leu Thr
                245                 250                 255

Cys

<210> SEQ ID NO 9
<211> LENGTH: 753
<212> TYPE: DNA
<213> ORGANISM: Unknown
<220> FEATURE:
<223> OTHER INFORMATION: Variant sequence produced by shuffling
      techniques r2A2 nucleic acid

<400> SEQUENCE: 9
tcgacgcaga actgcggctg cgcgtcgggc ctgtgctgca gccggttcgg ctactgcggc      60
acgaccgacg cctactgcgg cgacgggtgc cagtcgggcc cgtgccgctc gggcggcggc     120
ggcagcagtg gcggcggtgg tgcgaacgtg gctagcgtcg tcaccggctc cttcttcaac     180
ggcatcaaga gccaggccgg gagcgggtgc gagggcaaga atttctacac ccggagcgcg     240
ttcctgagcg ccgtcaaggc gtacccaggc ttcgcccatg gcgggtcgga ggtggagggc     300
aagcgcgaga tcgccgcctt cttcgcgcac gtcacgcacg agaccgggca tttctgctac     360
atcaacgaga tcgacgggcc gagcaagaac tactgcgacc ggaacaacac gcagtggccg     420
tgccaggcgg ggaagggta ctacggccgc ggcccgctgc agatctcgtg gaactacaac      480
tacgggcccg cggggagggc catcggcttc gacgggctcg ggaccccgg cagggtggcg      540 cgggacgccg tggtggcgtt caaggcggcg ctctggttct ggatgaagaa catgcaccag     600
ctcatgcccc aggggttcgg cgccaccatc agggccatca cggcgccct cgagtgcaac      660 gggaacaacc ccgcccagat gaacgcgcgc gtcggctact acaggcagta ctgccgccag     720
ctcggcgtcg acccgggcaa caacctcacc tgc                                   753

<210> SEQ ID NO 10
<211> LENGTH: 251
<212> TYPE: PRT
<213> ORGANISM: Unknown
<220> FEATURE:
<223> OTHER INFORMATION: Variant sequence produced by shuffling
      techniques r2A2

<400> SEQUENCE: 10

Ser Thr Gln Asn Cys Gly Cys Ala Ser Gly Leu Cys Cys Ser Arg Phe
  1               5                  10                  15

Gly Tyr Cys Gly Thr Thr Asp Ala Tyr Cys Gly Asp Gly Cys Gln Ser
               20                  25                  30

Gly Pro Cys Arg Ser Gly Gly Gly Ser Ser Gly Gly Gly Ala
           35                  40                  45

Asn Val Ala Ser Val Val Thr Gly Ser Phe Phe Asn Gly Ile Lys Ser
```

-continued

```
                50                    55                   60
Gln Ala Gly Ser Gly Cys Glu Gly Lys Asn Phe Thr Arg Ser Ala
 65                  70                  75                  80

Phe Leu Ser Ala Val Lys Ala Tyr Pro Gly Phe Ala His Gly Ser
                 85                  90                  95

Glu Val Glu Gly Lys Arg Glu Ile Ala Ala Phe Phe Ala His Val Thr
            100                 105                 110

His Glu Thr Gly His Phe Cys Tyr Ile Asn Glu Ile Asp Gly Pro Ser
            115                 120                 125

Lys Asn Tyr Cys Asp Arg Asn Asn Thr Gln Trp Pro Cys Gln Ala Gly
130                 135                 140

Lys Gly Tyr Tyr Gly Arg Gly Pro Leu Gln Ile Ser Trp Asn Tyr Asn
145                 150                 155                 160

Tyr Gly Pro Ala Gly Arg Ala Ile Gly Phe Asp Gly Leu Gly Asp Pro
                165                 170                 175

Gly Arg Val Ala Arg Asp Ala Val Val Ala Phe Lys Ala Ala Leu Trp
                180                 185                 190

Phe Trp Met Lys Asn Met His Gln Leu Met Pro Gln Gly Phe Gly Ala
            195                 200                 205

Thr Ile Arg Ala Ile Asn Gly Ala Leu Glu Cys Asn Gly Asn Asn Pro
        210                 215                 220

Ala Gln Met Asn Ala Arg Val Gly Tyr Tyr Arg Gln Tyr Cys Arg Gln
225                 230                 235                 240

Leu Gly Val Asp Pro Gly Asn Asn Leu Thr Cys
                245                 250
```

<210> SEQ ID NO 11
<211> LENGTH: 771
<212> TYPE: DNA
<213> ORGANISM: Unknown
<220> FEATURE:
<223> OTHER INFORMATION: Variant sequence produced by shuffling
      techniques r2C2 nucleic acid

<400> SEQUENCE: 11

```
tcgatgcaga actgcggctg ccagccaaac gtatgctgca gcaagtttgg ctactgcggc      60
acgaccgacg agtactgcgg cgacgggtgc cagtcgggcc cgtgccgctc gggcggcggt     120
ggcggcggcg gcggcggcgg aggcggcgga ggcagtggcg gtgcgaacgt ggctaatgtg     180
gtcaccgacg cgttcttcaa cggcatcaag aaccaggccg ggagcgggtg cgagggcaag     240
aacttctaca cccggagcgc gttcctcgag gccatcgccg cgtacccggg cttcgcgcat     300
ggcggctccg aggtcgagcg caagcgcgag attgccgcct tcttcgcgca cgccacgcac     360
gagaccgggc atttctgcta catcagcgag gtcaacaaga gcaacgccta ctgcgacccg     420
accaagaggc agtggccgtg cgccgcgggg cagaagtact acgggcgcgg cccgctgcag     480
atctcgtgga actacaacta cgggcccgcg gggagggcca tcggcttcga cgggctcggg     540
gaccccggca gggtggcgcg ggacgccgtg gtggcgttca aggcggcgct ctggttctgg     600
atgaacaacg tgcaccgtgt gatgccgcag ggcttcggcg ccaccatcag ggccatcaac     660
ggcgccctcg agtgcaacgg gaacaacccc gcccagatga acgcgcgcgt cggctactac     720
aggcagtact gccgccagct cggcgtcgac ccgggcaaca acctcacctg c              771
```

<210> SEQ ID NO 12
<211> LENGTH: 257
<212> TYPE: PRT

<213> ORGANISM: Unknown
<220> FEATURE:
<223> OTHER INFORMATION: Variant sequence produced by shuffling
      techniques r2C2

<400> SEQUENCE: 12

Ser Met Gln Asn Cys Gly Cys Gln Pro Asn Val Cys Cys Ser Lys Phe
1               5                   10                  15

Gly Tyr Cys Gly Thr Thr Asp Glu Tyr Cys Gly Asp Gly Cys Gln Ser
            20                  25                  30

Gly Pro Cys Arg Ser Gly Gly Gly Gly Gly Gly Gly Gly Gly Gly Gly
        35                  40                  45

Gly Gly Gly Ser Gly Gly Ala Asn Val Ala Asn Val Thr Asp Ala
    50                  55                  60

Phe Phe Asn Gly Ile Lys Asn Gln Ala Gly Ser Gly Cys Glu Gly Lys
65                  70                  75                  80

Asn Phe Tyr Thr Arg Ser Ala Phe Leu Glu Ala Ile Ala Ala Tyr Pro
                85                  90                  95

Gly Phe Ala His Gly Gly Ser Glu Val Glu Arg Lys Arg Glu Ile Ala
            100                 105                 110

Ala Phe Phe Ala His Ala Thr His Glu Thr Gly His Phe Cys Tyr Ile
        115                 120                 125

Ser Glu Val Asn Lys Ser Asn Ala Tyr Cys Asp Pro Thr Lys Arg Gln
130                 135                 140

Trp Pro Cys Ala Ala Gly Gln Lys Tyr Tyr Gly Arg Gly Pro Leu Gln
145                 150                 155                 160

Ile Ser Trp Asn Tyr Asn Tyr Gly Pro Ala Gly Arg Ala Ile Gly Phe
                165                 170                 175

Asp Gly Leu Gly Asp Pro Gly Arg Val Ala Arg Asp Ala Val Val Ala
            180                 185                 190

Phe Lys Ala Ala Leu Trp Phe Trp Met Asn Asn Val His Arg Val Met
        195                 200                 205

Pro Gln Gly Phe Gly Ala Thr Ile Arg Ala Ile Asn Gly Ala Leu Glu
210                 215                 220

Cys Asn Gly Asn Asn Pro Ala Gln Met Asn Ala Arg Val Gly Tyr Tyr
225                 230                 235                 240

Arg Gln Tyr Cys Arg Gln Leu Gly Val Asp Pro Gly Asn Asn Leu Thr
                245                 250                 255

Cys

<210> SEQ ID NO 13
<211> LENGTH: 753
<212> TYPE: DNA
<213> ORGANISM: Unknown
<220> FEATURE:
<223> OTHER INFORMATION: Variant sequence produced by shuffling
      techniques r2E1 nucleic acid

<400> SEQUENCE: 13
tcgatgcaga actgcggctg cgcgtcgggc ctgtgctgca gccggttcgg ctactgcggc      60
acgaccgacg cctactgcgg cgacgggtgc cagtcgggcc cgtgccgctc gggcggcggc     120
ggcagcagtg gcggcggtgg tgcgaacgtg gctagcgtcg tcaccggctc cttcttcaac     180
ggcatcaaga gccaggccgg gagcgggtgc gagggcaaga acttctacac ccggagcgcg     240
ttcctgagcg ccgtcaaggc gtacccaggc ttcgcccatg gcgggtcgga ggtgagggc      300 aagcgcgaga tcgccgcctt cttcgcgcac gtcacgcacg agaccgggca tttctgctac     360

```
atcaacgaga tcgacgggcc gagcaagaac tactgcgacc ggaacaacac gcagtggccg      420
tgccaggcgg ggaaggggta ctacggccgc ggcccgctgc agatctcgtg gaactacaac      480
tacgggcccg cggggagggc catcggcttc gacgggctcg ggaccccgg cagggtggcg       540 cgggacgccg tggtggcgtt caaggcggcg ctctggttct ggatgaagaa catccaccag      600
ctcatgcccc aggggttcgg cgccaccatc agggccatca acggcgccct cgagtgcaac      660
gggaacaacc ccgcccagat gaacgcgcgc gtcggctact acaggcagta ctgccgccag      720
ctcggcgtcg acccgggcaa caacctcacc tgc                                   753
```

<210> SEQ ID NO 14
<211> LENGTH: 251
<212> TYPE: PRT
<213> ORGANISM: Unknown
<220> FEATURE:
<223> OTHER INFORMATION: Variant sequence produced by shuffling techniques r2E1

<400> SEQUENCE: 14

```
Ser Met Gln Asn Cys Gly Cys Ala Ser Gly Leu Cys Cys Ser Arg Phe
 1               5                  10                  15

Gly Tyr Cys Gly Thr Thr Asp Ala Tyr Cys Gly Asp Gly Cys Gln Ser
             20                  25                  30

Gly Pro Cys Arg Ser Gly Gly Gly Ser Ser Gly Gly Gly Gly Ala
         35                  40                  45

Asn Val Ala Ser Val Val Thr Gly Ser Phe Phe Asn Gly Ile Lys Ser
 50                  55                  60

Gln Ala Gly Ser Gly Cys Glu Gly Lys Asn Phe Tyr Thr Arg Ser Ala
 65                  70                  75                  80

Phe Leu Ser Ala Val Lys Ala Tyr Pro Gly Phe Ala His Gly Gly Ser
                 85                  90                  95

Glu Val Glu Gly Lys Arg Glu Ile Ala Ala Phe Ala His Val Thr
            100                 105                 110

His Glu Thr Gly His Phe Cys Tyr Ile Asn Glu Ile Asp Gly Pro Ser
        115                 120                 125

Lys Asn Tyr Cys Asp Arg Asn Asn Thr Gln Trp Pro Cys Gln Ala Gly
130                 135                 140

Lys Gly Tyr Tyr Gly Arg Gly Pro Leu Gln Ile Ser Trp Asn Tyr Asn
145                 150                 155                 160

Tyr Gly Pro Ala Gly Arg Ala Ile Gly Phe Asp Gly Leu Gly Asp Pro
                165                 170                 175

Gly Arg Val Ala Arg Asp Ala Val Val Ala Phe Lys Ala Ala Leu Trp
            180                 185                 190

Phe Trp Met Lys Asn Ile His Gln Leu Met Pro Gln Gly Phe Gly Ala
        195                 200                 205

Thr Ile Arg Ala Ile Asn Gly Ala Leu Glu Cys Asn Gly Asn Asn Pro
    210                 215                 220

Ala Gln Met Asn Ala Arg Val Gly Tyr Tyr Arg Gln Tyr Cys Arg Gln
225                 230                 235                 240

Leu Gly Val Asp Pro Gly Asn Asn Leu Thr Cys
                245                 250
```

<210> SEQ ID NO 15
<211> LENGTH: 774
<212> TYPE: DNA
<213> ORGANISM: Unknown

-continued

```
<220> FEATURE:
<223> OTHER INFORMATION: Variant sequence produced by shuffling
      techniques r2H2 nucleic acid

<400> SEQUENCE: 15
tcgatgcaga actgcggctg ccagccaaac gtatgctgca gcaagttcgg ctactgcggc      60
acgaccgacg agtactgcgg cgacgggtgc cagtcaggcc cgtgccgctc gggcggcggt     120
ggcggcggcg gcggcggcgg aggcggcgga ggcagtggcg gggcgaacgt ggctagcgtc     180
gtcaccggct ccttcttcaa cggcatcaag agccaggccg ggagcgggtg cgagggcaag     240
aacttctaca cccggagcgc gttcctgagc gccgtcaagg cgtacccagg cttcgcccat     300
ggcgggtcgg aggtggaggg caagcgcgag atcgccgcct tcttcgcgca cgtcacgcac     360
gagaccgggc atttctgcta catcaacgag atcgacgggc cgagcaagaa ctactgcgac     420
cggaacaaca cgcagtggcc cgtgccaggcg gggaagggggt actacggccg cggcccgctg     480
cagatctcgt ggaactacaa ctacgggccc gcggggaggg ccatcggctt cgacgggctc     540
ggggaccccg gcagggtggc gcgggacgcc gtggtagcgt tcaaggcggc gctctggttc     600
tggatgaaga acatgcacca gctcatgccc caggggttcg cgccaccat cagggccatc      660 aacggcgccc tcgagtgcaa cgggaacaac cccgcccaga tgaacgcgcg cgtcggctac     720
tacaggcagt actgccgcca gctcggcgtc gacccgggca caacctcac ctgc            774

<210> SEQ ID NO 16
<211> LENGTH: 258
<212> TYPE: PRT
<213> ORGANISM: Unknown
<220> FEATURE:
<223> OTHER INFORMATION: Variant sequence produced by shuffling
      techniques r2H2

<400> SEQUENCE: 16

Ser Met Gln Asn Cys Gly Cys Gln Pro Asn Val Cys Cys Ser Lys Phe
 1               5                  10                  15

Gly Tyr Cys Gly Thr Thr Asp Glu Tyr Cys Gly Asp Gly Cys Gln Ser
            20                  25                  30

Gly Pro Cys Arg Ser Gly Gly Gly Gly Gly Gly Gly Gly Gly Gly Gly
        35                  40                  45

Gly Gly Gly Ser Gly Gly Ala Asn Val Ala Ser Val Val Thr Gly Ser
    50                  55                  60

Phe Phe Asn Gly Ile Lys Ser Gln Ala Gly Ser Gly Cys Glu Gly Lys
65                  70                  75                  80

Asn Phe Tyr Thr Arg Ser Ala Phe Leu Ser Ala Val Lys Ala Tyr Pro
                85                  90                  95

Gly Phe Ala His Gly Gly Ser Glu Val Glu Gly Lys Arg Glu Ile Ala
            100                 105                 110

Ala Phe Phe Ala His Val Thr His Glu Thr Gly His Phe Cys Tyr Ile
        115                 120                 125

Asn Glu Ile Asp Gly Pro Ser Lys Asn Tyr Cys Asp Arg Asn Asn Thr
    130                 135                 140

Gln Trp Pro Cys Gln Ala Gly Lys Gly Tyr Tyr Gly Arg Gly Pro Leu
145                 150                 155                 160

Gln Ile Ser Trp Asn Tyr Asn Tyr Gly Pro Ala Gly Arg Ala Ile Gly
                165                 170                 175

Phe Asp Gly Leu Gly Asp Pro Gly Arg Val Ala Arg Asp Ala Val Val
            180                 185                 190
```

```
Ala Phe Lys Ala Ala Leu Trp Phe Trp Met Lys Asn Met His Gln Leu
            195                 200                 205

Met Pro Gln Gly Phe Gly Ala Thr Ile Arg Ala Ile Asn Gly Ala Leu
210                 215                 220

Glu Cys Asn Gly Asn Asn Pro Ala Gln Met Asn Ala Arg Val Gly Tyr
225                 230                 235                 240

Tyr Arg Gln Tyr Cys Arg Gln Leu Gly Val Asp Pro Gly Asn Asn Leu
            245                 250                 255

Thr Cys

<210> SEQ ID NO 17
<211> LENGTH: 280
<212> TYPE: PRT
<213> ORGANISM: Unknown
<220> FEATURE:
<223> OTHER INFORMATION: Chitinase A, M84164

<400> SEQUENCE: 17

Met Ala Asn Ala Pro Arg Ile Leu Ala Leu Gly Leu Leu Ala Leu Leu
1               5                   10                  15

Cys Ala Ala Ala Gly Pro Ala Ala Gln Asn Cys Gly Cys Gln Pro
            20                  25                  30

Asn Phe Cys Cys Ser Lys Phe Gly Tyr Cys Gly Thr Thr Asp Ala Tyr
            35                  40                  45

Cys Gly Asp Gly Cys Gln Ser Gly Pro Cys Arg Ser Gly Gly Gly Gly
    50                  55                  60

Gly Gly Gly Gly Gly Gly Gly Gly Ser Gly Gly Ala Asn Val
65                  70                  75                  80

Ala Asn Val Val Thr Asp Ala Phe Phe Asn Gly Ile Lys Asn Gln Ala
                85                  90                  95

Gly Ser Gly Cys Glu Gly Lys Asn Phe Tyr Thr Arg Ser Ala Phe Leu
            100                 105                 110

Ser Ala Val Asn Ala Tyr Pro Gly Phe Ala His Gly Gly Thr Glu Val
        115                 120                 125

Glu Gly Lys Arg Glu Ile Ala Ala Phe Ala His Val Thr His Glu
130                 135                 140

Thr Gly His Phe Cys Tyr Ile Ser Glu Ile Asn Lys Ser Asn Ala Tyr
145                 150                 155                 160

Cys Asp Ala Ser Asn Arg Gln Trp Pro Cys Ala Ala Gly Gln Lys Tyr
                165                 170                 175

Tyr Gly Arg Gly Pro Leu Gln Ile Ser Trp Asn Tyr Asn Tyr Gly Pro
            180                 185                 190

Ala Gly Arg Asp Ile Gly Phe Asn Gly Leu Ala Asp Pro Asn Arg Val
        195                 200                 205

Ala Gln Asp Ala Val Ile Ala Phe Lys Thr Ala Leu Trp Phe Trp Met
210                 215                 220

Asn Asn Val His Gly Val Met Pro Gln Gly Phe Gly Ala Thr Ile Arg
225                 230                 235                 240

Ala Ile Asn Gly Ala Leu Glu Cys Asn Gly Asn Asn Pro Ala Gln Met
                245                 250                 255

Asn Ala Arg Val Gly Tyr Tyr Lys Gln Tyr Cys Gln Gln Leu Arg Val
            260                 265                 270

Asp Pro Gly Pro Asn Leu Ile Cys
        275                 280
```

-continued

```
<210> SEQ ID NO 18
<211> LENGTH: 269
<212> TYPE: PRT
<213> ORGANISM: Unknown
<220> FEATURE:
<223> OTHER INFORMATION: Chitinase B, M84165

<400> SEQUENCE: 18

Pro Gln Leu Val Ala Leu Gly Leu Ala Leu Leu Cys Ala Val Ala Gly
 1               5                  10                  15

Pro Ala Ala Ala Gln Asn Cys Gly Cys Gln Pro Asn Val Cys Cys Ser
                20                  25                  30

Lys Phe Gly Tyr Cys Gly Thr Thr Asp Glu Tyr Cys Gly Asp Gly Cys
            35                  40                  45

Gln Ser Gly Pro Cys Arg Ser Arg Gly Gly Gly Ser Gly Gly
    50                  55                  60

Gly Gly Ala Asn Val Ala Ser Val Val Thr Ser Ser Phe Phe Asn Gly
65                  70                  75                  80

Ile Lys Asn Gln Ala Gly Ser Gly Cys Glu Gly Lys Asn Phe Tyr Thr
                85                  90                  95

Arg Ser Ala Phe Leu Ser Ala Val Lys Gly Tyr Pro Gly Phe Ala His
            100                 105                 110

Gly Gly Ser Gln Val Gln Gly Lys Arg Glu Ile Ala Ala Phe Phe Ala
        115                 120                 125

His Ala Thr His Glu Thr Gly His Phe Cys Tyr Ile Ser Glu Ile Asn
    130                 135                 140

Lys Ser Asn Ala Tyr Cys Asp Pro Thr Lys Arg Gln Trp Pro Cys Ala
145                 150                 155                 160

Ala Gly Gln Lys Tyr Tyr Gly Arg Gly Pro Leu Gln Ile Ser Trp Asn
                165                 170                 175

Tyr Asn Tyr Gly Pro Ala Gly Arg Ala Ile Gly Phe Asp Gly Leu Gly
            180                 185                 190

Asp Pro Gly Arg Val Ala Arg Asp Ala Val Val Ala Phe Lys Ala Ala
        195                 200                 205

Leu Trp Phe Trp Met Asn Ser Val His Gly Val Val Pro Gln Gly Phe
    210                 215                 220

Gly Ala Thr Thr Arg Ala Met Gln Arg Ala Leu Glu Cys Gly Gly Asn
225                 230                 235                 240

Asn Pro Ala Gln Met Asn Ala Arg Val Gly Tyr Tyr Arg Gln Tyr Cys
                245                 250                 255

Arg Gln Leu Gly Val Asp Pro Gly Pro Asn Leu Thr Cys
            260                 265

<210> SEQ ID NO 19
<211> LENGTH: 280
<212> TYPE: PRT
<213> ORGANISM: Unknown
<220> FEATURE:
<223> OTHER INFORMATION: Chitinase A, Huynh et al.

<400> SEQUENCE: 19

Met Ala Asn Ala Pro Arg Ile Leu Ala Leu Gly Leu Ala Leu Leu
 1               5                  10                  15

Cys Ala Ala Ala Gly Pro Ala Ala Ala Gln Asn Cys Gly Cys Gln Pro
                20                  25                  30

Asn Phe Cys Cys Ser Lys Phe Gly Tyr Cys Gly Thr Thr Asp Ala Tyr
            35                  40                  45
```

```
Cys Gly Asp Gly Cys Gln Ser Gly Pro Cys Arg Ser Gly Gly Gly
         50                  55                  60
Gly Gly Gly Gly Gly Gly Gly Gly Ser Gly Gly Ala Asn Val
65                  70                  75                  80
Ala Asn Val Val Thr Asp Ala Phe Phe Asn Gly Ile Lys Asn Gln Ala
                 85                  90                  95
Gly Ser Gly Cys Glu Gly Lys Asn Phe Tyr Thr Arg Ser Ala Phe Leu
            100                 105                 110
Ser Ala Val Asn Ala Tyr Pro Gly Phe Ala His Gly Gly Thr Glu Val
            115                 120                 125
Glu Gly Lys Arg Glu Ile Ala Ala Phe Phe Ala His Val Thr His Glu
            130                 135                 140
Thr Gly His Phe Cys Tyr Ile Ser Glu Ile Asn Lys Ser Asn Ala Tyr
145                 150                 155                 160
Cys Asp Ala Ser Asn Arg Gln Trp Pro Cys Ala Ala Gly Gln Lys Tyr
                165                 170                 175
Tyr Gly Arg Gly Pro Leu Gln Ile Ser Trp Asn Tyr Asn Tyr Gly Pro
            180                 185                 190
Ala Gly Arg Asp Ile Gly Phe Asn Gly Leu Ala Asp Pro Asn Arg Val
            195                 200                 205
Ala Gln Asp Ala Val Ile Ala Phe Lys Thr Ala Leu Trp Phe Trp Met
            210                 215                 220
Asn Asn Val His Arg Val Met Pro Gln Gly Phe Gly Ala Thr Ile Arg
225                 230                 235                 240
Ala Ile Asn Gly Ala Leu Glu Cys Asn Gly Asn Pro Ala Gln Met
                245                 250                 255
Asn Ala Arg Val Gly Tyr Tyr Lys Gln Tyr Cys Gln Gln Leu Arg Val
                260                 265                 270
Asp Pro Gly Pro Asn Leu Ile Cys
            275                 280

<210> SEQ ID NO 20
<211> LENGTH: 270
<212> TYPE: PRT
<213> ORGANISM: Unknown
<220> FEATURE:
<223> OTHER INFORMATION: Chitinase B, Huynh et al.

<400> SEQUENCE: 20

Pro Gln Leu Val Ala Leu Gly Leu Ala Leu Leu Cys Ala Val Ala Gly
 1               5                  10                  15
Pro Ala Ala Ala Gln Asn Cys Gly Cys Gln Pro Asn Val Cys Cys Ser
                 20                  25                  30
Lys Phe Gly Tyr Cys Gly Thr Thr Asp Glu Tyr Cys Gly Asp Gly Cys
             35                  40                  45
Gln Ser Gly Pro Cys Arg Ser Arg Gly Gly Gly Ser Gly Gly
         50                  55                  60
Gly Gly Ala Asn Val Ala Ser Val Val Thr Ser Ser Phe Phe Asn Gly
65                  70                  75                  80
Ile Lys Asn Gln Ala Gly Ser Gly Cys Glu Gly Lys Asn Phe Tyr Thr
                 85                  90                  95
Arg Ser Ala Phe Leu Ser Ala Val Asn Lys Gly Tyr Pro Gly Phe Ala
            100                 105                 110
His Gly Gly Ser Gln Val Gln Gly Lys Arg Glu Ile Ala Ala Phe Phe
            115                 120                 125
```

```
Ala His Ala Thr His Glu Thr Gly His Phe Cys Tyr Ile Ser Glu Ile
    130                 135                 140

Asn Lys Ser Asn Ala Tyr Cys Asp Pro Thr Lys Arg Gln Trp Pro Cys
145                 150                 155                 160

Ala Ala Gly Gln Lys Tyr Tyr Gly Arg Gly Pro Leu Gln Ile Ser Trp
                165                 170                 175

Asn Tyr Asn Tyr Gly Pro Ala Gly Arg Ala Ile Gly Phe Asp Gly Leu
            180                 185                 190

Phe Asp Pro Phe Arg Val Ala Arg Asp Ala Val Ala Phe Lys Ala
        195                 200                 205

Ala Leu Trp Phe Trp Met Asn Ser Val His Gly Val Val Pro Gln Gly
    210                 215                 220

Phe Gly Ala Thr Thr Arg Ala Ile Asn Gly Ala Leu Glu Cys Gly Gly
225                 230                 235                 240

Asn Asn Pro Ala Gln Met Asn Ala Arg Val Gly Tyr Tyr Arg Gln Tyr
                245                 250                 255

Cys Arg Gln Leu Gly Val Asp Pro Gly Pro Asn Leu Thr Cys
            260                 265                 270

<210> SEQ ID NO 21
<211> LENGTH: 750
<212> TYPE: DNA
<213> ORGANISM: Unknown
<220> FEATURE:
<223> OTHER INFORMATION: Variant sequence produced by shuffling
      techniques 4M1/11_C10 nucleic acid

<400> SEQUENCE: 21
tcgatgcaga actgcgggtg cgcgtcgggc ctgtgctgca gccggttcgg gtactgcggc      60
acgaccgacg agtactgcgg cgacgggtgc cagtcgggcc cgtgccgctc gggcggcggc     120
ggcagcagtg gcggcggtgg tgcgaacgtg gctagcgtcg tcaccggctc cttcttcaac     180
ggcatcaaga gccaggccgg gagcgggtgc gagggcaaga acttctacac ccggagcgcg     240
ttcctgagcg ccgtcaaggc gtacccaggc ttcgcccatg gcgggtcgca ggtgcagggc     300
aagcgcgaga tcgccgcctt cttcgcgcac gccacgcacg agaccgggca tttctgctac     360
atcagcgaga tcaacaagag caacgcctac tgcgacccga ccaagaggca gtggccgtgc     420 gccgcgggc agaagtacta cgggcgcggc ccgctgcaga tctcgtggaa ctacaactac     480
gggcccgcgg ggagggccat cggcttcgac gggctcgggg accccggcag ggtggcgcgg     540
gacgccgtgg tggcgttcaa ggcggcgctc tggttctgga tgaacaacgt gcaccgtgtg     600
atgccgcagg gcttcggcgc caccatcagg gccatcaacg gcgcgctcga gtgcaacggg     660
aacaaccccg cccagatgaa cgcgcgcgtc ggctactaca gcagtactg ccagcagctc     720 cgcgtcgacc cagggcccaa cctcacctgc                                     750

<210> SEQ ID NO 22
<211> LENGTH: 250
<212> TYPE: PRT
<213> ORGANISM: Unknown
<220> FEATURE:
<223> OTHER INFORMATION: Variant sequence produced by shuffling
      techniques 4M1/11_C10

<400> SEQUENCE: 22

Ser Met Gln Asn Cys Gly Cys Ala Ser Gly Leu Cys Cys Ser Arg Phe
  1               5                  10                  15

Gly Tyr Cys Gly Thr Thr Asp Glu Tyr Cys Gly Asp Gly Cys Gln Ser
```

```
                    20                  25                  30
Gly Pro Cys Arg Ser Gly Gly Gly Ser Ser Gly Gly Gly Ala
        35                  40                  45
Asn Val Ala Ser Val Val Thr Gly Ser Phe Phe Asn Gly Ile Lys Ser
 50                      55                  60
Gln Ala Gly Ser Gly Cys Glu Gly Lys Asn Phe Tyr Thr Arg Ser Ala
 65                  70                  75                  80
Phe Leu Ser Ala Val Lys Ala Tyr Pro Gly Phe Ala His Gly Gly Ser
                 85                  90                  95
Gln Val Gln Gly Lys Arg Glu Ile Ala Ala Phe Ala His Ala Thr
            100                 105                 110
His Glu Thr Gly His Phe Cys Tyr Ile Ser Glu Ile Asn Lys Ser Asn
        115                 120                 125
Ala Tyr Cys Asp Pro Thr Lys Arg Gln Trp Pro Cys Ala Ala Gly Gln
        130                 135                 140
Lys Tyr Tyr Gly Arg Gly Pro Leu Gln Ile Ser Trp Asn Tyr Asn Tyr
145                 150                 155                 160
Gly Pro Ala Gly Arg Ala Ile Gly Phe Asp Gly Leu Gly Asp Pro Gly
                165                 170                 175
Arg Val Ala Arg Asp Ala Val Val Ala Phe Lys Ala Ala Leu Trp Phe
            180                 185                 190
Trp Met Asn Asn Val His Arg Val Met Pro Gln Gly Phe Gly Ala Thr
        195                 200                 205
Ile Arg Ala Ile Asn Gly Ala Leu Glu Cys Asn Gly Asn Asn Pro Ala
        210                 215                 220
Gln Met Asn Ala Arg Val Gly Tyr Tyr Lys Gln Tyr Cys Gln Gln Leu
225                 230                 235                 240
Arg Val Asp Pro Gly Pro Asn Leu Thr Cys
                245                 250

<210> SEQ ID NO 23
<211> LENGTH: 771
<212> TYPE: DNA
<213> ORGANISM: Unknown
<220> FEATURE:
<223> OTHER INFORMATION: Variant sequence produced by shuffling
      techniques 4M1/1_H2 nucleic acid

<400> SEQUENCE: 23
tcgatgcaga actgcggctg ccagccaaac gtatgctgca gcaagtttgg ctactgcggc      60
acgaccgacg agtactgcgg cgacgggtgc cagtcgggcc cgtgccgctc gggcggcggc     120
ggcagcagtg gcggcggcgg aggcggcgga ggcagtggcg gtgcgaacgt ggctaatgtg     180
gtcaccgacg cgttcttcaa cggcatcaag aaccaggccg ggagctggtg cgagggcaag     240
aacttctaca cccggagcgc gttcctgagc gccgtcaagg cgtacccagg cttcgcccat     300
ggcgggtcgc aggtgcaggg caagcgcgag atcgccgcct tcttcgcgca tgtcacgcac     360
gagaccgggc atttgtgcta catcaacgag gtcaacaaga gcaacgccta ctgcgacccg     420
accaagaggc agtggccgtg cgccgcgggg cagaagtact acgggcgcgg cccgctgcag     480
atctcgtgga actacaacta cgggcccgcg gggagggcca tcggcttcga cgggctggga     540
gacccggaca gactggcgca ggaccccgtg ttgtcgttca gtcggcgctc tggttctgg      600 atgaacaacg tgcaccgtgt gatgccgcag ggcttcggcg ccaccatcag ggccatcaac     660
ggcgccctcg agtgcggcgg gaacaacccc gcccagatga acgcgcgcgt cggctactac     720
```

```
aggcagtact gccgccagct cggcgtcgac ccgggcaaca acctcacctg c          771
```

<210> SEQ ID NO 24
<211> LENGTH: 257
<212> TYPE: PRT
<213> ORGANISM: Unknown
<220> FEATURE:
<223> OTHER INFORMATION: Variant sequence produced by shuffling
      techniques 4M1/1_H2

<400> SEQUENCE: 24

```
Ser Met Gln Asn Cys Gly Cys Gln Pro Asn Val Cys Cys Ser Lys Phe
  1               5                  10                  15

Gly Tyr Cys Gly Thr Thr Asp Glu Tyr Cys Gly Asp Gly Cys Gln Ser
             20                  25                  30

Gly Pro Cys Arg Ser Gly Gly Gly Ser Ser Gly Gly Gly Gly Gly Gly
         35                  40                  45

Gly Gly Gly Ser Gly Gly Ala Asn Val Ala Asn Val Val Thr Asp Ala
     50                  55                  60

Phe Phe Asn Gly Ile Lys Asn Gln Ala Gly Ser Trp Cys Glu Gly Lys
 65                  70                  75                  80

Asn Phe Tyr Thr Arg Ser Ala Phe Leu Ser Ala Val Lys Ala Tyr Pro
                 85                  90                  95

Gly Phe Ala His Gly Gly Ser Gln Val Gln Gly Lys Arg Glu Ile Ala
            100                 105                 110

Ala Phe Phe Ala His Val Thr His Glu Thr Gly His Leu Cys Tyr Ile
        115                 120                 125

Asn Glu Val Asn Lys Ser Asn Ala Tyr Cys Asp Pro Thr Lys Arg Gln
    130                 135                 140

Trp Pro Cys Ala Ala Gly Gln Lys Tyr Tyr Gly Arg Gly Pro Leu Gln
145                 150                 155                 160

Ile Ser Trp Asn Tyr Asn Tyr Gly Pro Ala Gly Arg Ala Ile Gly Phe
                165                 170                 175

Asp Gly Leu Gly Asp Pro Asp Arg Leu Ala Gln Asp Pro Val Leu Ser
            180                 185                 190

Phe Lys Ser Ala Leu Trp Phe Trp Met Asn Asn Val His Arg Val Met
        195                 200                 205

Pro Gln Gly Phe Gly Ala Thr Ile Arg Ala Ile Asn Gly Ala Leu Glu
    210                 215                 220

Cys Gly Gly Asn Asn Pro Ala Gln Met Asn Ala Arg Val Gly Tyr Tyr
225                 230                 235                 240

Arg Gln Tyr Cys Arg Gln Leu Gly Val Asp Pro Gly Asn Asn Leu Thr
                245                 250                 255

Cys
```

<210> SEQ ID NO 25
<211> LENGTH: 762
<212> TYPE: DNA
<213> ORGANISM: Unknown
<220> FEATURE:
<223> OTHER INFORMATION: Variant sequence produced by shuffling
      techniques 4M1/26_C2 nucleic acid

<400> SEQUENCE: 25

```
tcgatgcaga actgcgggtg cgcgtcgggc ctgtgctgca gccggttcgg gtactgcggg    60
acgggcgagg actactgcgg cgccgggtgc cagtcgggcc cgtgccgctc gggcggcggc   120
ggcggcggcg gaggcggcgg aggcagtggc ggtgcgaacg tggctaatgt ggtcaccgac   180
```

```
gcgttcttca acggcatcaa gaaccaggcc gggagcgggt gcgagggcaa gaacttctac    240
acccggagcg cgttcctgag cgccgtcaag gcgtacccag gcttcgcgca tggcggctcc    300
gaggtcgagc gcaagcgcga gattgccgcc ttcttcgcgc atgtcacgca cgagaccggg    360
catttctgct acatcagcga gatcaacaag agcaacgcct actgcgaccc gaccaagagg    420
cagtggccgt gcgccgcggg gcagaagtac tacggccgcg gcccgctgca gatctcctgg    480
aactacaact acgggcccgc ggggagggcc atcggcttcg acgggctggg agacccggac    540
agactggcgc aggaccccgt gttgtcgttc aaggcggcgc tctggttctg gatgaacaac    600
gtgcaccgtg tgatgccgca gggcttcggc gccaccatca gggccatcaa cggcgccctc    660
gagtgcaacg gaacaacccc cgcccagatg aacgcgcgcg tcggctacta caggcagtac    720
tgccgccagc tcggcgtcga cccgggcaac aacctcacct gc                      762
```

<210> SEQ ID NO 26
<211> LENGTH: 254
<212> TYPE: PRT
<213> ORGANISM: Unknown
<220> FEATURE:
<223> OTHER INFORMATION: Variant sequence produced by shuffling
      techniques 4M1/26_C2

<400> SEQUENCE: 26

```
Ser Met Gln Asn Cys Gly Cys Ala Ser Gly Leu Cys Cys Ser Arg Phe
  1               5                  10                  15

Gly Tyr Cys Gly Thr Gly Glu Asp Tyr Cys Gly Ala Gly Cys Gln Ser
             20                  25                  30

Gly Pro Cys Arg Ser Gly Gly Gly Gly Gly Gly Gly Gly Gly Gly Gly
         35                  40                  45

Ser Gly Gly Ala Asn Val Ala Asn Val Val Thr Asp Ala Phe Phe Asn
     50                  55                  60

Gly Ile Lys Asn Gln Ala Gly Ser Gly Cys Glu Gly Lys Asn Phe Tyr
 65                  70                  75                  80

Thr Arg Ser Ala Phe Leu Ser Ala Val Lys Ala Tyr Pro Gly Phe Ala
                 85                  90                  95

His Gly Gly Ser Glu Val Glu Arg Lys Arg Glu Ile Ala Ala Phe Phe
            100                 105                 110

Ala His Val Thr His Glu Thr Gly His Phe Cys Tyr Ile Ser Glu Ile
        115                 120                 125

Asn Lys Ser Asn Ala Tyr Cys Asp Pro Thr Lys Arg Gln Trp Pro Cys
130                 135                 140

Ala Ala Gly Gln Lys Tyr Tyr Gly Arg Gly Pro Leu Gln Ile Ser Trp
145                 150                 155                 160

Asn Tyr Asn Tyr Gly Pro Ala Gly Arg Ala Ile Gly Phe Asp Gly Leu
                165                 170                 175

Gly Asp Pro Asp Arg Leu Ala Gln Asp Pro Val Leu Ser Phe Lys Ala
            180                 185                 190

Ala Leu Trp Phe Trp Met Asn Asn Val His Arg Val Met Pro Gln Gly
        195                 200                 205

Phe Gly Ala Thr Ile Arg Ala Ile Asn Gly Ala Leu Glu Cys Asn Gly
    210                 215                 220

Asn Asn Pro Ala Gln Met Asn Ala Arg Val Gly Tyr Tyr Arg Gln Tyr
225                 230                 235                 240

Cys Arg Gln Leu Gly Val Asp Pro Gly Asn Asn Leu Thr Cys
                245                 250
```

<210> SEQ ID NO 27
<211> LENGTH: 750
<212> TYPE: DNA
<213> ORGANISM: Unknown
<220> FEATURE:
<223> OTHER INFORMATION: Variant sequence produced by shuffling
techniques r1AB2 nucleic acid

<400> SEQUENCE: 27

```
tcgatgcaga actgcggctg ccagccaaac ttctgctgca gcaagttcgg ctactgcggc      60
acgaccgacg cctactgcgg cgacgggtgc cagtcgggcc cgtgccgctc gggcggcggc     120
ggcagcagtg gcggcggtgg tgcgaacgtg gctagcgtcg tcaccggctc cttcttcaac     180
ggcatcaaga gccaggccgg gagcgggtgc gagggcaaga acttctacac ccggagcgcg     240
ttcctgagcg ccgtcaaggc gtacccaggc ttcgcccatg gcggctccga ggtcgagcgc     300
aagcgcgaga ttgccgcctt cttcgcgcat gtcacgcacg agaccgggca tttctgctac     360
atcagcgaga tcaacaagag caacgcctac tgcgacccga ccaagaggca gtggccgtgc     420
gccgcggggc agaagtacta cgggcgcggc ccgctgcaga tctcgtggaa ctacaactac     480
gggcccgcgg ggagggccat cggcttcgac gggctcgggg accccggcag ggtggcgcgg     540
gacgccgtgg tggcgttcaa ggcggcgctc tggttctgga tgaacaacgt gcaccgtgtg     600
atgccgcagg gcttcggcgc caccatcagg gccatcaacg cgccctcga gtcgacggc     660
aagaacccca actccgtcaa caaccgcgtc gcctactaca agcagttctg ccaggatttc     720
ggcgtcgacc cagggcccaa ccttacttgc                                     750
```

<210> SEQ ID NO 28
<211> LENGTH: 250
<212> TYPE: PRT
<213> ORGANISM: Unknown
<220> FEATURE:
<223> OTHER INFORMATION: Variant sequence produced by shuffling
techniques r1AB2

<400> SEQUENCE: 28

```
Ser Met Gln Asn Cys Gly Cys Gln Pro Asn Phe Cys Cys Ser Lys Phe
  1               5                  10                  15

Gly Tyr Cys Gly Thr Thr Asp Ala Tyr Cys Gly Asp Gly Cys Gln Ser
             20                  25                  30

Gly Pro Cys Arg Ser Gly Gly Gly Ser Ser Gly

```
Gly Pro Ala Gly Arg Ala Ile Gly Phe Asp Gly Leu Gly Asp Pro Gly
                165                 170                 175

Arg Val Ala Arg Asp Ala Val Val Ala Phe Lys Ala Ala Leu Trp Phe
            180                 185                 190

Trp Met Asn Asn Val His Arg Val Met Pro Gln Gly Phe Gly Ala Thr
        195                 200                 205

Ile Arg Ala Ile Asn Gly Ala Leu Glu Cys Asp Gly Lys Asn Pro Asn
    210                 215                 220

Ser Val Asn Asn Arg Val Ala Tyr Tyr Lys Gln Phe Cys Gln Asp Phe
225                 230                 235                 240

Gly Val Asp Pro Gly Pro Asn Leu Thr Cys
                245                 250

<210> SEQ ID NO 29
<211> LENGTH: 771
<212> TYPE: DNA
<213> ORGANISM: Unknown
<220> FEATURE:
<223> OTHER INFORMATION: Variant sequence produced by shuffling
      techniques r1 AD4 nucleic acid

<400> SEQUENCE: 29
tcgatgcaga actgcggctg ccagccaaac gtatgctgca gcaagtttgg ctactgcggc      60
acgaccgacg agtactgcgg cgacgggtgc cagtcgggcc cgtgccgctc gggcggcggt     120
ggcggcggcg gcggcggcgg aggcggcgga ggcagtggcg gtgcgaacgt ggctaatgtg     180
gtcaccgacg cgttcttcaa cggcatcaag aaccaggccg ggagcgggtg cgagggcaag     240
aacttctaca cccggagcgc gttcctcgag gccatcgccg cgtacccggg cttcgcgcat     300
ggcggctccg aggtcgagcg caagcgcgag attgccgcct tcttcgcgca cgccacgcac     360
gagaccgggc atttctgcta catcagcgag gtcaacaaga gcaacgccta ctgcgacccg     420
accaagaggc agtggccgtg cgccgcgggg cagaagtact acgggcgcgg cccgctgcag     480
atctcgtgga actacaacta cgggcccgcg gggagggcca tcggcttcga cgggctcggg     540
gacccggca gggtggcgcg ggacgccgtg gtggcgttca aggcggcgct ctggttctgg     600
atgaacaacg tgcaccgtgt gatgccgcag ggcttcggcg ccaccatcag ggccatcaac     660
ggcgccctcg agtgcggcgg gaacaacccc gcccagatga acgcgcgcgt cggctactac     720
aagcagtact gccgccagct cggcgtcgac ccagggccca acctcacttg c               771

<210> SEQ ID NO 30
<211> LENGTH: 257
<212> TYPE: PRT
<213> ORGANISM: Unknown
<220> FEATURE:
<223> OTHER INFORMATION: Variant sequence produced by shuffling
      techniques r1 AD4

<400> SEQUENCE: 30

Ser Met Gln Asn Cys Gly Cys Gln Pro Asn Val Cys Cys Ser Lys Phe
1                5                  10                  15

Gly Tyr Cys Gly Thr Thr Asp Glu Tyr Cys Gly Asp Gly Cys Gln Ser
            20                  25                  30

Gly Pro Cys Arg Ser Gly Gly

```
                65                  70                  75                  80
Asn Phe Tyr Thr Arg Ser Ala Phe Leu Glu Ala Ile Ala Ala Tyr Pro
                    85                  90                  95
Gly Phe Ala His Gly Gly Ser Glu Val Glu Arg Lys Arg Glu Ile Ala
                100                 105                 110
Ala Phe Ala His Ala Thr His Glu Thr Gly His Phe Cys Tyr Ile
        115                 120                 125
Ser Glu Val Asn Lys Ser Asn Ala Tyr Cys Asp Pro Thr Lys Arg Gln
    130                 135                 140
Trp Pro Cys Ala Ala Gly Gln Lys Tyr Tyr Gly Arg Gly Pro Leu Gln
145                 150                 155                 160
Ile Ser Trp Asn Tyr Asn Tyr Gly Pro Ala Gly Arg Ala Ile Gly Phe
                165                 170                 175
Asp Gly Leu Gly Asp Pro Gly Arg Val Ala Arg Asp Ala Val Val Ala
            180                 185                 190
Phe Lys Ala Ala Leu Trp Phe Trp Met Asn Asn Val His Arg Val Met
    195                 200                 205
Pro Gln Gly Phe Gly Ala Thr Ile Arg Ala Ile Asn Gly Ala Leu Glu
210                 215                 220
Cys Gly Gly Asn Asn Pro Ala Gln Met Asn Ala Arg Val Gly Tyr Tyr
225                 230                 235                 240
Lys Gln Tyr Cys Arg Gln Leu Gly Val Asp Pro Gly Pro Asn Leu Thr
                245                 250                 255
Cys
```

<210> SEQ ID NO 31
<211> LENGTH: 750
<212> TYPE: DNA
<213> ORGANISM: Unknown
<220> FEATURE:
<223> OTHER INFORMATION: Variant sequence produced by shuffling
      techniques r1 AD6 nucleic acid

<400> SEQUENCE: 31

```
tcgatgcaga actgcggctg ccagccaaac ttctgctgca gcaagtttgg ctactgcggc      60
acgaccgacg agtactgcgg cgccgggtgc cagtcgggcc cgtgccgctc gggcggcggc     120
ggcagcagtg gcggcggtgg tgcgaacgtg gctagcgtcg tcaccggctc cttcttcaac     180
ggcatcaaga accaggccgg gagcgggtgc gagggcaaga acttctacac ccggagcgcg     240
ttcctgagcg ccgtcaaggc gtacccaggc ttcgcccatg gcggctccga ggtcgagcgc     300
aagcgcgaga tcgccgcctt cttcgcgcac gccacgcatg agaccgggca tttctgctac     360
atcagcgaga tcaacaagag caacgcctac tgcgacccga ccaagaggca gtggccgtgc     420
gccgcgggc agaagtacta cgggcgcggc ccgctgcaga tctcgtggaa ctacaactac     480
gggcccgcgg gagggccat cggctttgac gggctcgggg accccggcag ggtggcgcag     540
gaccccgtgc tggcgttcaa ggcggcgctc tggttctgga tgaacagcgt gcacggggtg     600
gtgccgcagg gcttcggcgc caccatcagg gccatcaacg cgccctcga gtgcaacggg     660
aacaaccccg cccagatgaa cgcgcgcgtc ggctactaca gcagttctg ccaggatttc     720
ggcgtcgacc cagggcccaa cctcacttgc                                      750
```

<210> SEQ ID NO 32
<211> LENGTH: 250
<212> TYPE: PRT
<213> ORGANISM: Unknown

```
<220> FEATURE:
<223> OTHER INFORMATION: Variant sequence produced by shuffling
      techniques r1 AD6

<400> SEQUENCE: 32
```

| Ser | Met | Gln | Asn | Cys | Gly | Cys | Gln | Pro | Asn | Phe | Cys | Cys | Ser | Lys | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gly Tyr Cys Gly Thr Thr Asp Glu Tyr Cys Gly Ala Gly Cys Gln Ser
                20                  25                  30

Gly Pro Cys Arg Ser Gly Gly Gly Ser Ser Gly Gly Gly Gly Ala
            35              40                  45

Asn Val Ala Ser Val Val Thr Gly Ser Phe Phe Asn Gly Ile Lys Asn
    50                  55                  60

Gln Ala Gly Ser Gly Cys Glu Gly Lys Asn Phe Tyr Thr Arg Ser Ala
65              70                  75                  80

Phe Leu Ser Ala Val Lys Ala Tyr Pro Gly Phe Ala His Gly Ser
                85                  90                  95

Glu Val Glu Arg Lys Arg Glu Ile Ala Ala Phe Phe Ala His Ala Thr
                100                 105                 110

His Glu Thr Gly His Phe Cys Tyr Ile Ser Glu Ile Asn Lys Ser Asn
                115                 120                 125

Ala Tyr Cys Asp Pro Thr Lys Arg Gln Trp Pro Cys Ala Ala Gly Gln
130                 135                 140

Lys Tyr Tyr Gly Arg Gly Pro Leu Gln Ile Ser Trp Asn Tyr Asn Tyr
145                 150                 155                 160

Gly Pro Ala Gly Arg Ala Ile Gly Phe Asp Gly Leu Gly Asp Pro Gly
                165                 170                 175

Arg Val Ala Gln Asp Pro Val Leu Ala Phe Lys Ala Ala Leu Trp Phe
                180                 185                 190

Trp Met Asn Ser Val His Gly Val Val Pro Gln Gly Phe Gly Ala Thr
                195                 200                 205

Ile Arg Ala Ile Asn Gly Ala Leu Glu Cys Asn Gly Asn Asn Pro Ala
                210                 215                 220

Gln Met Asn Ala Arg Val Gly Tyr Tyr Lys Gln Phe Cys Gln Asp Phe
225                 230                 235                 240

Gly Val Asp Pro Gly Pro Asn Leu Thr Cys
                245                 250

```
<210> SEQ ID NO 33
<211> LENGTH: 771
<212> TYPE: DNA
<213> ORGANISM: Unknown
<220> FEATURE:
<223> OTHER INFORMATION: Variant sequence produced by shuffling
      techniques r1 AG9 nucleic acid <400> SEQUENCE: 33
tcgatgcaga actgcggctg ccagccaaac gtatgctgca gcaagtttgg ctactgcggc      60
acaaccgacg agtactgcgg cgacgggtgc cagtcgggcc cgtgccgctc gggcggcggt     120
ggcggcggcg gcggcggcgg aggcggcgga ggcagtggcg gtgcgaacgt ggctaatgtg     180
gtcaccgacg cgttcttcaa cggcatcaag aaccaggccg ggagcgggtg cgagggcaag     240
aacttctaca cccggagcgc gttcctcgag gccatcgccg cgtacccggg cttcgcgcat     300
ggcggctccg aggtcgagcg caagcgcgag attgccgcct tcttcgcgca cgccacgcac     360
gagaccgggc atttctgcta catcagcgag gtcaacaaga gcaacgccta ctgcgacccg     420
```

-continued

```
accaagaggc agtggccgtg cgccgcgggg cagaagtact acgggcgcgg cccgctgcag    480
atctcgtgga actacaacta cgggcccgcg gggagggcca tcggcttcga cgggctcggg    540
gaccccggca gggtggcgcg ggacgccgtg gtggcgttca aggcggcgct ctggttctgg    600
atgaacaacg tgcaccgtgt gatgccgcag ggcttcggcg ccaccatcag ggccatcaac    660
ggcgccctcg agtgcggcgg gaacaacccc gcccagatga acgcgcgcgt cggctactac    720
aagcagtact gccgccagct cggcgtcgac ccagggccca acctcacttg c             771
```

<210> SEQ ID NO 34
<211> LENGTH: 257
<212> TYPE: PRT
<213> ORGANISM: Unknown
<220> FEATURE:
<223> OTHER INFORMATION: Variant sequence produced by shuffling techniques r1 AG9

<400> SEQUENCE: 34

```
Ser Met Gln Asn Cys Gly Cys Gln Pro Asn Val Cys Cys Ser Lys Phe
  1               5                  10                  15

Gly Tyr Cys Gly Thr Thr Asp Glu Tyr Cys Gly Asp Gly Cys Gln Ser
             20                  25                  30

Gly Pro Cys Arg Ser Gly Gly Gly Gly Gly Gly Gly Gly Gly Gly
         35                  40                  45

Gly Gly Gly Ser Gly Gly Ala Asn Val Ala Asn Val Thr Asp Ala
     50                  55                  60

Phe Phe Asn Gly Ile Lys Asn Gln Ala Gly Ser Gly Cys Glu Gly Lys
 65                  70                  75                  80

Asn Phe Tyr Thr Arg Ser Ala Phe Leu Glu Ala Ile Ala Ala Tyr Pro
                 85                  90                  95

Gly Phe Ala His Gly Ser Glu Val Glu Arg Lys Arg Glu Ile Ala
            100                 105                 110

Ala Phe Ala His Ala Thr His Glu Thr Gly His Phe Cys Tyr Ile
        115                 120                 125

Ser Glu Val Asn Lys Ser Asn Ala Tyr Cys Asp Pro Thr Lys Arg Gln
130                 135                 140

Trp Pro Cys Ala Ala Gly Gln Lys Tyr Tyr Gly Arg Gly Pro Leu Gln
145                 150                 155                 160

Ile Ser Trp Asn Tyr Asn Tyr Gly Pro Ala Gly Arg Ala Ile Gly Phe
                165                 170                 175

Asp Gly Leu Gly Asp Pro Gly Arg Val Ala Arg Asp Ala Val Val Ala
            180                 185                 190

Phe Lys Ala Ala Leu Trp Phe Trp Met Asn Asn Val His Arg Val Met
        195                 200                 205

Pro Gln Gly Phe Gly Ala Thr Ile Arg Ala Ile Asn Gly Ala Leu Glu
    210                 215                 220

Cys Gly Gly Asn Asn Pro Ala Gln Met Asn Ala Arg Val Gly Tyr Tyr
225                 230                 235                 240

Lys Gln Tyr Cys Arg Gln Leu Gly Val Asp Pro Gly Pro Asn Leu Thr
                245                 250                 255

Cys
```

<210> SEQ ID NO 35
<211> LENGTH: 750
<212> TYPE: DNA
<213> ORGANISM: Unknown
<220> FEATURE:

```
<223> OTHER INFORMATION: Variant sequence produced by shuffling
      techniques r1 AH8 nucleic acid

<400> SEQUENCE: 35 tcgatg

```
                195                 200                 205
Ile Arg Ala Ile Asn Gly Ala Leu Glu Cys Asn Gly Asn Pro Ala
    210                 215                 220

Gln Met Asn Ala Arg Val Gly Tyr Tyr Lys Gln Tyr Cys Gln Leu
225                 230                 235                 240

Arg Val Asp Pro Gly Pro Asn Leu Thr Cys
                245                 250

<210> SEQ ID NO 37
<211> LENGTH: 771
<212> TYPE: DNA
<213> ORGANISM: Unknown
<220> FEATURE:
<223> OTHER INFORMATION: Variant sequence produced by shuffling
      techniques r1 AH9 nucleic acid

<400> SEQUENCE: 37
tcgatgcaga actgcggctg ccagccaaac gtatgctgca gcaagtttgg ctactgcggc      60
acgaccgacg agtactgcgg cgacgggtgc cagtcgggcc cgtgccgccc gggcggcggc     120
ggcggcggcg gcggcggcgg aggcggcgga ggcagtggcg gtgcgaacgt ggctaatgtg     180
gtcaccgacg cgttcttcaa cggcatcaag aaccaggccg ggagcgggtg cgagggcaag     240
aacttctaca cccggagagc gttcctgagc gccgtcaagg cgtacccagg cttcgcccat     300
ggcgggtcgc aggtgcaggg caagcgcgag atcgccgcct tcttcgcgca cgccacgcac     360
gagaccggga tttctgctca catcagcgag atcaacaaga gcaacgccta ctgcgacccg     420
accaagaggc agtggccgtg cgccgcgggg cagaagtact acgggcgcgg cccgctgcag     480
atctcgtgga actacaacta cgggcccgcc gggagggaca tcggcttcaa cgggctcgcc     540
gaccccaaca gggtggcgca ggacgccgtg gtggcgttca aggcggcgct ctggttctgg     600
atgaacagcg tgcacggggt ggtgccgcag gggttcggcg ccaccaccag gccatcaac      660 ggcgccctcg agtgcaacgg gaacaacccc gcccagatga acgcgcgcgt cggctactac     720
aggcagtact gccgccagct cggcgtcgac ccagggccca acctcacttg c              771

<210> SEQ ID NO 38
<211> LENGTH: 257
<212> TYPE: PRT
<213> ORGANISM: Unknown
<220> FEATURE:
<223> OTHER INFORMATION: Variant sequence produced by shuffling
      techniques r1 AH9

<400> SEQUENCE: 38

Ser Met Gln Asn Cys Gly Cys Gln Pro Asn Val Cys Cys Ser Lys Phe
1               5                   10                  15

Gly Tyr Cys Gly Thr Thr Asp Glu Tyr Cys Gly Asp Gly Cys Gln Ser
                20                  25                  30

Gly Pro Cys Arg Pro Gly Gly Gly Gly Gly Gly Gly Gly Gly Gly Gly
            35                  40                  45

Gly Gly Gly Ser Gly Gly Ala Asn Val Ala Asn Val Thr Asp Ala
        50                  55                  60

Phe Phe Asn Gly Ile Lys Asn Gln Ala Gly Ser Gly Cys Glu Gly Lys
65                  70                  75                  80

Asn Phe Tyr Thr Arg Arg Ala Phe Leu Ser Ala Val Lys Ala Tyr Pro
                85                  90                  95

Gly Phe Ala His Gly Gly Ser Gln Val Gln Gly Lys Arg Glu Ile Ala
            100                 105                 110
```

Ala Phe Phe Ala His Ala Thr His Glu Thr Gly His Phe Cys Tyr Ile
            115                 120                 125

Ser Glu Ile Asn Lys Ser Asn Ala Tyr Cys Asp Pro Thr Lys Arg Gln
        130                 135                 140

Trp Pro Cys Ala Ala Gly Gln Lys Tyr Tyr Gly Arg Gly Pro Leu Gln
145                 150                 155                 160

Ile Ser Trp Asn Tyr Asn Tyr Gly Pro Ala Gly Arg Asp Ile Gly Phe
                165                 170                 175

Asn Gly Leu Ala Asp Pro Asn Arg Val Ala Gln Asp Ala Val Val Ala
            180                 185                 190

Phe Lys Ala Ala Leu Trp Phe Trp Met Asn Ser Val His Gly Val Val
        195                 200                 205

Pro Gln Gly Phe Gly Ala Thr Thr Arg Ala Ile Asn Gly Ala Leu Glu
    210                 215                 220

Cys Asn Gly Asn Asn Pro Ala Gln Met Asn Ala Arg Val Gly Tyr Tyr
225                 230                 235                 240

Arg Gln Tyr Cys Arg Gln Leu Gly Val Asp Pro Gly Pro Asn Leu Thr
                245                 250                 255

Cys

<210> SEQ ID NO 39
<211> LENGTH: 777
<212> TYPE: DNA
<213> ORGANISM: Unknown
<220> FEATURE:
<223> OTHER INFORMATION: Variant sequence produced by shuffling
      techniques r1 BG5 nucleic acid

<400> SEQUENCE: 39
tcgatgcaga actgcggctg ccagccaaac gtatgctgca gcaagttcgg ctactgcggc      60
acgaccgacg agtactgcgg cgacgggtgc cagtcgggcc cgtgccactc gggcggcggc     120
ggcagctgtg gcggcggtgg cggcggcagc ggcggaggca gtggcggtgc gaacgtggct     180
aatgtggtca ccggctcctt cttcaacggc atcaagaacc aggccgggag cgggtgcgag     240
ggcaagaact tctacacccg gagcgcgttc ctgagcgccg tcaaggcgta cccaggcttc     300
gcccatggcg ggtcacaggt gcagggcaag cgcgagatcg ccgccttctt cgcgcatgtc     360
acgcacgaga ccgggcattt ctgctacatc agcgagatca acaagagcaa cgcctactgc     420
gacccgacca gaggcagtg gccgtgcgcc gcggggcaga agtactacgg cgcggcccg      480
ctgcagatct cgtggaacta caactacggg cccgcgggga gggccatcgg cttcgacggg     540
ctcggggacc ccggcagggt ggcgcaggac gccgtgatcg cgttcaagtc ggcgctctgg     600
tactggatgg agaacatgca ccagctcatg ccccagggct tcggcgccac catcagggcc     660
atcaacggcg ccctcgagtg cggcgggaac aaccccgccc agatgaacgc gcgcgtcggc     720
tactacaagc agtactgcca ccagctcggc gtcgacccag ggcccaacct cacttgc       777

<210> SEQ ID NO 40
<211> LENGTH: 259
<212> TYPE: PRT
<213> ORGANISM: Unknown
<220> FEATURE:
<223> OTHER INFORMATION: Variant sequence produced by shuffling
      techniques r1 BG5

<400> SEQUENCE: 40

Ser Met Gln Asn Cys Gly Cys Gln Pro Asn Val Cys Cys Ser Lys Phe

```
                1               5              10              15
Gly Tyr Cys Gly Thr Thr Asp Glu Tyr Cys Asp Gly Cys Gln Ser
                    20                  25                  30

Gly Pro Cys His Ser Gly Gly Gly Ser Cys Gly Gly Gly Gly
                35                  40                  45

Gly Ser Gly Gly Gly Ser Gly Gly Ala Asn Val Ala Asn Val Val Thr
50                  55                  60

Gly Ser Phe Phe Asn Gly Ile Lys Asn Gln Ala Gly Ser Gly Cys Glu
65                  70                  75                  80

Gly Lys Asn Phe Tyr Thr Arg Ser Ala Phe Leu Ser Ala Val Lys Ala
                85                  90                  95

Tyr Pro Gly Phe Ala His Gly Gly Ser Gln Val Gln Gly Lys Arg Glu
                    100                 105                 110

Ile Ala Ala Phe Phe Ala His Val Thr His Glu Thr Gly His Phe Cys
                    115                 120                 125

Tyr Ile Ser Glu Ile Asn Lys Ser Asn Ala Tyr Cys Asp Pro Thr Lys
                130                 135                 140

Arg Gln Trp Pro Cys Ala Ala Gly Gln Lys Tyr Tyr Gly Arg Gly Pro
145                 150                 155                 160

Leu Gln Ile Ser Trp Asn Tyr Asn Tyr Gly Pro Ala Gly Arg Ala Ile
                    165                 170                 175

Gly Phe Asp Gly Leu Gly Asp Pro Gly Arg Val Ala Gln Asp Ala Val
                    180                 185                 190

Ile Ala Phe Lys Ser Ala Leu Trp Tyr Trp Met Glu Asn Met His Gln
                195                 200                 205

Leu Met Pro Gln Gly Phe Gly Ala Thr Ile Arg Ala Ile Asn Gly Ala
210                 215                 220

Leu Glu Cys Gly Gly Asn Asn Pro Ala Gln Met Asn Ala Arg Val Gly
225                 230                 235                 240

Tyr Tyr Lys Gln Tyr Cys His Gln Leu Gly Val Asp Pro Gly Pro Asn
                    245                 250                 255

Leu Thr Cys

<210> SEQ ID NO 41
<211> LENGTH: 768
<212> TYPE: DNA
<213> ORGANISM: Unknown
<220> FEATURE:
<223> OTHER INFORMATION: Variant sequence produced by shuffling
      techniques r2C5 nucleic acid

<400> SEQUENCE: 41
tcgatgcaga actgcgggtg cgcgtcgggc atgtgctgca gccggttcgg ctactgcggc      60
acgaccgacg agtactgcgg cgacgggtgc cagtcgggcc cgtgccgctc gggcggcggc     120
ggcggcggcg gcggcggagg cggcggaggc agtggcggtg cgaacgtggc tagcgtcgtc     180
accggctcct tcttcagcgg catcaagaac caggccggga gcgggtgcga gggcaagaac     240
ttctacaccc ggagcgcgtt cctgagcgcc gtcaaggcgt acccaggctt cgcccatggc     300
gggacggagg tggagggcaa gcgcgagatc gccgccttcc tcgcgcacat cacgcacgag     360
accgggcatt tctgctacat cagcgagatc aacaagagca cgcctactg cgacccgacc      420 aagaggcagt ggccgtgcgc cgcggggcag aagtactacg gcgcggcccc gctgcagatc     480
tcgtggaact acaactacgg gcccgcgggg agggccatcg gctcgacgg gctcggggac      540 cccggcaggg tggcgcggga cgccgtggtg gcgttcaagg cggcgctctg gttctggatg     600
```

```
aacagcgtgc acggggtgat gccccagggg ttcggcgcca ccatcagggc catcaacggc    660
gcgctcgagt gcgacgggaa caccccgcc cagatgaacg cgcgcgtcgg ctactacaag    720
cagtactgcc agcagctccg cgtcgacccg ggcaacaacc tcacttgc                768
```

```
<210> SEQ ID NO 42
<211> LENGTH: 256
<212> TYPE: PRT
<213> ORGANISM: Unknown
<220> FEATURE:
<223> OTHER INFORMATION: Variant sequence produced by shuffling
      techniques r2C5

<400> SEQUENCE: 42
```

| Ser | Met | Gln | Asn | Cys | Gly | Cys | Ala | Ser | Gly | Met | Cys | Cys | Ser | Arg | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Tyr | Cys | Gly | Thr | Thr | Asp | Glu | Tyr | Cys | Gly | Asp | Gly | Cys | Gln | Ser |
|     |     |     |     | 20  |     |     |     |     | 25  |     |     |     |     | 30  |     |

| Gly | Pro | Cys | Arg | Ser | Gly | Gly | Gly | Gly | Gly | Gly | Gly | Gly | Gly |
|     |     |     |     | 35  |     |     |     |     | 40  |     |     |     |     | 45  |

| Gly | Gly | Ser | Gly | Gly | Ala | Asn | Val | Ala | Ser | Val | Val | Thr | Gly | Ser | Phe |
|     |     |     |     | 50  |     |     |     |     | 55  |     |     |     |     | 60  |     |

| Phe | Ser | Gly | Ile | Lys | Asn | Gln | Ala | Gly | Ser | Gly | Cys | Glu | Gly | Lys | Asn |
| 65  |     |     |     |     | 70  |     |     |     |     | 75  |     |     |     |     | 80  |

| Phe | Tyr | Thr | Arg | Ser | Ala | Phe | Leu | Ser | Ala | Val | Lys | Ala | Tyr | Pro | Gly |
|     |     |     |     | 85  |     |     |     |     | 90  |     |     |     |     | 95  |     |

| Phe | Ala | His | Gly | Gly | Thr | Glu | Val | Glu | Gly | Lys | Arg | Glu | Ile | Ala | Ala |
|     |     |     |     | 100 |     |     |     |     | 105 |     |     |     |     | 110 |     |

| Phe | Leu | Ala | His | Ile | Thr | His | Glu | Thr | Gly | His | Phe | Cys | Tyr | Ile | Ser |
|     |     |     |     | 115 |     |     |     |     | 120 |     |     |     |     | 125 |     |

| Glu | Ile | Asn | Lys | Ser | Asn | Ala | Tyr | Cys | Asp | Pro | Thr | Lys | Arg | Gln | Trp |
|     | 130 |     |     |     |     | 135 |     |     |     |     | 140 |     |     |     |     |

| Pro | Cys | Ala | Ala | Gly | Gln | Lys | Tyr | Tyr | Gly | Arg | Gly | Pro | Leu | Gln | Ile |
| 145 |     |     |     |     | 150 |     |     |     |     | 155 |     |     |     |     | 160 |

| Ser | Trp | Asn | Tyr | Asn | Tyr | Gly | Pro | Ala | Gly | Arg | Ala | Ile | Gly | Leu | Asp |
|     |     |     |     |     | 165 |     |     |     |     | 170 |     |     |     |     | 175 |

| Gly | Leu | Gly | Asp | Pro | Gly | Arg | Val | Ala | Arg | Asp | Ala | Val | Ala | Phe |
|     |     |     |     | 180 |     |     |     |     | 185 |     |     |     |     | 190 |

| Lys | Ala | Ala | Leu | Trp | Phe | Trp | Met | Asn | Ser | Val | His | Gly | Val | Met | Pro |
|     |     |     | 195 |     |     |     |     | 200 |     |     |     |     | 205 |     |     |

| Gln | Gly | Phe | Gly | Ala | Thr | Ile | Arg | Ala | Ile | Asn | Gly | Ala | Leu | Glu | Cys |
|     | 210 |     |     |     |     | 215 |     |     |     |     | 220 |     |     |     |     |

| Asp | Gly | Asn | Asn | Pro | Ala | Gln | Met | Asn | Ala | Arg | Val | Gly | Tyr | Tyr | Lys |
| 225 |     |     |     |     | 230 |     |     |     |     | 235 |     |     |     |     | 240 |

| Gln | Tyr | Cys | Gln | Gln | Leu | Arg | Val | Asp | Pro | Gly | Asn | Asn | Leu | Thr | Cys |
|     |     |     |     | 245 |     |     |     |     | 250 |     |     |     |     | 255 |     |

```
<210> SEQ ID NO 43
<211> LENGTH: 750
<212> TYPE: DNA
<213> ORGANISM: Unknown
<220> FEATURE:
<223> OTHER INFORMATION: Variant sequence produced by shuffling
      techniques 4N1/95_H3 nucleic acid

<400> SEQUENCE: 43
```

```
tcgatgcaga actgcggctg ccagccaaac gtatgctgca gcaagtttgg ctactgcggc    60
```

-continued

```
acgaccgacg agtactgcgg cgacgggtgc cagtcgggcc cgtgccgctc gggcggcggc    120
ggcagcagtg gcggcggtgg tgcgaacgtg gctaatgtgg tcaccgacgc gttcttcaac    180
ggcatcaaga accaggccgg gagcgggtgc gagggcaaga acttctacac ccggagcgcg    240
ttcctgagcg ccgtcaaggc gtacccaggc ttcgcccatg gcggctccga ggtcgagcgc    300
aagcgcgaga ttgccgcctt cttcgcgcat gtcacgcacg agaccgggca tttctgctac    360
atcagcgaga tcaacaagag caacgcctac tgcgacccga ccaagaggca gtggccgtgc    420
gccgcggggc agaagtacta cgggcgcggc ccgctgcaga tctcgtggaa ctacaactac    480
gggcccgcgg ggagggccat cggcttcgac gggctcgggg accccggcag ggtggcgcgg    540
gacgccgtgg tggcgttcaa ggcggcgctc tggttctgga tgaacaacgt gcaccgtgtg    600
atgccgcagg gcttcggcgc caccatcagg gccatcaacg gcgccctcga gtgcggcggg    660
aacaaccccg cccagatgaa cgcgcgcgtc ggctactaca agcagtactg ccgccagctc    720
ggcgtcgacc cagggcccaa cctcacttgc                                     750

<210> SEQ ID NO 44
<211> LENGTH: 250
<212> TYPE: PRT
<213> ORGANISM: Unknown
<220> FEATURE:
<223> OTHER INFORMATION: Variant sequence produced by shuffling
      techniques 4N1/95_H3

<400> SEQUENCE: 44

Ser Met Gln Asn Cys Gly Cys Gln Pro Asn Val Cys Cys Ser Lys Phe
 1               5                  10                  15

Gly Tyr Cys Gly Thr Thr Asp Glu Tyr Cys Gly Asp Gly Cys Gln Ser
            20                  25                  30

Gly Pro Cys Arg Ser Gly Gly Gly Gly Ser Ser Gly Gly Gly Gly Ala
        35                  40                  45

Asn Val Ala Asn Val Val Thr Asp Ala Phe Phe Asn Gly Ile Lys Asn
    50                  55                  60

Gln Ala Gly Ser Gly Cys Glu Gly Lys Asn Phe Tyr Thr Arg Ser Ala
65                  70                  75                  80

Phe Leu Ser Ala Val Lys Ala Tyr Pro Gly Phe Ala His Gly Gly Ser
                85                  90                  95

Glu Val Glu Arg Lys Arg Glu Ile Ala Ala Phe Phe Ala His Val Thr
            100                 105                 110

His Glu Thr Gly His Phe Cys Tyr Ile Ser Glu Ile Asn Lys Ser Asn
        115                 120                 125

Ala Tyr Cys Asp Pro Thr Lys Arg Gln Trp Pro Cys Ala Ala Gly Gln
    130                 135                 140

Lys Tyr Tyr Gly Arg Gly Pro Leu Gln Ile Ser Trp Asn Tyr Asn Tyr
145                 150                 155                 160

Gly Pro Ala Gly Arg Ala Ile Gly Phe Asp Gly Leu Gly Asp Pro Gly
                165                 170                 175

Arg Val Ala Arg Asp Ala Val Val Ala Phe Lys Ala Ala Leu Trp Phe
            180                 185                 190

Trp Met Asn Asn Val His Arg Val Met Pro Gln Gly Phe Gly Ala Thr
        195                 200                 205

Ile Arg Ala Ile Asn Gly Ala Leu Glu Cys Gly Gly Asn Asn Pro Ala
    210                 215                 220

Gln Met Asn Ala Arg Val Gly Tyr Tyr Lys Gln Tyr Cys Arg Gln Leu
225                 230                 235                 240
```

-continued

```
Gly Val Asp Pro Gly Pro Asn Leu Thr Cys
                245                 250
```

<210> SEQ ID NO 45
<211> LENGTH: 771
<212> TYPE: DNA
<213> ORGANISM: Unknown
<220> FEATURE:
<223> OTHER INFORMATION: Variant sequence produced by shuffling
      techniques 4N1/80_F8 nucleic acid

<400> SEQUENCE: 45

```
tcgatgcaga actgcggctg ccagccaaac gtatgctgca gccggttcgg ctactgcggc      60
acgaccgacg agtactgcgg cgacgggtgc cggtcgggcc cgtgccgctc gggcggcggt     120
ggcggcggcg gcggcggcgg aggcggcgga ggcagtggcg gtgcgaacgt ggctaatgtg     180
gtcaccgacg cgttcttcaa cggcatcaag aaccaggccg ggagcgggtg cgagggcaag     240
aacttctaca cccggagcgc gttcctgagc gccgtcaagg cgtacccagg cttcgcccat     300
ggcgggtcgc aggtgcaggg caagcgcgag atcgccgcct tcttcgcgca cgccacgcac     360
gagaccgggc atttctgcta catcagcgag atcaacaaga gcaacgccta ctgcgacccg     420
accaagaggc agtggccgtg cgccgcgggg cagaagtact acgggcgcgg cccgctgcag     480
atctcgtgga actacaacta cgggcccgcg gggagggcca tcggctttga cgggctcggg     540
gaccccaaca gggtggcgcg ggacgccgtg gtgcgttca aggcggcgct ctggttctgg     600
atgaacagcg tgcacgggt ggtgccgcag gggttcggcg ccaccaccag ggccatcaac     660
ggcgccctcg agtgcaacgg gaacaacccc gcccagatga acgcgcgcgt cggctactac     720
aagcagtact gccgccagct cggcgtcgac ccagggccca acctcacttg c              771
```

<210> SEQ ID NO 46
<211> LENGTH: 257
<212> TYPE: PRT
<213> ORGANISM: Unknown
<220> FEATURE:
<223> OTHER INFORMATION: Variant sequence produced by shuffling
      techniques 4N1/80_F8

<400> SEQUENCE: 46

```
Ser Met Gln Asn Cys Gly Cys Gln Pro Asn Val Cys Cys Ser Arg Phe
  1               5                  10                  15
Gly Tyr Cys Gly Thr Thr Asp Glu Tyr Cys Gly Asp Gly Cys Arg Ser
                 20                  25                  30
Gly Pro Cys Arg Ser Gly Gly Gly Gly Gly Gly Gly Gly Gly Gly Gly
             35                  40                  45
Gly Gly Gly Ser Gly Gly Ala Asn Val Ala Asn Val Val Thr Asp Ala
         50                  55                  60
Phe Phe Asn Gly Ile Lys Asn Gln Ala Gly Ser Gly Cys Glu Gly Lys
 65                  70                  75                  80
Asn Phe Tyr Thr Arg Ser Ala Phe Leu Ser Ala Val Lys Ala Tyr Pro
                 85                  90                  95
Gly Phe Ala His Gly Gly Ser Gln Val Gln Gly Lys Arg Glu Ile Ala
            100                 105                 110
Ala Phe Phe Ala His Ala Thr His Glu Thr Gly His Phe Cys Tyr Ile
        115                 120                 125
Ser Glu Ile Asn Lys Ser Asn Ala Tyr Cys Asp Pro Thr Lys Arg Gln
    130                 135                 140
```

-continued

```
Trp Pro Cys Ala Ala Gly Gln Lys Tyr Tyr Gly Arg Gly Pro Leu Gln
145                 150                 155                 160
Ile Ser Trp Asn Tyr Asn Tyr Gly Pro Ala Gly Arg Ala Ile Gly Phe
                165                 170                 175
Asp Gly Leu Gly Asp Pro Asn Arg Val Ala Arg Asp Ala Val Val Ala
            180                 185                 190
Phe Lys Ala Ala Leu Trp Phe Trp Met Asn Ser Val His Gly Val Val
        195                 200                 205
Pro Gln Gly Phe Gly Ala Thr Thr Arg Ala Ile Asn Gly Ala Leu Glu
    210                 215                 220
Cys Asn Gly Asn Asn Pro Ala Gln Met Asn Ala Arg Val Gly Tyr Tyr
225                 230                 235                 240
Lys Gln Tyr Cys Arg Gln Leu Gly Val Asp Pro Gly Pro Asn Leu Thr
                245                 250                 255
Cys
```

<210> SEQ ID NO 47
<211> LENGTH: 768
<212> TYPE: DNA
<213> ORGANISM: Unknown
<220> FEATURE:
<223> OTHER INFORMATION: Variant sequence produced by shuffling
      techniques 4N1/75_D3

<400> SEQUENCE: 47

```
tcgatgcaga actgcggctg ccagccaaac gtatgctgca gcaagttcgg ctactgcggc        60
acgaccgacg agtactgcgg cgacgggtgc cagtcgggcc cgtgccgctc gggcggcggc       120
ggcggcggcg gcggcggagg cggcggaggc agtggcggtg cgaacgtggc tagcgtcgtc       180
accggctcct tcttcaacgg catcaagaac caggccggga gcgggtgcga gggcaagaac       240
ttctacaccc ggagcgcgtt cctgagcgcc gtcaaggcgt acccaggctt cgcccatggc       300
gggtcacagg tgcagggcaa gcgcgagatc gccgccttct tcgcgcatgt cacgcacgag       360
accgggcatt ccgctacat cagcgaggtc aacaagagca acgcctactg cgacccgacc        420
aagaggcagt ggccgtgcgc cgcggggcag aagtactacg ggcgcggccc gctgcagatc       480
tcgtggaact acaactacgg gcccgcgggg agggccatcg gctttgacgg gctcggggac       540
cccggcaggg tggcgcggga cgccgtggtg gcgttcaagg cggcgctctg gttctggatg       600
aacaacgtgc accgtgtgat gccgcagggc ttcggcgcca ccatcagggc catcaacggc       660
gccctcgagt gcgcgggaa caaccccgcc cagatgaacg cgcgcgtcgg ctactacagg       720
cagtactgcc gccagctcgg cgtcgaccca gggcccaacc tcacttgc                    768
```

<210> SEQ ID NO 48
<211> LENGTH: 256
<212> TYPE: PRT
<213> ORGANISM: Unknown
<220> FEATURE:
<223> OTHER INFORMATION: Variant sequence produced by shuffling
      techniques 4N1/75_D3

<400> SEQUENCE: 48

```
Ser Met Gln Asn Cys Gly Cys Gln Pro Asn Val Cys Cys Ser Lys Phe
1               5                   10                  15
Gly Tyr Cys Gly Thr Thr Asp Glu Tyr Cys Gly Asp Gly Cys Gln Ser
            20                  25                  30
Gly Pro Cys Arg Ser Gly Gly Gly Gly Gly Gly Gly Gly Gly Gly Gly
        35                  40                  45
```

Gly Gly Ser Gly Gly Ala Asn Val Ala Ser Val Thr Gly Ser Phe
 50                  55                  60

Phe Asn Gly Ile Lys Asn Gln Ala Gly Ser Gly Cys Glu Gly Lys Asn
 65                  70                  75                  80

Phe Tyr Thr Arg Ser Ala Phe Leu Ser Ala Val Lys Ala Tyr Pro Gly
                 85                  90                  95

Phe Ala His Gly Ser Gln Val Gln Gly Lys Arg Glu Ile Ala Ala
            100                 105                 110

Phe Phe Ala His Val Thr His Glu Thr Gly His Phe Arg Tyr Ile Ser
            115                 120                 125

Glu Val Asn Lys Ser Asn Ala Tyr Cys Asp Pro Thr Lys Arg Gln Trp
        130                 135                 140

Pro Cys Ala Ala Gly Gln Lys Tyr Tyr Gly Arg Gly Pro Leu Gln Ile
145                 150                 155                 160

Ser Trp Asn Tyr Asn Tyr Gly Pro Ala Gly Arg Ala Ile Gly Phe Asp
                165                 170                 175

Gly Leu Gly Asp Pro Gly Arg Val Ala Arg Asp Ala Val Val Ala Phe
            180                 185                 190

Lys Ala Ala Leu Trp Phe Trp Met Asn Asn Val His Arg Val Met Pro
        195                 200                 205

Gln Gly Phe Gly Ala Thr Ile Arg Ala Ile Asn Gly Ala Leu Glu Cys
    210                 215                 220

Gly Gly Asn Asn Pro Ala Gln Met Asn Ala Arg Val Gly Tyr Tyr Arg
225                 230                 235                 240

Gln Tyr Cys Arg Gln Leu Gly Val Asp Pro Gly Pro Asn Leu Thr Cys
                245                 250                 255

<210> SEQ ID NO 49
<211> LENGTH: 750
<212> TYPE: DNA
<213> ORGANISM: Unknown
<220> FEATURE:
<223> OTHER INFORMATION: Variant sequence produced by shuffling
      techniques 4N1/2_H9 nucleic acid

<400> SEQUENCE: 49
tcgatgcaga actgcggctg ccagccaaac gtatgctgca gcaagtttgg ctactgcggc      60
acgaccgacg agtactgcgg cgacgggtgc cagtcgggcc cgtgccgctc gggcggcggc     120
ggcagcagtg gcggcggtgg tgtgaacgtg gccagcatcg tgaccggctc cttcttcaac     180
ggcatcaaga accaggccgg gagcgggtgc gagggcaaga acttctacac ccggagcgcg     240
ttcctgagcg ccgtcaaggc gtacccaggc ttcgcccatg gcgggacgga ggtggagggc     300
aagcgcgaga tcgccgcctt cttcgcgcat gtcacgcatg agaccgggca tttctgctac     360
atcagcgaga tcagcaagag caacgcctac tgcgacccga ccaagaggca gtggccgtgc     420
gccgcgggc agaagtacta cgggcgcggc ccgctgcaga tctcgtggaa ctacaactac     480
gggcccgcgg ggagggccat cggcttcgac gggctcgggg accccggcag ggtggcgcgg     540
gacgctgtgg tggcgttcaa ggcggcgctc tggttctgga tgaacagcgt gcacggggtg     600
gcgccgcagg ggttcggcgc caccatcagg gccatcaacg cgcactcga gtgcggcggg      660
aacaaccccg cccagatgaa cgcgcgcgtc ggctactaca gcagtactg ccaccagctc      720
ggcgtcgacc cagggcccaa cctcacttgc                                       750

<210> SEQ ID NO 50

```
<211> LENGTH: 250
<212> TYPE: PRT
<213> ORGANISM: Unknown
<220> FEATURE:
<223> OTHER INFORMATION: Variant sequence produced by shuffling
      techniques 4N1/2_H9

<400> SEQUENCE: 50

Ser Met Gln Asn Cys Gly Cys Gln Pro Asn Val Cys Cys Ser Lys Phe
 1               5                  10                  15

Gly Tyr Cys Gly Thr Thr Asp Glu Tyr Cys Gly Asp Gly Cys Gln Ser
            20                  25                  30

Gly

```
atcagcgaga tcaacaagag caacgcctac tgcgacccga ccaagaggca gtggccgtgc      420 gccgcgggc  agaagtacta cgggcgcggc cgctgcaga  tctcgtggaa ctacaactac      480
gggcccgcgg ggagggccat cggcttcgac gggctcgggg accccggcag ggtggcgcgg      540
gacgccgtgg tggcgttcaa ggcggcgctc tggttctgga tgaacaacgt gcaccgtgtg      600
atgccgcagg gcttcggcgc caccatcagg gccatcaacg cgccctcga  gtgcggcggg      660 aacaaccccg cccagatgaa cgcgcgcgtc ggctactaca ggcagtactg ccgccagctc      720
ggcgtcgacc cagggcccaa cctcacttgc                                      750
```

```
<210> SEQ ID NO 52
<211> LENGTH: 250
<212> TYPE: PRT
<213> ORGANISM: Unknown
<220> FEATURE:
<223> OTHER INFORMATION: Variant sequence produced by shuffling
      techniques 4N1/23_G4

<400> SEQUENCE: 52

Ser Met Gln Asn Cys Gly Cys Gln Pro Asn Val Cys Cys Ser Lys Phe
  1               5                  10                  15

Gly Tyr Cys Gly Thr Thr Asp Glu Tyr Cys Gly Asp Gly Cys Gln Ser
             20                  25                  30

Gly Pro Cys Arg Ser Gly Gly Gly Ser Gly Gly Gly Gly Ala
         35                  40                  45

Asn Val

```
<220> FEATURE:
<223> OTHER INFORMATION: Variant sequence produced by shuffling
      techniques 4N1/68_E4 nucleic acid

<400> SEQUENCE: 53
tcgatgcaga actgcggctg ccagccaaac gtatgctgca gcaagtttgg ctactgcggc      60
acgaccgacg agtactgcgg cgccgggtgc cagtcgggcc cgtgccactc gggcggcggc     120
ggcagcagtg gcggcggtgg tgcgaacgtg gctagcgtcg tcaccggctc cttcttcaac     180
ggcatcaaga accaggccgg gagcgggtgc gagggcaaga acttctacac ccggagcgcg     240
ttcctgagcg ccgtcaaggc gtacccaggc ttcgcccatg gcgggtcgca ggtgcagggc     300
aagcgcgaga tcgccgcctt cttcgcgcat gtcacgcatg agaccgggca tttctgctac     360
atcagcgaga tcaacaagag caacgcctac tgcgacccga ccaagaggca gtggccgtgc     420 gccgcgggc agaagtacta cgggcgcggc ccgctgcagc tgtcgtggaa ctacaactac      480
gggcccgccg gagggacat cggcttcaac gggctcgccg accccaacag ggtggcgcag      540
gacgccgtga tcgcgttcaa gtcggcgctc tggttctgga tgaacaacgt gcaccgtgtg     600
atgccgcagg gcttcggcgc caccatcagg gccatcaacg gcgccctcga gtgcggcggg     660
aacaaccccg cccagatgaa cgcgcgcgtc ggctactaca ggcagtactg ccgccagctc     720
ggcgtcgacc cagggcccaa cctcacttgc                                     750

<210> SEQ ID NO 54
<211> LENGTH: 250
<212> TYPE: PRT
<213> ORGANISM: Unknown
<220> FEATURE:
<223> OTHER INFORMATION: Variant sequence produced by shuffling
      techniques 4N1/68_E4

<400> SEQUENCE: 54

Ser Met Gln Asn Cys Gly Cys Gln Pro Asn Val Cys Cys Ser Lys Phe
 1               5                  10                  15

Gly Tyr Cys Gly Thr Thr Asp Glu Tyr Cys Gly Ala Gly Cys Gln Ser
            20                  25                  30

Gly Pro Cys His Ser Gly Gly Gly Gly Ser Gly Gly Gly Gly

```
Trp Met Asn Asn Val His Arg Val Met Pro Gln Gly Phe Gly Ala Thr
        195                 200                 205

Ile Arg Ala Ile Asn Gly Ala Leu Glu Cys Gly Gly Asn Asn Pro Ala
    210                 215                 220

Gln Met Asn Ala Arg Val Gly Tyr Tyr Arg Gln Tyr Cys Arg Gln Leu
225                 230                 235                 240

Gly Val Asp Pro Gly Pro Asn Leu Thr Cys
                245                 250

<210> SEQ ID NO 55
<211> LENGTH: 750
<212> TYPE: DNA
<213> ORGANISM: Unknown
<220> FEATURE:
<223> OTHER INFORMATION: Variant sequence produced by shuffling
      techniques 4N1/88_F9 nucleic acid

<400> SEQUENCE: 55
tcgatgcaga actgcggctg ccagccaaac gtatgctgca gcaagtttgg ctactgcggc      60
acaaccgacg agtactgcgg cgacgggtgc cagtcgggcc cgtgccactc gggcggcggt     120
ggcggcggtg gcggcggtgg tgcgaacgtg gctagcgtcg tcaccggctc cttcttcaac     180
ggcatcaaga accaggccgg gagcgggtgc gagggcaaga acttctacac ccggagcgcg     240
ttcctgagcg ccgtcaaggc gtacccaggc ttcgcccatg gcgggtcaca ggtgcagggc     300
aagcgcgaga tcgccgcctt cttcgcgcat gtcacgcacg agaccgggca tttctgctac     360
atcagcgaga tcaacaagag caacgcctac tgcgacccga ccaagaggca gtggccgtgc     420
gccgcggggc agaagtacta cgggcgcggc ccgctgcaga tctcgtggaa ctacaactac     480
gggcccgcgg ggagggacat cggcttcaac gggctcgccg accccaacag ggtggcgcag     540
gacgccgtgg tggcgttcaa ggcggcgctc tggttctgga tgaacaacgt gcaccgtgtg     600
atgccgcagg gcttcggcgc caccatcagg gccatcaacg gcgccctcga gtgcggcggg     660
aacaaccccg cccagatgaa cgcgcgcatc ggctactaca gcagtactg ccgccagctc     720 ggcgtcgacc cagggcccaa cctcacttgc                                     750

<210> SEQ ID NO 56
<211> LENGTH: 250
<212> TYPE: PRT
<213> ORGANISM: Unknown
<220> FEATURE:
<223> OTHER INFORMATION: Variant sequence produced by shuffling
      techniques 4N1/88_F9

<400> SEQUENCE: 56

Ser Met Gln Asn Cys Gly Cys Gln Pro Asn Val Cys Cys Ser Lys Phe
1               5                   10                  15

Gly Tyr Cys Gly Thr Thr Asp Glu Tyr Cys Gly Asp Gly Cys Gln Ser
                20                  25                  30

Gly Pro Cys His Ser Gly Gly Gly Gly Gly Gly Gly Gly Gly Gly Ala
            35                  40                  45

Asn Val Ala Ser Val Val Thr Gly Ser Phe Phe Asn Gly Ile Lys Asn
        50                  55                  60

Gln Ala Gly Ser Gly Cys Glu Gly Lys Asn Phe Tyr Thr Arg Ser Ala
65                  70                  75                  80

Phe Leu Ser Ala Val Lys Ala Tyr Pro Gly Phe Ala His Gly Gly Ser
                85                  90                  95

Gln Val Gln Gly Lys Arg Glu Ile Ala Ala Phe Phe Ala His Val Thr
```

```
                100             105             110
        His Glu Thr Gly His Phe Cys Tyr Ile Ser Glu Ile Asn Lys Ser Asn
                115                 120                 125

Ala Tyr Cys Asp Pro Thr Lys Arg Gln Trp Pro Cys Ala Ala Gly Gln
        130                 135                 140

Lys Tyr Tyr Gly Arg Gly Pro Leu Gln Ile Ser Trp Asn Tyr Asn Tyr
        145                 150                 155                 160

Gly Pro Ala Gly Arg Asp Ile Gly Phe Asn Gly Leu Ala Asp Pro Asn
                        165                 170                 175

Arg Val Ala Gln Asp Ala Val Ala Phe Lys Ala Ala Leu Trp Phe
                    180                 185                 190

Trp Met Asn Asn Val His Arg Val Met Pro Gln Gly Phe Gly Ala Thr
                    195                 200                 205

Ile Arg Ala Ile Asn Gly Ala Leu Glu Cys Gly Gly Asn Asn Pro Ala
                210                 215                 220

Gln Met Asn Ala Arg Ile Gly Tyr Tyr Lys Gln Tyr Cys Arg Gln Leu
        225                 230                 235                 240

Gly Val Asp Pro Gly Pro Asn Leu Thr Cys
                        245                 250

<210> SEQ ID NO 57
<211> LENGTH: 750
<212> TYPE: DNA
<213> ORGANISM: Unknown
<220> FEATURE:
<223> OTHER INFORMATION: Variant sequence produced by shuffling
      techniques 4N1/14_B3 nucleic acid

<400> SEQUENCE: 57
tcgatgcaga attgcggctg ccagccaaac gtatgctgca gcaagttcgg ctactgcggc      60
acgaccgacg agtactgcgg cgccgggtgc cagtcgggcc cgtgccgctc ggcggcggc     120 ggcagcagtg gcggcggtgg tgcgaacgtg gctagcgtcg tcaccggctc cttcttcaac    180
ggcatcaaga accaggccgg gagcgggtgc gagggcaaga acttctacac ccggagcgcg    240
ttcctgagcg ccgtcaacgc gtacccgggc ttcgcccatg gcgggacgga ggtggagcgc    300
aagcgcgaga ttgccgcctt cttcgcgcac gccacgcacg agaccgggca ttttctgctac   360 atcagcgaga tcaacaagag caacgcctac tgcgacccga ccaagaggca gtggccgtgc    420 gccgcgggc agaagtacta cgggcgcggc ccgctgcaga tctcgtggaa ctacaactac    480
gggcccgcgg gggggccat cggcttcgac gggctcgggg accccggcag ggtggcgcgg    540
gacgccgtgg tggcgttcaa ggcggcgctc tggttctgga tgaacaacgt gcaccgtgtg    600
atgccgcagg gcttcggcgc caccatccgg gccatcaacg cgccctcga gtgcgacggc     660 aagaaccca actccgtcaa caaccgcgtc gcctactaca ggcagtactg ccgccagctc     720
ggcgtcgacc cagggcccaa cctcacttgc                                     750

<210> SEQ ID NO 58
<211> LENGTH: 250
<212> TYPE: PRT
<213> ORGANISM: Unknown
<220> FEATURE:
<223> OTHER INFORMATION: Variant sequence produced by shuffling
      techniques 4N1/14_B3

<400> SEQUENCE: 58

Ser Met Gln Asn Cys Gly Cys Gln Pro Asn Val Cys Cys Ser Lys Phe
1               5                   10                  15
```

```
Gly Tyr Cys Gly Thr Thr Asp Glu Tyr Cys Gly Ala Gly Cys Gln Ser
            20                  25                  30

Gly Pro Cys Arg Ser Gly Gly Gly Ser Ser Gly Gly Gly Gly Ala
        35                  40                  45

Asn Val Ala Ser Val Val Thr Gly Ser Phe Phe Asn Gly Ile Lys Asn
    50                  55                  60

Gln Ala Gly Ser Gly Cys Glu Gly Lys Asn Phe Tyr Thr Arg Ser Ala
65                  70                  75                  80

Phe Leu Ser Ala Val Asn Ala Tyr Pro Gly Phe Ala His Gly Thr
                85                  90                  95

Glu Val Glu Arg Lys Arg Glu Ile Ala Ala Phe Phe Ala His Ala Thr
                100                 105                 110

His Glu Thr Gly His Phe Cys Tyr Ile Ser Glu Ile Asn Lys Ser Asn
                115                 120                 125

Ala Tyr Cys Asp Pro Thr Lys Arg Gln Trp Pro Cys Ala Ala Gly Gln
        130                 135                 140

Lys Tyr Tyr Gly Arg Gly Pro Leu Gln Ile Ser Trp Asn Tyr Asn Tyr
145                 150                 155                 160

Gly Pro Ala Gly Gly Ala Ile Gly Phe Asp Gly Leu Gly Asp Pro Gly
                165                 170                 175

Arg Val Ala Arg Asp Ala Val Val Ala Phe Lys Ala Ala Leu Trp Phe
            180                 185                 190

Trp Met Asn Asn Val His Arg Val Met Pro Gln Gly Phe Gly Ala Thr
            195                 200                 205

Ile Arg Ala Ile Asn Gly Ala Leu Glu Cys Asp Gly Lys Asn Pro Asn
    210                 215                 220

Ser Val Asn Asn Arg Val Ala Tyr Tyr Arg Gln Tyr Cys Arg Gln Leu
225                 230                 235                 240

Gly Val Asp Pro Gly Pro Asn Leu Thr Cys
                245                 250

<210> SEQ ID NO 59
<211> LENGTH: 768
<212> TYPE: DNA
<213> ORGANISM: Unknown
<220> FEATURE:
<223> OTHER INFORMATION: Variant sequence produced by shuffling
      techniques 4N1/33_F4 nucleic acid

<400> SEQUENCE: 59
tcgatgcaga actgcggctg ccagccaaac ttctgctgca gcaagtttgg ctactgcggc      60
acgaccgacg cctactgcgg cgacgggtgc cagtcgggcc cgtgccgctc gggcggcggt     120
ggcggcggtg gcggcggagg cggcggaggc agtggcggtg cgaacgtggc taatgtggtc     180
accgacgcgt tcttcaacgg catcaagaac caggccggga gcgggtgcga gggcaagaac     240
ttctacaccc ggagcgcgtt cctgagcgcc gtcaaggcgt acccaggctt cgcccatggc     300
gggtcacagg tgcagggcaa gcgcgagatt gccgccttct cgcgcatgt cacgcacgag      360 accgggcatt tctgctacat cagcgagatc aacaagagca cgcctactg cgaccccgacc    420 aagaggcagt ggccgtgcgc cgcggggcag aagtactacg gcgcggccc gctgcagatc     480 tcgtggaact acaactacgg gcccgcgggg agggccatcg gcttcgacgg gctcggggac    540
cccggcaggg tggcgcggga cgccgtggtg gcgttcaagg cggcgctctg gttctggatg    600
aacaacgtgc accgtgtgat gccgcagggc ttcggcgcca ccatcagggc catcaacggc    660
```

-continued

```
gccctcgagt gcgacgggaa aaccccgcc cagatgaacg cgcgcgtcgg ctactacagg    720
cagtactgcc gccagctcgg cgtcgaccca gggcccaacc tcacttgc                768
```

<210> SEQ ID NO 60
<211> LENGTH: 256
<212> TYPE: PRT
<213> ORGANISM: Unknown
<220> FEATURE:
<223> OTHER INFORMATION: Variant sequence produced by shuffling techniques 4N1/33_F4

<400> SEQUENCE: 60

```
Ser Met Gln Asn Cys Gly Cys Gln Pro Asn Phe Cys Cys Ser Lys Phe
 1               5                  10                  15
Gly Tyr Cys Gly Thr Thr Asp Ala Tyr Cys Gly Asp Gly Cys Gln Ser
            20                  25                  30
Gly Pro Cys Arg Ser Gly Gly Gly Gly Gly Gly Gly Gly Gly Gly Gly
        35                  40                  45
Gly Gly Ser Gly Gly Ala Asn Val Ala Asn Val Val

-continued

```
accggctcct tcttcaacgg catcaagagc caggccggga gcgggtgcga gggcaagaac    240
ttctacaccc ggagcgcgtt cctgagcgcc gtcaaggcgt acccaggctt cgcccatggc    300
ggctccgagg tcgagcgcaa cgcgagatt gccgccttct cgcgcacgc cacgcacgag     360 accgggcatt tctgctacat caacgagatc aacaagagca cgcctactg cgacccgacc    420 aagaggcagt ggccgtgcgc cgcggggcag aagtactacg gcgcggccc gctgcagatc    480 tcgtggaact acaactacgg gcccgcgggg agggccatcg gcttcgacgg gctcgccgac    540
cccggcaggt ggcgcggga cgccgtggtg gcgttcaagg cggcgctctg gttctggatg    600
aacaacgtgc accgtgtgat gccgcagggc ttcggcgcca ccatcagggc catcaacggc    660
gcgctcgagt gcgacgggaa caaccccgcc cagatgaacg cgcgcgtcgg ctactacaag    720
cagtactgcc gccagctcgg cgtcgaccca gggcccaacc tcacttgc                 768
```

<210> SEQ ID NO 62
<211> LENGTH: 256
<212> TYPE: PRT
<213> ORGANISM: Unknown
<220> FEATURE:
<223> OTHER INFORMATION: Variant sequence produced by shuffling
      techniques 4N1/11_B11

<400> SEQUENCE: 62

```
Ser Met Gln Asn Cys Gly Cys Gln Pro Asn Val Cys Cys Ser Lys Phe
 1               5                  10                  15

Gly Tyr Cys Gly Thr Thr Asp Glu Tyr Cys Gly Asp Gly Cys Gln Ser
            20                  25                  30

Gly Pro Cys Arg Pro Gly Gly Gly Gly Gly Gly Gly Gly Gly Gly Gly
        35                  40                  45

Gly Gly Ser Gly Gly Ala Asn Val Ala Ser Val Val Thr Gly Ser Phe
    50                  55                  60

Phe Asn Gly Ile Lys Ser Gln Ala Gly Ser Gly Cys Glu Gly Lys Asn
65                  70                  75                  80

Phe Tyr Thr Arg Ser Ala Phe Leu Ser Ala Val Lys Ala Tyr Pro Gly
                85                  90                  95

Phe Ala His Gly Gly Ser Glu Val Glu Arg Lys Arg Glu Ile Ala Ala
            100                 105                 110

Phe Phe Ala His Ala Thr His Glu Thr Gly His Phe Cys Tyr Ile Asn
        115                 120                 125

Glu Ile Asn Lys Ser Asn Ala Tyr Cys Asp Pro Thr Lys Arg Gln Trp
    130                 135                 140

Pro Cys Ala Ala Gly Gln Lys Tyr Tyr Gly Arg Gly Pro Leu Gln Ile
145                 150                 155                 160

Ser Trp Asn Tyr Asn Tyr Gly Pro Ala Gly Arg Ala Ile Gly Phe Asp
                165                 170                 175

Gly Leu Ala Asp Pro Gly Arg Val Ala Arg Asp Ala Val Val Ala Phe
            180                 185                 190

Lys Ala Ala Leu Trp Phe Trp Met Asn Asn Val His Arg Val Met Pro
        195                 200                 205

Gln Gly Phe Gly Ala Thr Ile Arg Ala Ile Asn Gly Ala Leu Glu Cys
    210                 215                 220

Asp Gly Asn Asn Pro Ala Gln Met Asn Ala Arg Val Gly Tyr Tyr Lys
225                 230                 235                 240

Gln Tyr Cys Arg Gln Leu Gly Val Asp Pro Gly Pro Asn Leu Thr Cys
                245                 250                 255
```

<210> SEQ ID NO 63
<211> LENGTH: 771
<212> TYPE: DNA
<213> ORGANISM: Unknown
<220> FEATURE:
<223> OTHER INFORMATION: Variant sequence produced by shuffling
      techniques 4N1/30_D3 nucleic acid

<400> SEQUENCE: 63

|

-continued

```
Ser Trp Asn Tyr Asn Tyr Gly Pro Ala Gly Arg Ala Ile Gly Phe Asp
                165                 170                 175

Gly Leu Gly Asp Pro Gly Arg Val Ala Arg Asp Ala Val Val Ala Phe
            180                 185                 190

Lys Ala Ala Leu Trp Phe Trp Met Asn Asn Val His Arg Val Met Pro
        195                 200                 205

Gln Gly Phe Gly Ala Thr Ile Arg Ala Ile Asn Gly Ala Leu Glu Cys
    210                 215                 220

Gly Gly Asn Asn Pro Ala Gln Met Asn Ala Arg Val Gly Tyr Tyr Arg
225                 230                 235                 240

Gln Tyr Cys Arg Gln Leu Gly Val Asp Pro Gly Pro Asn Leu Thr Cys
                245                 250                 255
```

```

<210> SEQ ID NO 65
<211> LENGTH: 771
<212> TYPE: DNA
<213> ORGANISM: Unknown
<220> FEATURE:
<223> OTHER INFORMATION: Variant sequence produced by shuffling
      techniques 4N1/35_G5 nucleic acid

<400> SEQUENCE: 65
tcgatgcaga actgcggctg ccagccaaac gtatgctgca gcaagtttgg ctactgcggc     60
acgaccgacg agtactgcgg cgacgggtgc cagtcgggcc cgtgccgccc gggtggcggt    120
ggcggcggcg gcggcggcgg aggcggcgga ggcagtggtg gtgcgaacgt ggctagcgtc    180
gtcaccgact ccttcttcaa cggcatcaag aaccaggccg ggagcgggtg cgagggcaag    240
aacttctaca cccggagcgc gttcctgagc gccgtcaagg cgtacccagg cttcgcccat    300
ggcgggtcgc aggtgcaggg caagcgcgag atcgccgcct tcttcgcgca tgtcacgcac    360
gagaccgggc atttctgcta catcagcgag atcaacaaga gcaacgccta ctgcgacccg    420
accaagaggc agtggccgtg cgccgcgggg cagaagtact acgggcgtgg cccgctgcag    480
atctcgtgga actacaacta cggcccgcg gggagggcca tcggcttcga cgggctcgcc    540
gaccccaaca gggtggcgca ggacgccgtg gtggcgttca aggcggcgct ctggttctgg    600
atgaacaacg tgcaccgtgt gatgccgcag ggcttcggcg ccaccatcag ggccatcaac    660
ggcgccctcg agtgcggcgg gaacaacccc gcccagatga acgcgcgcgt cggctactac    720
aagcagtact gccgccagct cggcgtcgac ccagggccca acctcacttg c             771
```

```

<210> SEQ ID NO 66
<211> LENGTH: 257
<212> TYPE: PRT
<213> ORGANISM: Unknown
<220> FEATURE:
<223> OTHER INFORMATION: Variant sequence produced by shuffling
      techniques 4N1/35_G5

<400> SEQUENCE: 66

Ser Met Gln Asn Cys Gly Cys Gln Pro Asn Val Cys Cys Ser Lys Phe
 1               5                  10                  15

Gly Tyr Cys Gly Thr Thr Asp Glu Tyr Cys Gly Asp Gly Cys Gln Ser
            20                  25                  30

Gly Pro Cys Arg Pro Gly Gly Gly Gly Gly Gly Gly Gly Gly Gly Gly
        35                  40                  45

Gly Gly Gly Ser Gly Gly Ala Asn Val Ala Ser Val Val Thr Asp Ser
    50                  55                  60

Phe Phe Asn Gly Ile Lys Asn Gln Ala Gly Ser Gly Cys Glu Gly Lys
```

-continued

```
             65                  70                  75                  80
Asn Phe Tyr Thr Arg Ser Ala Phe Leu Ser Ala Val Lys Ala Tyr Pro
                    85                  90                  95

Gly Phe Ala His Gly Gly Ser Gln Val Gln Gly Lys Arg Glu Ile Ala
                100                 105                 110

Ala Phe Phe Ala His Val Thr His Glu Thr Gly His Phe Cys Tyr Ile
            115                 120                 125

Ser Glu Ile Asn Lys Ser Asn Ala Tyr Cys Asp Pro Thr Lys Arg Gln
    130                 135                 140

Trp Pro Cys Ala Ala Gly Gln Lys Tyr Tyr Gly Arg Gly Pro Leu Gln
145                 150                 155                 160

Ile Ser Trp Asn Tyr Asn Tyr Gly Pro Ala Gly Arg Ala Ile Gly Phe
                165                 170                 175

Asp Gly Leu Ala Asp Pro Asn Arg Val Ala Gln Asp Ala Val Val Ala
                180                 185                 190

Phe Lys Ala Ala Leu Trp Phe Trp Met Asn Asn Val His Arg Val Met
            195                 200                 205

Pro Gln Gly Phe Gly Ala Thr Ile Arg Ala Ile Asn Gly Ala Leu Glu
    210                 215                 220

Cys Gly Gly Asn Asn Pro Ala Gln Met Asn Ala Arg Val Gly Tyr Tyr
225                 230                 235                 240

Lys Gln Tyr Cys Arg Gln Leu Gly Val Asp Pro Gly Pro Asn Leu Thr
                245                 250                 255

Cys
```